US010822608B2

(12) United States Patent
Erdos et al.

(10) Patent No.: US 10,822,608 B2
(45) Date of Patent: Nov. 3, 2020

(54) OLIGONUCLEOTIDE ANALOGUES TARGETING HUMAN LMNA

(71) Applicants: Sarepta Therapeutics, Inc., Cambridge, MA (US); THE UNITED STATES OF AMERICA, AS REPRESENTED BY THE SECRETARY, DEPT. OF HEALTH AND HUMAN SERVICES, Bethesda, MD (US); University of Maryland, College Park, MD (US); The Progeria Research Foundation, Peabody, MA (US)

(72) Inventors: Michael R. Erdos, Bethesda, MD (US); Francis S. Collins, Bethesda, MD (US); Kan Cao, Bowie, MD (US); Ryszard Kole, Cambridge, MA (US); Richard Keith Bestwick, Cambridge, MA (US); Leslie B. Gordon, Foxboro, MA (US)

(73) Assignees: Sarepta Therapeutics, Inc., Cambridge, MA (US); THE UNITED STATES OF AMERICA, AS REPRESENTED BY THE SECRETARY, DEPT. OF HEALTH AND HUMAN SERVICES, Bethesda, MD (US); University of Maryland, College Park, MD (US); The Progeria Research Foundation, Peabody, MA (US)

( * ) Notice: Subject to any disclaimer, the term of this patent is extended or adjusted under 35 U.S.C. 154(b) by 0 days.

(21) Appl. No.: 16/096,524

(22) PCT Filed: Apr. 28, 2017

(86) PCT No.: PCT/US2017/030174
§ 371 (c)(1),
(2) Date: Oct. 25, 2018

(87) PCT Pub. No.: WO2017/190041
PCT Pub. Date: Nov. 2, 2017

(65) Prior Publication Data
US 2019/0127735 A1    May 2, 2019

Related U.S. Application Data

(60) Provisional application No. 62/330,027, filed on Apr. 29, 2016.

(51) Int. Cl.
    C12N 15/113    (2010.01)
    A61P 43/00     (2006.01)
    C07K 7/06      (2006.01)

(52) U.S. Cl.
    CPC ............ *C12N 15/113* (2013.01); *A61P 43/00* (2018.01); *C07K 7/06* (2013.01); *C12N 2310/11* (2013.01); *C12N 2310/3183* (2013.01); *C12N 2310/323* (2013.01); *C12N 2310/3233* (2013.01); *C12N 2310/351* (2013.01); *C12N 2310/3513* (2013.01); *C12N 2320/33* (2013.01)

(58) Field of Classification Search
None
See application file for complete search history.

(56) References Cited

U.S. PATENT DOCUMENTS

2012/0289457 A1* 11/2012 Hanson ............... A61K 31/713
                                                       514/3.1

FOREIGN PATENT DOCUMENTS

| WO | WO 2007/047913 A2 | 4/2007 |
|----|-------------------|--------|
| WO | WO 2011/150408 A2 | 12/2011 |
| WO | WO 2012/150960 A1 | 11/2012 |
| WO | WO 2013/030569 A2 | 3/2013 |
| WO | WO 2013/086441 A2 | 6/2013 |
| WO | WO-2013086441 A2 * | 6/2013 |
| WO | WO 2015/175977 A2 | 11/2015 |

OTHER PUBLICATIONS

Yue-Bei et al., "Antisense Oligonucleotide Induction of Progerin in Human Myogenic Cells", PLoS One, vol. 9, No. 6, Jun. 1, 2014.
Osorio et al., "Splicing-Directed Therapy in a New Mouse Model of Human Accelerated Aging", Science Translational Medicine, vol. 3, No. 106, Oct. 26, 2011.
International Search Report and Written Opinion in related PCT Application No. PCT/US2017/030174, dated Sep. 14, 2017 (11 pages).

* cited by examiner

*Primary Examiner* — Tracy Vivlemore
(74) *Attorney, Agent, or Firm* — Brian C. Trinque; Lathrop GPM LLP

(57) ABSTRACT

Provided are LMNA-targeted antisense oligonucleotides for reducing expression of one or more aberrantly spliced LMNA mRNA isoforms that encode progerin.

4 Claims, 4 Drawing Sheets
Specification includes a Sequence Listing.

```
                        SEQUENCE LISTING

<160> NUMBER OF SEQ ID NOS: 25

<210> SEQ ID NO 1
<211> LENGTH: 270
<212> TYPE: DNA
<213> ORGANISM: Homo sapiens

<400> SEQUENCE: 1
ggctcccact gcagcagctc gggggacccc gctgagtaca acctgcgctc gcgcaccgtg      60
ctgtgcggga cctgcgggca gcctgccgac aaggcatctg ccagcggctc aggagcccag     120
gtgggcggac ccatctcctc tggctcttct gcctccagtg tcacggtcac tcgcagctac     180
cgcagtgtgg ggggcagtgg gggtggcagc ttcggggaca atctggtcac ccgctcctac     240
ctcctgggca actccagccc ccgaacccag                                      270

<210> SEQ ID NO 2
<211> LENGTH: 270
<212> TYPE: DNA
<213> ORGANISM: Homo sapiens

<400> SEQUENCE: 2
ggctcccact gcagcagctc gggggacccc gctgagtaca acctgcgctc gcgcaccgtg      60
ctgtgcggga cctgcgggca gcctgccgac aaggcatctg ccagcggctc aggagcccag     120
gtgggtggac ccatctcctc tggctcttct gcctccagtg tcacggtcac tcgcagctac     180
cgcagtgtgg ggggcagtgg gggtggcagc ttcggggaca atctggtcac ccgctcctac     240
ctcctgggca actccagccc ccgaacccag                                      270

<210> SEQ ID NO 3
<211> LENGTH: 25
<212> TYPE: DNA
<213> ORGANISM: Artificial Sequence
```

```
<220> FEATURE:
<223> OTHER INFORMATION: antisense oligonucleotide

<400> SEQUENCE: 3
ctgagccgct ggcagatgcc ttgtc                                              25

<210> SEQ ID NO 4
<211> LENGTH: 25
<212> TYPE: DNA
<213> ORGANISM: Artificial Sequence
<220> FEATURE:
<223> OTHER INFORMATION: antisense oligonucleotide

<400> SEQUENCE: 4
gaggagatgg gtccacccac ctggg                                              25

<210> SEQ ID NO 5
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 5

Arg Arg Arg Gln Arg Arg Lys Lys Arg
1               5

<210> SEQ ID NO 6
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 6

Arg Lys Lys Arg Arg Gln Arg Arg Arg
1               5

<210> SEQ ID NO 7
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 7

Arg Arg Arg Arg Arg Arg Arg Arg Arg Phe Phe
1               5                   10

<210> SEQ ID NO 8
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 8

Arg Arg Arg Arg Arg Phe Phe Arg Arg Arg Arg
1               5                   10

<210> SEQ ID NO 9
<211> LENGTH: 4
<212> TYPE: PRT
<213> ORGANISM: Artificial Sequence
<220> FEATURE:
<223> OTHER INFORMATION: cell penetrating peptide
```

```
<400> SEQUENCE: 9

Arg Arg Arg Arg
1

<210> SEQ ID NO 10
<211> LENGTH: 5
<212> TYPE: PRT
<213> ORGANISM: Artificial Sequence
<220> FEATURE:
<223> OTHER INFORMATION: cell penetrating peptide

<400> SEQUENCE: 10

Arg Arg Arg Arg Arg
1               5

<210> SEQ ID NO 11
<211> LENGTH: 6
<212> TYPE: PRT
<213> ORGANISM: Artificial Sequence
<220> FEATURE:
<223> OTHER INFORMATION: cell penetrating peptide

<400> SEQUENCE: 11

Arg Arg Arg Arg Arg Arg
1               5

<210> SEQ ID NO 12
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 12

Arg Arg Arg Arg Arg Arg Arg
1               5

<210> SEQ ID NO 13
<211> LENGTH: 8
<212> TYPE: PRT
<213> ORGANISM: Artificial Sequence
<220> FEATURE:
<223> OTHER INFORMATION: cell penetrating peptide

<400> SEQUENCE: 13

Arg Arg Arg Arg Arg Arg Arg Arg
1               5

<210> SEQ ID NO 14
<211> LENGTH: 9
<212> TYPE: PRT
<213> ORGANISM: Artificial Sequence
<220> FEATURE:
<223> OTHER INFORMATION: cell penetrating peptide

<400> SEQUENCE: 14

Arg Arg Arg Arg Arg Arg Arg Arg Arg
1               5

<210> SEQ ID NO 15
<211> LENGTH: 16
<212> TYPE: PRT
<213> ORGANISM: Artificial Sequence
<220> FEATURE:
<223> OTHER INFORMATION: cell penetrating peptide
<220> FEATURE:
<221> NAME/KEY: VARIANT
```

<222> LOCATION: 2,4,6,8,10,12,14,16
<223> OTHER INFORMATION: Xaa = 6-aminohexanoic acid

<400> SEQUENCE: 15

Arg Xaa Arg Xaa Arg Xaa Arg Xaa Arg Xaa Arg Xaa Arg Xaa Arg Xaa
1               5                   10                  15

<210> SEQ ID NO 16
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: VARIANT
<222> LOCATION: 2,5,8,11
<223> OTHER INFORMATION: Xaa = 6-aminohexanoic acid

<400> SEQUENCE: 16

Arg Xaa Arg Arg Xaa Arg Arg Xaa Arg Arg Xaa Arg
1               5                   10

<210> SEQ ID NO 17
<211> LENGTH: 15
<212> TYPE: PRT
<213> ORGANISM: Artificial Sequence
<220> FEATURE:
<223> OTHER INFORMATION: cell penetrating peptide
<220> FEATURE:
<221> NAME/KEY: VARIANT
<222> LOCATION: 2,5,8,11,14
<223> OTHER INFORMATION: Xaa = 6-aminohexanoic acid

<400> SEQUENCE: 17

Arg Xaa Arg Arg Xaa Arg Arg Xaa Arg Arg Xaa Arg Arg Xaa Arg
1               5                   10                  15

<210> SEQ ID NO 18
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: VARIANT
<222> LOCATION: 2
<223> OTHER INFORMATION: Xaa = 6-aminohexanoic acid
<220> FEATURE:
<221> NAME/KEY: VARIANT
<222> LOCATION: 5
<223> OTHER INFORMATION: Xaa = beta-alanine
<220> FEATURE:
<221> NAME/KEY: VARIANT
<222> LOCATION: 8
<223> OTHER INFORMATION: Xaa = 6-aminohexanoic acid
<220> FEATURE:
<221> NAME/KEY: VARIANT
<222> LOCATION: 11
<223> OTHER INFORMATION: Xaa = beta-alanine

<400> SEQUENCE: 18

Arg Xaa Arg Arg Xaa Arg Arg Xaa Arg Arg Xaa Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: cell penetrating peptide

```
<400> SEQUENCE: 19

Arg Ala Arg Arg Ala Arg Arg Ala Arg Arg Ala Arg Phe Phe
1               5                   10

<210> SEQ ID NO 20
<211> LENGTH: 14
<212> TYPE: PRT
<213> ORGANISM: Artificial Sequence
<220> FEATURE:
<223> OTHER INFORMATION: cell penetrating peptide

<400> SEQUENCE: 20

Arg Gly Arg Arg Gly Arg Arg Gly Arg Arg Gly Arg Phe Phe
1               5                   10

<210> SEQ ID NO 21
<211> LENGTH: 10
<212> TYPE: PRT
<213> ORGANISM: Artificial Sequence
<220> FEATURE:
<223> OTHER INFORMATION: cell penetrating peptide

<400> SEQUENCE: 21

Arg Phe Phe Arg Phe Phe Arg Phe Phe Arg
1               5                   10

<210> SEQ ID NO 22
<211> LENGTH: 14
<212> TYPE: PRT
<213> ORGANISM: Artificial Sequence
<220> FEATURE:
<223> OTHER INFORMATION: cell penetrating peptide
<220> FEATURE:
<221> NAME/KEY: VARIANT
<222> LOCATION: 2,5,8,11,13
<223> OTHER INFORMATION: Xaa = 6-aminohexanoic acid
<220> FEATURE:
<221> NAME/KEY: VARIANT
<222> LOCATION: 14
<223> OTHER INFORMATION: Xaa = beta-alanine

<400> SEQUENCE: 22

Arg Xaa Arg Arg Xaa Arg Arg Xaa Arg Arg Xaa Arg Xaa Xaa
1               5                   10

<210> SEQ ID NO 23
<211> LENGTH: 12
<212> TYPE: PRT
<213> ORGANISM: Artificial Sequence
<220> FEATURE:
<223> OTHER INFORMATION: cell penetrating peptide
<220> FEATURE:
<221> NAME/KEY: VARIANT
<222> LOCATION: 11
<223> OTHER INFORMATION: Xaa = 6-aminohexanoic acid
<220> FEATURE:
<221> NAME/KEY: VARIANT
<222> LOCATION: 12
<223> OTHER INFORMATION: Xaa = beta-alanine

<400> SEQUENCE: 23

Arg Phe Phe Arg Phe Phe Arg Phe Phe Arg Xaa Xaa
1               5                   10
```

```
<210> SEQ ID NO 24
<211> LENGTH: 11
<212> TYPE: PRT
<213> ORGANISM: Artificial Sequence
<220> FEATURE:
<223> OTHER INFORMATION: cell penetrating peptide

<400> SEQUENCE: 24

Arg Phe Phe Arg Phe Phe Arg Phe Phe Arg Gly
1               5                   10

<210> SEQ ID NO 25
<211> LENGTH: 7
<212> TYPE: PRT
<213> ORGANISM: Artificial Sequence
<220> FEATURE:
<223> OTHER INFORMATION: cell penetrating peptide

<400> SEQUENCE: 25

Arg Arg Arg Arg Arg Arg Gly
1               5
```

OLIGONUCLEOTIDE ANALOGUES TARGETING HUMAN LMNA

CROSS-REFERENCE TO RELATED APPLICATIONS

This application is a 35 U.S.C. § 371 filing of International Application No. PCT/US2017/030174, filed Apr. 28, 2017, which application claims priority to U.S. Provisional Application No. 62/330,027, filed Apr. 29, 2016. The entire contents of these applications are incorporated herein by reference in their entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 120178_503WO_SEQUENCE_LISTING.txt. The text file is about 6.5 KB, was created on Apr. 26, 2017, and is being submitted electronically via EFS web.

TECHNICAL FIELD

The present disclosure relates generally to human lamin A targeted antisense compounds.

BACKGROUND

Hutchinson-Gilford progeria syndrome (HGPS) is a rare genetic disorder characterized by premature arteriosclerosis and degeneration of vascular smooth muscle cells (SMCs). HGPS manifests itself most notably as accelerated, premature aging in affected children. Children with HGPS have progressive symptoms such as growth retardation, alopecia, loss of subcutaneous fat, and bone abnormalities. Average lifespan is 12 years with the most common cause of death being myocardial infarction or stroke.

Most HGPS cases are caused by a single-point mutation in the lamin A (LMNA) gene, resulting in the generation of progerin, a truncated splicing mutant of lamin A. The single-point mutation is a de novo silent substitution (1824C>T, Gly608Gly) in exon 11 of the lamin A (LMNA) gene. The substitution activates a cryptic splice donor site, which leads to the production of a dominant negative mutant lamin A protein with an internal deletion of 50 amino acids. The mutant protein, named progerin, accumulates on the nuclear membrane, causing characteristic nuclear blebbing ((Scaffidi and Misteli 2005; Cao, Blair et al. 2011)).

It is known that aberrant splicing can be corrected using phosphorodiamidate morpholino oligonucleotides (PMOs), or more specifically, splice-switching oligonucleotides (SSOs). SSOs block aberrant splicing sites by hybridizing at or near the sites thereby preventing recognition by the cellular splicing machinery. Exemplary SSOs are resistant to nucleases and the resulting double-stranded structure eliminates the possibility of RNA cleavage by RNase H. SSOs have been shown to effectively repair the splicing pattern both in vitro and in vivo for thalassemia and Duchenne muscular dystrophy. (Kinali, Arechavala-Gomeza et al. 2009; Svasti, Suwanmanee et al. 2009). The aberrant splicing of LMNA associated with HGPS has been shown to be reduced by correction of the aberrant splicing event using modified antisense oligonucleotides targeted to the activated cryptic splice site both in cell culture (Scaffidi and Misteli 2005) and in a relevant animal model (Osorio, Navarro et al. 2011).

PCT publications WO 2013/086441 and WO 2013/086444 disclose antisense oligomers targeting human lmna and methods of treating progeroid laminopathies using oligonucleotide analogues targeting human lmna, but do not disclose the antisense oligomer compounds and methods using the same of the instant disclosure.

Given the role of LMNA in HGPS, oligonucleotides that modulate splicing of LMNA pre-mRNA to eliminate expression of progerin are needed.

BRIEF SUMMARY

Embodiments of the present disclosure relate generally to antisense oligomers pharmaceutical compositions thereof and methods using the same that modulate aberrant splicing of LMNA pre-mRNA. In one aspect, the disclosure features a modified antisense oligonucleotide of 10 to 40 nucleobases. The modified antisense oligonucleotide includes a targeting sequence complementary to a target region within the pre-mRNA of LMNA.

In certain embodiments, the antisense oligomer is a compound of formula (I):

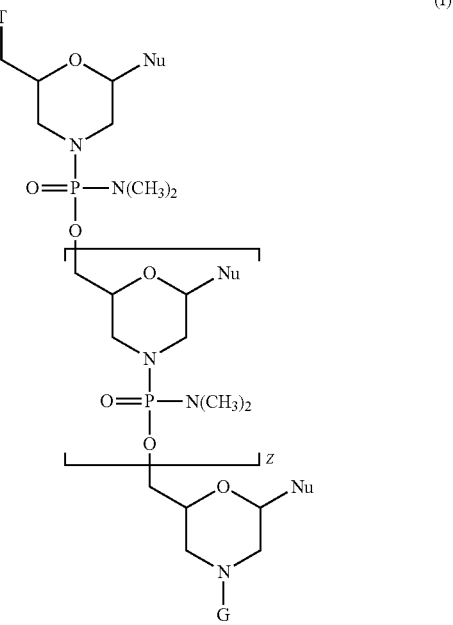

(I)

or a pharmaceutically acceptable salt thereof,
where each Nu is a nucleobase which taken together forms a targeting sequence;
Z is an integer from 8 to 38;
T is selected from:

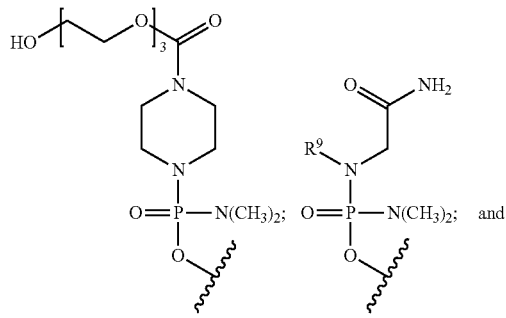

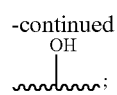

and

G is a cell penetrating peptide ("CPP") and linker moiety selected from —C(O)(CH$_2$)$_5$NH—CPP—R$^a$, —C(O)(CH$_2$)$_2$NH—CPP—R$^a$, —C(O)(CH$_2$)$_2$NHC(O)(CH$_2$)$_5$NH—CPP—R$^a$, —C(O)CH$_2$NH—CPP—R$^a$, and:

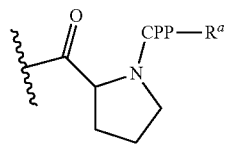

wherein the CPP is attached to the linker moiety by an amide bond at the CPP carboxy terminus, and R$^a$ is attached to the CPP amino terminus by an amide bond, wherein R$^a$ is selected from H, acetyl, benzoyl, and stearoyl. In some embodiments, R$^a$ is acetyl.

In various aspects, an antisense oligonucleotide of the disclosure includes a compound of formula (II):

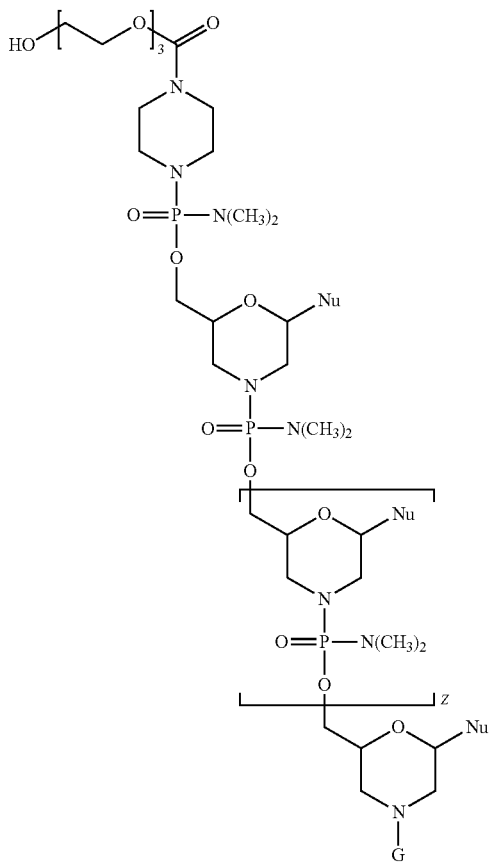

(II)

or a pharmaceutically acceptable salt thereof, wherein:

where each Nu is a nucleobase which taken together forms a targeting sequence;

Z is an integer from 8 to 38; and

G is a cell penetrating peptide ("CPP") and linker moiety selected from —C(O)(CH$_2$)$_5$NH—CPP—R$^a$, —C(O)(CH$_2$)$_2$NH—CPP—R$^a$, —C(O)(CH$_2$)$_2$NHC(O)(CH$_2$)$_5$NH—CPP—R$^a$, —C(O)CH$_2$NH—CPP—R$^a$, and:

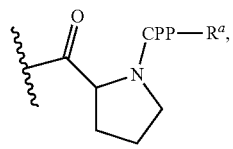

wherein the CPP is attached to the linker moiety by an amide bond at the CPP carboxy terminus, and R$^a$ is attached to the CPP amino terminus by an amide bond, wherein R$^a$ is selected from H, acetyl, benzoyl, and stearoyl. In some embodiments, R$^a$ is acetyl.

In some embodiments, the CPP is selected from SEQ ID NOS: 5-21. In some embodiments, G is selected from SEQ ID NOS: 22-25.

In various embodiments, G (as recited in formulas (I) and (II)) is selected from:

—C(O)CH$_2$NH—CPP and the formula:

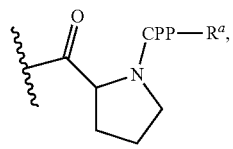

wherein the CPP is attached to the linker moiety by an amide bond at the CPP carboxy terminus, and R$^a$ is attached to the CPP amino terminus by an amide bond, and wherein the CPP—R$^a$ is selected from:

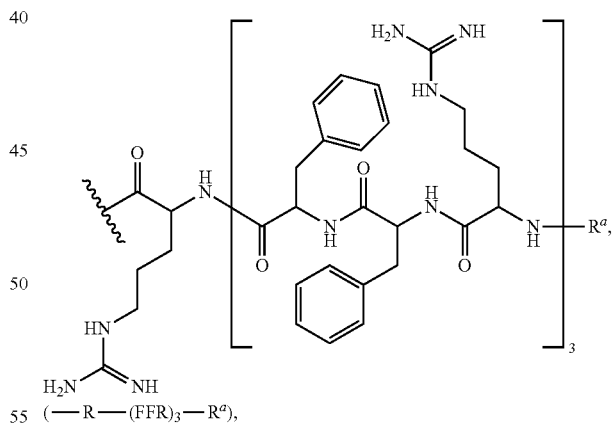

(—R—(FFR)$_3$—R$^a$),

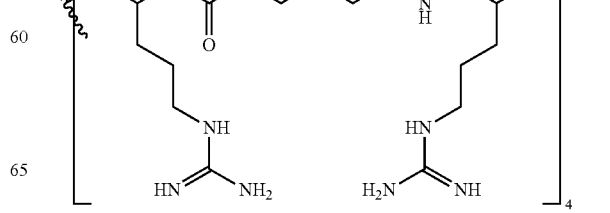

(—(RXR)$_4$—R$^a$), or

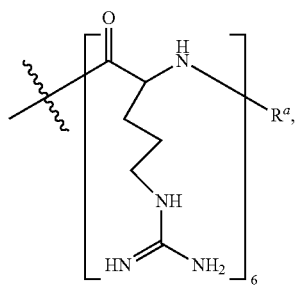

(—R$_6$—R$^a$), wherein R$^a$ is selected from H, acetyl, benzoyl, and stearoyl. In some embodiments, R$^a$ is acetyl.

In some embodiments, G (as recited in formulas (I) and (II)) is of the formula:

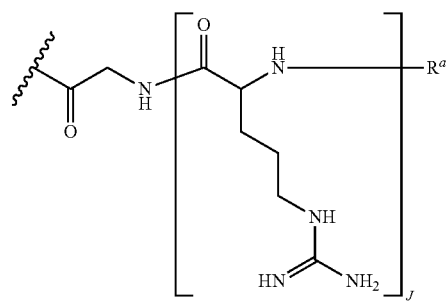

wherein R$^a$ is selected from H, acetyl, benzoyl, and stearoyl, and J is an integer from 4 to 9. In certain embodiments J is 6.

In various embodiments, the CPP—R$^a$ (as recited in formulas (I) and (II)) is of the formula:

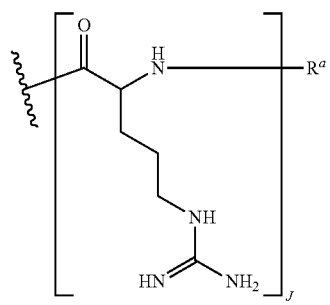

wherein R$^a$ is selected from H, acetyl, benzoyl, and stearoyl, and J is an integer from 4 to 9. In certain embodiments, the CPP is SEQ ID NO: 11. In various embodiments, J is 6. In some embodiments R$^a$ is selected from H and acetyl. For example, in some embodiments, R$^a$ is H. In certain embodiments, R$^a$ is acetyl.

In some embodiments, G is selected from SEQ ID NOS: 22-25. In certain embodiments, G is SEQ ID NO: 25.

In certain embodiments, G is —C(O)CH$_2$NH—R$_6$—R$^a$ covalently bonded to an antisense oligomer of the disclosure at the 3' end of the oligomer, wherein R$^a$ is H, acetyl, benzoyl, or stearoyl to cap the amino terminus of the R$_6$. In some embodiments, R$^a$ is acetyl. In these non-limiting examples, the CPP—R$^a$ is —R$_6$—R$^a$ and the linker is —C(O)CH$_2$NH—, (i.e., glycine). This particular example of G=—C(O)CH$_2$NH—R$_6$—R$^a$ is also exemplified by the following structure:

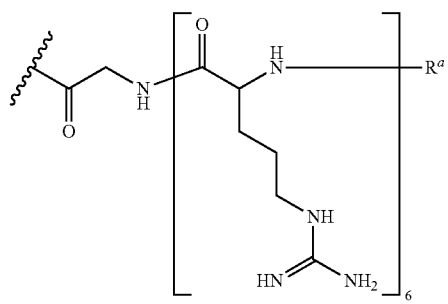

wherein R$^a$ is selected from H, acetyl, benzoyl, and stearoyl. In some embodiments, R$^a$ is acetyl.

In various embodiments, the CPP—R$^a$ is —R$_6$—R$^a$, also exemplified as the following formula:

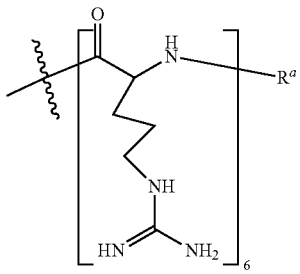

wherein R$^a$ is selected from H, acetyl, benzoyl, and stearoyl. In certain embodiments, the CPP is SEQ ID NO: 11. In some embodiments, R$^a$ is acetyl.

In some embodiments, the CPP—R$^a$ is —(RXR)$_4$—R$^a$, also exemplified as the following formula:

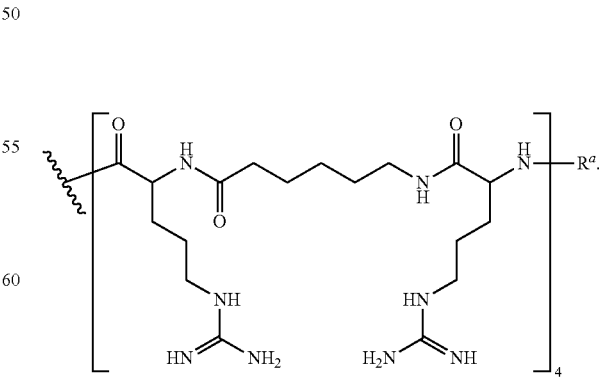

In various embodiments, the CPP—R$^a$ is —R—(FFR)$_3$—R$^a$, also exemplified as the following formula:

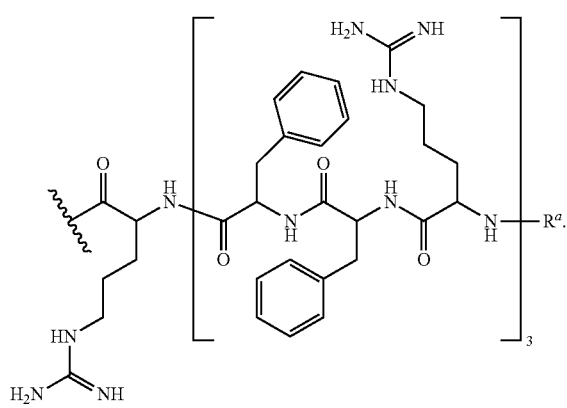

In some embodiments, the targeting sequence of an antisense oligomers of the disclosure, including, for example, some embodiments of the antisense oligomers of formula (I) and (II), is selected from:

a)
                                                    SEQ ID NO: 3
(CTGAGCCGCTGGCAGATGCCTTGTC)
wherein Z is 23;
and b)
                                                  SEQ ID NO: 4
(GAGGAGATGGGTCCACCCACCTGGG)
wherein Z is 23.

In another aspect of the disclosure, methods for the treatment of diseases, such as diseases or conditions associated with human LMNA, are provided. In certain embodiments, the methods are used in the treatment of progeroid diseases or related conditions, such as a progeroid laminopathy (such as HGPS), an age-related condition, or a cardiovascular disease (such as atherosclerosis).

In an additional aspect, the present disclosure provides pharmaceutical compositions comprising the antisense oligomers of the disclosure and a pharmaceutically acceptable carrier.

Thus, in a further aspect, the present disclosure also provides, in other embodiments, methods for treating progeroid laminopathies by administering a pharmaceutical composition comprising an antisense oligonucleotide as described herein and a pharmaceutically acceptable excipient.

These and other aspects of the disclosure will be apparent upon reference to the following detailed description. To this end, various references are set forth herein which describe in more detail certain background information, procedures, compounds and/or compositions, and are each hereby incorporated by reference in their entirety.

DETAILED DESCRIPTION OF THE DISCLOSURE

Figure 1:
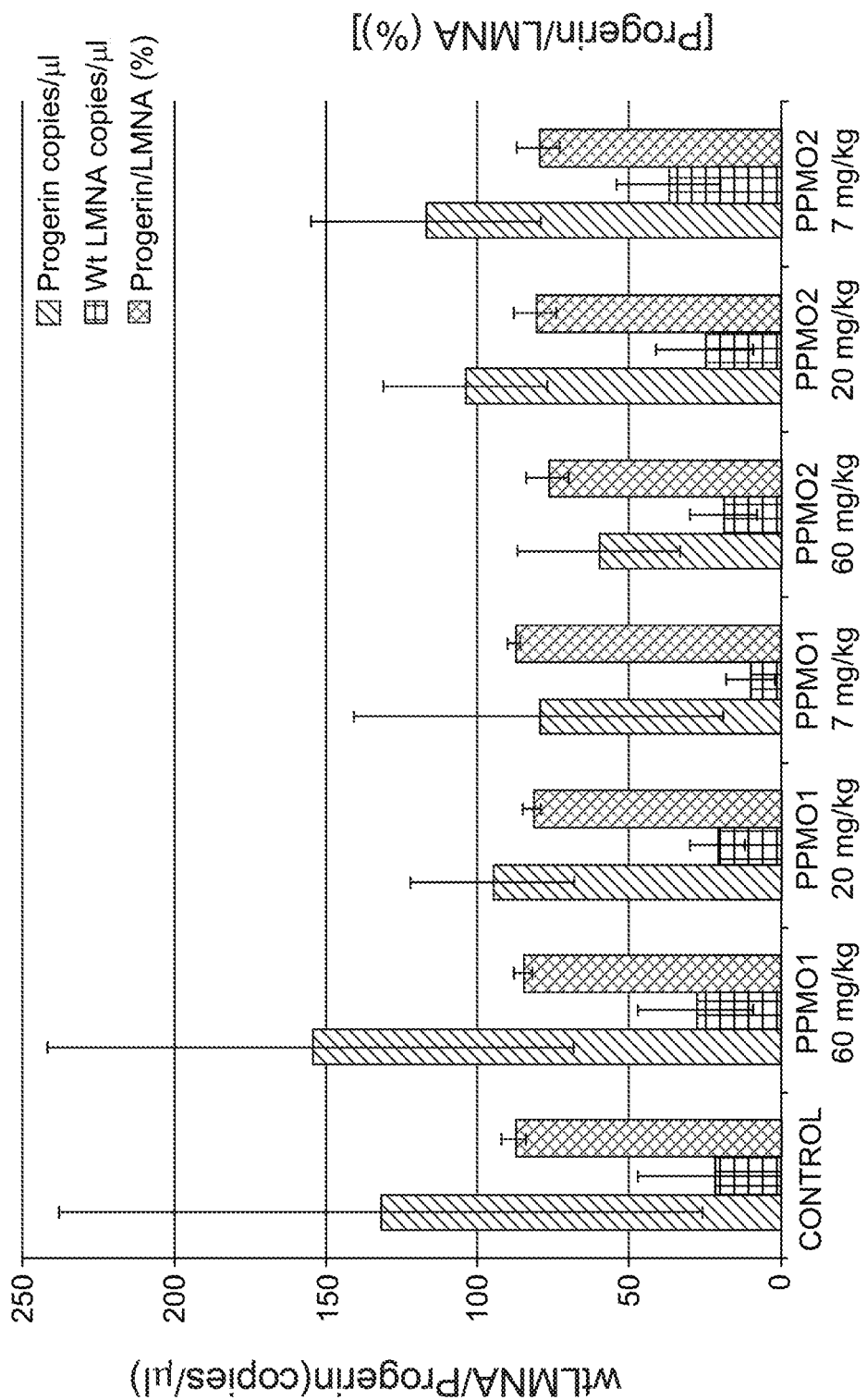
FIG. 1 shows results for ddPCR analysis of lamin A and progerin from the hearts of mice treated with PPMO1 (7 mg/kg, 20 mg/kg, or 60 mg/kg), PPMO2 (7 mg/kg, 20 mg/kg, or 60 mg/kg), or saline control for 12 weeks.

The present disclosure relates to oligonucleotides as described herein, and composition containing the same, as well as in vitro methods, wherein the oligonucleotides inhibit expression of mutant LMNA protein mRNA, e.g., by modulating splicing of LMNA pre-mRNA.

Definitions

Unless defined otherwise, all technical and scientific terms used herein have the same meaning as commonly understood by those of ordinary skill in the art to which the disclosure belongs. Although any methods and materials similar or equivalent to those described herein can be used in the practice or testing of the present disclosure, exemplary methods and materials are described. For the purposes of the present disclosure, the following terms are defined below.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30%, 25%, 20%, 25%, 10%, 9%, 8%, 7%, 6%, 5%, 4%, 3%, 2% or 1% to a reference quantity, level, value, number, frequency, percentage, dimension, size, amount, weight or length.

By "coding sequence" is meant any nucleic acid sequence that contributes to the code for the polypeptide product of a gene. By contrast, the term "non-coding sequence" refers to any nucleic acid sequence that does not contribute to the code for the polypeptide product of a gene.

Throughout this specification, unless the context requires otherwise, the words "comprise," "comprises," and "comprising" will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "complementary" and "complementarity" refer to polynucleotides (i.e., a sequence of nucleotides) related by the base-pairing rules. For example, the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. While perfect complementarity is often desired, some embodiments can include one or more but preferably 6, 5, 4, 3, 2, or 1 mismatches with respect to the target RNA. Variations at any location within the oligomer are included. In certain embodiments, variations in sequence near the termini of an oligomer are generally preferable to variations in the interior, and if present are typically within about 6, 5, 4, 3, 2, or 1 nucleotides of the 5' and/or 3' terminus.

The terms "cell penetrating peptide" or "CPP" are used interchangeably and refer to cationic cell penetrating peptides, also called transport peptides, carrier peptides, or peptide transduction domains. The peptides, as shown herein, have the capability of inducing cell penetration within 30%, 40%, 50%, 60%, 70%, 80%, 90%, or 100% of cells of a given cell culture population, including all integers in between, and allow macromolecular translocation within multiple tissues in vivo upon systemic administration.

The terms "antisense oligomer" or "antisense compound" or "antisense oligonucleotide" or "oligonucleotide" are used interchangeably and refer to a sequence of cyclic subunits, each bearing a base-pairing moiety, linked by intersubunit linkages that allow the base-pairing moieties to hybridize to a target sequence in a nucleic acid (typically an RNA) by Watson-Crick base pairing, to form a nucleic acid:oligomer heteroduplex within the target sequence. The cyclic subunits may be based on ribose or another pentose sugar or, in certain embodiments, a morpholino group (see description of morpholino oligomers below). Also contemplated are peptide nucleic acids (PNAs), locked nucleic acids (LNAs), and 2'-O-Methyl oligonucleotides, and other antisense agents known in the art.

Such an antisense oligomer can be designed to block or inhibit translation of mRNA or to inhibit natural pre-mRNA splice processing, or induce degradation of targeted mRNAs, and may be said to be "directed to" or "targeted against" a target sequence with which it hybridizes. In certain embodiments, the target sequence is a region surrounding or including an AUG start codon of an mRNA, a 3' or 5' splice site of a pre-processed mRNA, or a branch point. The target sequence may be within an exon or within an intron or a combination thereof. The target sequence for a splice site may include an mRNA sequence having its 5' end at 1 to about 25 base pairs downstream of a normal splice acceptor junction in a preprocessed mRNA. An exemplary target sequence for a splice site is any region of a preprocessed mRNA that includes a splice site or is contained entirely within an exon coding sequence or spans a splice acceptor or donor site. An oligomer is more generally said to be "targeted against" a biologically relevant target such as, in the present disclosure, a human LMNA gene pre-mRNA encoding the lamin A protein, when it is targeted against the nucleic acid of the target in the manner described above. Exemplary targeting sequences include SEQ ID NOS: 3 or 4

Included are antisense oligonucleotides that comprise, consist essentially of, or consist of one or more of SEQ ID NOS: 3 or 4. Also included are variants of these antisense oligomers, including variant oligomers having 80%, 85%, 90%, 95%, 97%, 98%, or 99% (including all integers in between) sequence identity or sequence homology to any one of SEQ ID NOS:3 or 4, and/or variants that differ from these sequences by about 1, 2, 3, 4, 5, 6, 7, 8, 9, or 10 nucleotides, preferably those variants that modulate progerin expression in a cell. Also included are oligonucleotides of any one or more of SEQ ID NOS: 3 or 4, which comprise a suitable number of cationic or other modified linkages, as described herein, e.g., up to about 1 per every 2-5 uncharged linkages, such as about 4-5 per every 10 uncharged linkages, and/or which comprise a cell-penetrating transport peptide attached thereto, as also described herein.

"PMO+" refers to phosphorodiamidate morpholino oligomers comprising any number of (1-piperazino)phosphinylideneoxy, (1-(4-(ω-guanidino-alkanoyl))-piperazino) phosphinylideneoxy linkages (A2 and A3) that have been described previously (see e.g., PCT publication WO2008/036127 which is incorporated herein by reference in its entirety).

"PMO-X" refers to phosphorodiamidate morpholino oligomers disclosed herein comprising at least one (B) linkage or at least one of the disclosed terminal modifications, and as disclosed in PCT Publication WO2011/150408 and U.S. Patent Publication US2012/0065169, which are incorporated herein by reference in their entireties. Further PMO-X phosphorodiamidate morpholino oligomers useful herein may be found in U.S. Provisional Application No. 61/561,806, filed Nov. 18, 2011, which is incorporated herein by reference in its entirety.

A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the modified intersubunit linkages of the oligomers described herein and U.S. Provisional Application No. 61/349,783 and U.S. patent application Ser. No. 11/801,885, one nitrogen is always pendant to the backbone chain. The second nitrogen, in a phosphorodiamidate linkage, is typically the ring nitrogen in a morpholino ring structure.

"Thiophosphoramidate" or "thiophosphorodiamidate" linkages are phosphoramidate or phosphorodiamidate linkages, respectively, wherein one oxygen atom, typically the oxygen pendant to the backbone, is replaced with sulfur.

"Intersubunit linkage" refers to the linkage connecting two morpholino subunits, for example structure (I).

"Charged", "uncharged", "cationic" and "anionic" as used herein refer to the predominant state of a chemical moiety at near-neutral pH, e.g., about 6 to 8. For example, the term may refer to the predominant state of the chemical moiety at physiological pH, that is, about 7.4.

As used herein, an "antisense oligonucleotide," "antisense oligomer" or "oligonucleotide" refers to a linear sequence of nucleotides, or nucleotide analogs, which allows the nucleobase to hybridize to a target sequence in an RNA by Watson-Crick base pairing, to form an oligomer:RNA heteroduplex within the target sequence. The terms "antisense oligonucleotide", "modified antisense oligonucleotide", "antisense oligomer", "oligomer" and "compound" may be used interchangeably to refer to an oligomer. The cyclic subunits may be based on ribose or another pentose sugar or, in certain embodiments, a morpholino group (see description of morpholino oligomers below).

The term "oligonucleotide analog" refers to an oligonucleotide having (i) a modified backbone structure, e.g., a backbone other than the standard phosphodiester linkage found in natural oligo- and polynucleotides, and (ii) optionally, modified sugar moieties, e.g., morpholino moieties rather than ribose or deoxyribose moieties. Oligonucleotide analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Exemplary analogs are those having a substantially uncharged, phosphorus containing backbone.

A substantially uncharged, phosphorus containing backbone in an oligonucleotide analog is one in which a majority of the subunit linkages, e.g., between 50-100%, typically at least 60% to 100% or 75% or 80% of its linkages, are uncharged, and contain a single phosphorous atom. Antisense oligonucleotides and oligonucleotide analogs may contain between about 8 and 40 subunits, typically about 8-25 subunits, and preferably about 12 to 25 subunits (including all integers and ranges in between). In certain embodiments, oligonucleotides may have exact sequence complementarity to the target sequence or near complementarity, as defined below.

A "subunit" of an oligonucleotide refers to one nucleotide (or nucleotide analog) unit comprising a purine or pyrimidine base pairing moiety. The term may refer to the nucleotide unit with or without the attached intersubunit linkage, although, when referring to a "charged subunit", the charge typically resides within the intersubunit linkage (e.g., a phosphate or phosphorothioate linkage or a cationic linkage).

The purine or pyrimidine base pairing moiety, also referred to herein simply as a "nucleobases," "base," or "bases," may be adenine, cytosine, guanine, uracil, thymine or inosine. Also included are bases such as pyridin-4-one, pyridin-2-one, phenyl, pseudouracil, 2,4,6-trime115thoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetyltidine, 5-(carboxyhydroxymethyl)uridine, 5'-carboxymethylaminomethyl-2-thiouridine, 5-carboxymethylaminomethyluridine, β-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonyhnethyluridine, 5-methyloxyuridine, 5-methyl-2-thiouridine, 2-methylthio-N6-isopentenyladenosine, β-D-mannosylqueosine, uridine-5-oxyacetic acid, 2-thiocytidine, threonine derivatives and others (Burgin et al., 1996, Biochemistry, 35:14090; Uhlman & Peyman, supra). By "modified bases" in this aspect is meant nucleotide bases other than adenine (A), guanine (G), cytosine (C), thymine (T), and uracil (U), as illustrated above; such bases can be used at any position in the antisense molecule. Persons skilled in the art will appreciate that depending on the uses of the oligomers, Ts and Us are interchangeable. For instance, with other antisense chemistries such as 2'-O-methyl antisense oligonucleotides that are more RNA-like, the T bases may be shown as U.

The term "targeting sequence" is the sequence in the oligomer or oligomer analog that is complementary (meaning, in addition, substantially complementary) to the "target sequence" in the RNA genome. The entire sequence, or only a portion, of the antisense oligomer may be complementary to the target sequence. For example, in an oligomer having 20-30 bases, about 6, 7, 8, 9, 10, 11, 12, 13, 14, 15, 16, 17, 18, 19, 20, 21, 22, 23, 24, 25, 26, 27, 28, or 29 may be targeting sequences that are complementary to the target region. Typically, the targeting sequence is formed of contiguous bases in the oligomer, but may alternatively be formed of non-contiguous sequences that when placed together, e.g., from opposite ends of the oligomer, constitute sequence that spans the target sequence.

A "targeting sequence" may have "near" or "substantial" complementarity to the target sequence and still function for the purpose of the present disclosure, that is, still be "complementary." Preferably, the oligomer analog compounds employed in the present disclosure have at most one mismatch with the target sequence out of 10 nucleotides, and preferably at most one mismatch out of 20. Alternatively, the antisense oligomers employed have at least 90% sequence identity, and preferably at least 95% sequence identity, with the exemplary targeting sequences as designated herein.

As used herein, the terms "TEG," "EG3," or "triethylene glycol tail" refer to triethylene glycol moieties conjugated to the oligonucleotide, e.g., at its 3'- or 5'-end. For example, in some embodiments, "TEG" includes a moiety of the formula:

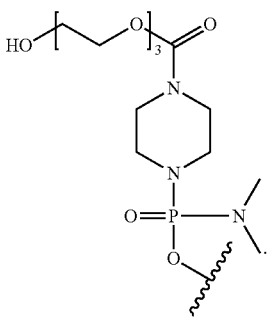

An "amino acid subunit" or "amino acid residue" can refer to an α-amino acid residue (—CO—CHR—NH—) or a β- or other amino acid residue (e.g., —CO—(CH$_2$)$_n$CHR—NH—), where R is a side chain (which may include hydrogen) and n is 1 to 7, preferably 1 to 4.

The term "naturally occurring amino acid" refers to an amino acid present in proteins found in nature, such as the 20 (L)-amino acids utilized during protein biosynthesis as well as others such as 4-hydroxyproline, hydroxylysine, desmosine, isodesmosine, homocysteine, citrulline and ornithine. The term "non-natural amino acids" refers to those amino acids not present in proteins found in nature, examples include beta-alanine (β-Ala), 6-aminohexanoic acid (Ahx) and 6-aminopentanoic acid. Additional examples of "non-natural amino acids" include, without limitation, (D)-amino acids, norleucine, norvaline, p-fluorophenylalanine, ethionine and the like, which are known to a person skilled in the art.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect (e.g., sensitization of a cancer cell to a chemotherapeutic) For an antisense oligomer, this effect is typically brought about by inhibiting translation or natural splice-processing of a selected target sequence. An "effective amount," targeted against LMNA mRNA, also relates to an amount effective to modulate expression of progerin.

By "enhance" or "enhancing," or "increase" or "increasing," or "stimulate" or "stimulating," refers generally to the ability of one or antisense compounds or compositions to produce or cause a greater physiological response (i.e., downstream effects) in a cell, as compared to the response caused by either no antisense compound or a control compound. An "increased" or "enhanced" amount is typically a "statistically significant" amount, and may include an increase that is 1.1, 1.2, 2, 3, 4, 5, 6, 7, 8, 9, 10, 15, 20, 30, 40, 50 or more times (e.g., 500, 1000 times) (including all integers and decimal points in between and above 1), e.g., 1.5, 1.6, 1.7, 1.8, etc.) the amount produced by no antisense compound (the absence of an agent) or a control compound.

The term "reduce" or "inhibit" may relate generally to the ability of one or more antisense compounds of the disclosure to "decrease" a relevant physiological or cellular response, as measured according to routine techniques in the diagnostic art. Relevant physiological or cellular responses (in vivo or in vitro) will be apparent to persons skilled in the art, and may include, for example, reductions in expression of progerin as measured by mRNA and/or protein levels. A "decrease" in a response may be "statistically significant" as compared to the response produced by no antisense compound or a control composition, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease, including all integers in between.

The term "target sequence" refers to a portion of the target RNA against which the oligonucleotide or antisense agent is directed, that is, the sequence to which the oligonucleotide will hybridize by Watson-Crick base pairing of a complementary sequence. In certain embodiments, the target sequence may be a contiguous region of a pre-mRNA that includes both intron and exon target sequence. In certain other embodiments, the target sequence will consist exclusively of either intron or exon sequences.

The term "targeting sequence" or "antisense targeting sequence" refers to the sequence in an oligonucleotide or other antisense agent that is complementary (meaning, in addition, substantially complementary) to the target sequence in the RNA genome. The entire sequence, or only a portion, of the antisense compound may be complementary to the target sequence. For example, in an oligonucleotide having 20-30 bases, about 6, 7, 8, 9, 10, 11, 12, 13, 14, 15, 16, 17, 18, 19, 20, 21, 22, 23, 24, 25, 26, 27, 28, or 29 bases may be targeting sequences that are complementary to the target region. Typically, the targeting sequence is formed of contiguous bases, but may alternatively be formed of non-contiguous sequences that when placed together, e.g., from opposite ends of the oligonucleotide, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the present disclosure, that is, it may still be functionally "complementary." In certain embodiments, an oligonucleotide may have at most one mismatch with the target sequence out of 10 nucleotides, and preferably at most one mismatch out of 20. Alternatively, an oligonucleotide may have at least 90% sequence identity, and preferably at least 95% sequence identity, with the exemplary antisense targeting sequences described herein.

An oligonucleotide "specifically hybridizes" to a target polynucleotide if the oligomer hybridizes to the target under physiological conditions, with a Tm substantially greater than 45° C., preferably at least 50° C., and typically 60° C.-80° C. or higher. Such hybridization preferably corresponds to stringent hybridization conditions. At a given ionic strength and pH, the Tm is the temperature at which 50% of a target sequence hybridizes to a complementary polynucleotide. Again, such hybridization may occur with "near" or "substantial" complementarity of the antisense oligomer to the target sequence, as well as with exact complementarity.

"Homology" refers to the percentage number of amino acids that are identical or constitute conservative substitutions. Homology may be determined using sequence comparison programs such as GAP (Deveraux et al., 1984, *Nucleic Acids Research* 12, 387-395). In this way sequences of a similar or substantially different length to those cited herein could be compared by insertion of gaps into the alignment, such gaps being determined, for example, by the comparison algorithm used by GAP.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

Terms used to describe sequence relationships between two or more polynucleotides or polypeptides include "reference sequence," "comparison window," "sequence identity," "percentage of sequence identity," and "substantial identity". A "reference sequence" is at least 8 or 10 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences.

Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., "Current Protocols in Molecular Biology," John Wiley & Sons Inc, 1994-1998, Chapter 15.

A "nuclease-resistant" oligomeric molecule (oligomer) refers to one whose backbone is substantially resistant to nuclease cleavage, in non-hybridized or hybridized form; by common extracellular and intracellular nucleases in the body; that is, the oligomer shows little or no nuclease cleavage under normal nuclease conditions in the body to which the oligomer is exposed.

An agent is "actively taken up by mammalian cells" when the agent can enter the cell by a mechanism other than passive diffusion across the cell membrane. The agent may be transported, for example, by "active transport," referring to transport of agents across a mammalian cell membrane by e.g., an ATP-dependent transport mechanism, or by "facilitated transport," referring to transport of antisense agents across the cell membrane by a transport mechanism that requires binding of the agent to a transport protein, which then facilitates passage of the bound agent across the membrane. For both active and facilitated transport, oligonucleotide analogs preferably have a substantially uncharged backbone, as defined below.

A "heteroduplex" refers to a duplex between an antisense oligonucleotide and the complementary portion of a target RNA. A "nuclease-resistant heteroduplex" refers to a heteroduplex formed by the binding of an antisense oligomer to its complementary target, such that the heteroduplex is substantially resistant to in vivo degradation by intracellular and extracellular nucleases, such as RNaseH, which are capable of cutting double-stranded RNA/RNA or RNA/DNA complexes.

As used herein, the term "body fluid" encompasses a variety of sample types obtained from a subject including, urine, saliva, plasma, blood, spinal fluid, or other sample of biological origin, such as skin cells or dermal debris, and may refer to cells or cell fragments suspended therein, or the liquid medium and its solutes.

The term "relative amount" is used where a comparison is made between a test measurement and a control measurement. The relative amount of a reagent forming a complex in a reaction is the amount reacting with a test specimen, compared with the amount reacting with a control specimen. The control specimen may be run separately in the same assay, or it may be part of the same sample (for example, normal tissue surrounding a malignant area in a tissue section).

"Treatment" of an individual or a cell is any type of intervention provided as a means to alter the natural course of a disease or pathology in the individual or cell. Treatment includes, but is not limited to, administration of, e.g., a pharmaceutical composition, and may be performed either prophylactically, or subsequent to the initiation of a pathologic event or contact with an etiologic agent. Treatment includes any desirable effect on the symptoms or pathology of a disease or condition associated with inflammation, among others described herein.

Also included are "prophylactic" treatments, which can be directed to reducing the rate of progression of the disease or condition being treated, delaying the onset of that disease or condition, or reducing the severity of its onset. "Treatment" or "prophylaxis" does not necessarily indicate complete eradication, cure, or prevention of the disease or condition, or associated symptoms thereof.

A wild-type gene or gene product is that which is most frequently observed in a population and is thus arbitrarily designed the "normal" or "wild-type" form of the gene.

LMNA Targeting

Examples include antisense oligonucleotides that target SEQ ID NOs: 1 and/or 2, discussed below.

Certain antisense oligonucleotides may comprise a targeting sequence that is complementary to one or more bases of exon 11 in the human LMNA gene including the wild-type sequence (SEQ ID NO: 1) and/or the sequence found in HGPS patients, as shown in SEQ ID NO: 2. These target sequences are shown in Table 1 below:

TABLE 1

Exemplary LMNA Target Sequences

| NAME | SEQUENCE | SEQ ID NO: |
|---|---|---|
| LMNA exon 11 | GGCTCCCACTGCAGCAGCTCGGGGGACCCCGCTGA GTACAACCTGCGCTCGCGCACCGTGCTGTGCGGGA CCTGCGGGCAGCCTGCCGACAAGGCATCTGCCAGC GGCTCAGGAGCC<u>CAGGTGGGC</u>GGACCCATCTCCTC TGGCTCTTCTGCCTCCAGTGTCACGGTCACTCGCA GCTACCGCAGTGTGGGGGCAGTGGGGGTGGCAGC TTCGGGGACAATCTGGTCACCCGCTCCTACCTCCT GGGCAACTCCAGCCCCCGAACCCAG | 1 |
| HGPS exon 11 | GGCTCCCACTGCAGCAGCTCGGGGGACCCCGCTGA GTACAACCTGCGCTCGCGCACCGTGCTGTGCGGGA CCTGCGGGCAGCCTGCCGACAAGGCATCTGCCAGC GGCTCAGGAGCC<u>CAGGTGGGT</u>GGACCCATCTCCTC TGGCTCTTCTGCCTCCAGTGTCACGGTCACTCGCA GCTACCGCAGTGTGGGGGCAGTGGGGGTGGCAGC TTCGGGGACAATCTGGTCACCCGCTCCTACCTCCT GGGCAACTCCAGCCCCCGAACCCAG | 2 |

Examples include antisense oligonucleotides that are fully complementary to LMNA exon 11 (SEQ ID NO: 1 or 2) including those that are also complementary to the cryptic splice site of LMNA exon 11 underlined in SEQ ID NO:1 and 2 in Table 1.

(e.g., <u>CAGGTGGGC/T</u>).

In certain embodiments, the degree of complementarity between the target and antisense targeting sequence is sufficient to form a stable duplex. The region of complementarity of the antisense oligomers with the target RNA sequence may be as short as 8-11 bases, but is preferably 12-15 bases or more, e.g., 12-20 bases, 12-25, or 15-25 bases, including all integers and ranges in between these ranges. An antisense oligomer of about 14-15 bases is generally long enough to have a unique complementary sequence in the target mRNA. In certain embodiments, a minimum length of complementary bases may be required to achieve the requisite binding Tm, as discussed below.

In certain embodiments, oligomers as long as 40 bases may be suitable, where at least a minimum number of bases, e.g., 10-12 bases, are complementary to the target sequence. In general, however, facilitated or active uptake in cells is optimized at oligomer lengths less than about 30. For PMO oligomers, described further below, an optimum balance of binding stability and uptake generally occurs at lengths of 18-30 bases. Included are antisense oligomers (e.g., PNAs, LNAs, 2'-OMe, MOE, PMOs) that consist of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases, in which at least about 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous and/or non-contiguous bases are complementary to a target sequence described herein, including the target sequences of SEQ ID NOs: 1 and/or 2, or variants thereof.

In certain embodiments, antisense oligomers may be 100% complementary to the LMNA pre-mRNA nucleic acid target sequence, or they may include mismatches, e.g., to accommodate variants, as long as a heteroduplex formed between the oligomer and the target sequence is sufficiently stable to withstand the action of cellular nucleases and other modes of degradation or displacement which may occur in vivo. Oligomer backbones which are less susceptible to cleavage by nucleases are discussed below. Mismatches, if present, are less destabilizing toward the end regions of the hybrid duplex than in the middle. The number of mismatches allowed will depend on the length of the oligomer, the percentage of G:C base pairs in the duplex, and the position of the mismatch(es) in the duplex, according to well understood principles of duplex stability. Although such an antisense oligomer is not necessarily 100% complementary to the target sequence, it is effective to stably and specifically bind to the target sequence, such that a biological activity of the nucleic acid target, e.g., expression of the progerin protein(s), is modulated.

In certain embodiments, such as PMO oligomers, the antisense activity of an oligomer may be enhanced by using a mixture of uncharged and cationic phosphorodiamidate linkages. The total number of cationic linkages in the oligomer can vary from 1 to 10 (including all integers in between), and be interspersed throughout the oligomer. Preferably the number of charged linkages is at least 2 and no more than half the total backbone linkages, e.g., between 2, 3, 4, 5, 6, 7, or 8 positively charged linkages, and preferably each charged linkage is separated along the backbone by at least 1, 2, 3, 4, or 5 uncharged linkages.

Exemplary antisense sequences for targeting the human LMNA pre-mRNA are shown in Table 2 below. Antisense oligonucleotides can comprise all or a portion of these targeting sequences.

TABLE 2

Exemplary HGPS Targeting Sequences*

| Sequence name | Targeting Sequence 5'-3' | SEQ ID NO: |
|---|---|---|
| Ex11-1 | CTGAGCCGCTGGCAGATGCCTTGTC | 3 |
| Ex11-2 | GAGGAGATGGGTCCACCCACCTGGG | 4 |

Antisense Oligonucleotide Compounds

The antisense oligonucleotides of the present disclosure typically (a) have the ability to be actively taken up by mammalian cells, and (b) once taken up, form a duplex with the target RNA with a Tm greater than about 45° C. In certain embodiments, the oligomer backbone may be substantially uncharged, and, preferably, may be recognized as a substrate for active or facilitated transport across the cell membrane. The ability of the oligomer to form a stable duplex with the target RNA may also relate to other features of the oligomer backbone, including the length and degree of complementarity of the antisense oligomer with respect to the target, the ratio of G:C to A:T base matches, and the positions of any mismatched bases. The ability of the antisense oligomer to resist cellular nucleases may promote survival and ultimate delivery of the agent to the cell cytoplasm.

The antisense oligomers can employ a variety of antisense chemistries. Examples of oligomer chemistries include, without limitation, phosphoramidate morpholino oligomers and phosphorodiamidate morpholino oligomers (PMO), phosphorothioate modified oligomers, 2' O-methyl modified oligomers, peptide nucleic acid (PNA), locked nucleic acid (LNA), phosphorothioate oligomers, 2' O-MOE modified oligomers, 2'-fluoro-modified oligomer, 2'O,4'C-ethylene-bridged nucleic acids (ENAs), tricyclo-DNAs, tricyclo-DNA phosphorothioate nucleotides, 2'-O-[2-(N-methylcarbamoyl)ethyl] modified oligomers, morpholino oligomers, peptide-conjugated phosphoramidate morpholino oligomers (PPMO), phosphorodiamidate morpholino oligomers having a phosphorous atom with (i) a covalent bonds to the nitrogen atom of a morpholino ring, and (ii) a second covalent bond to a (1,4-piperazin)-1-yl substituent or to a substituted (1,4-piperazin)-1-yl (PMOplus), and phosphorodiamidate morpholino oligomers having a phosphorus atom with (i) a covalent bond to the nitrogen atom of a morpholino ring and (ii) a second covalent bond to the ring nitrogen of a 4-aminopiperdin-1-yl (i.e., APN) or a derivative of 4-aminopiperdin-1-yl (PMO-X) chemistries, including combinations of any of the foregoing. In general, PNA and LNA chemistries can utilize shorter targeting sequences because of their relatively high target binding strength relative to PMO and 2'O-Me modified oligomers. Phosphorothioate and 2'O-Me-modified chemistries can be combined to generate a 2'O-Me-phosphorothioate backbone. See, e.g., PCT Publication Nos. WO2013/112053 and WO2009/008725, which are hereby incorporated by reference in their entireties.

In some instances, antisense oligomers such as PMOs can be conjugated to cell penetrating peptides (CPPs) to facilitate intracellular delivery. Peptide-conjugated PMOs are called PPMOs and certain embodiments include those described in PCT Publication No. WO2012/150960, incorporated herein by reference in its entirety. In some embodiments, an arginine-rich peptide sequence conjugated or linked to, for example, the 3' terminal end of an antisense oligomer as described herein may be used. In certain embodiments, an arginine-rich peptide sequence conjugated or linked to, for example, the 5' terminal end of an antisense oligomer as described herein may be used.

1. Peptide Nucleic Acids (PNAs)

Peptide nucleic acids (PNAs) are analogs of DNA in which the backbone is structurally homomorphous with a deoxyribose backbone, consisting of N-(2-aminoethyl) glycine units to which pyrimidine or purine bases are attached. PNAs containing natural pyrimidine and purine bases hybridize to complementary oligomers obeying Watson-Crick base-pairing rules, and mimic DNA in terms of base pair recognition (Egholm, Buchardt et al. 1993). The backbone of PNAs is formed by peptide bonds rather than phosphodiester bonds, making them well-suited for antisense applications (see structure below). The backbone is uncharged, resulting in PNA/DNA or PNA/RNA duplexes that exhibit greater than normal thermal stability. PNAs are not recognized by nucleases or proteases. A non-limiting example of a PNA is depicted below:

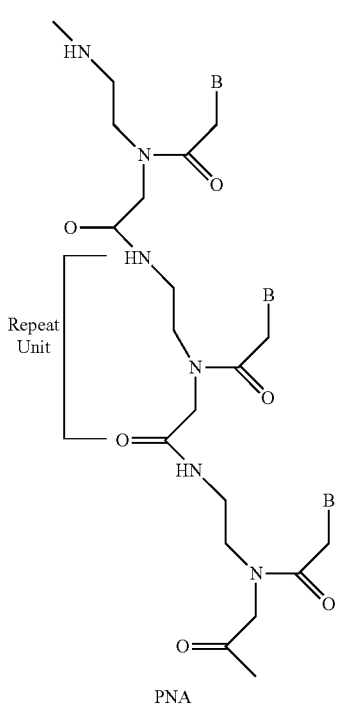

PNA

Despite a radical structural change to the natural structure, PNAs are capable of sequence-specific binding in a helix form to DNA or RNA. Characteristics of PNAs include a high binding affinity to complementary DNA or RNA, a destabilizing effect caused by single-base mismatch, resistance to nucleases and proteases, hybridization with DNA or RNA independent of salt concentration and triplex formation with homopurine DNA. PANAGENE™ has developed its proprietary Bts PNA monomers (Bts; benzothiazole-2-sulfonyl group) and proprietary oligomerization process. The PNA oligomerization using Bts PNA monomers is composed of repetitive cycles of deprotection, coupling and capping. PNAs can be produced synthetically using any technique known in the art. See, e.g., U.S. Pat. Nos. 6,969,766, 7,211,668, 7,022,851, 7,125,994, 7,145,006 and 7,179,896. See also U.S. Pat. Nos. 5,539,082; 5,714,331; and 5,719,262 for the preparation of PNAs. Further teaching of PNA compounds can be found in Nielsen et al., Science, 254:1497-1500, 1991. Each of the foregoing is incorporated by reference in its entirety.

2. Locked Nucleic Acids (LNAs)

Antisense oligomer compounds may also contain "locked nucleic acid" subunits (LNAs). "LNAs" are a member of a class of modifications called bridged nucleic acid (BNA). BNA is characterized by a covalent linkage that locks the conformation of the ribose ring in a C30-endo (northern) sugar pucker. For LNA, the bridge is composed of a methylene between the 2'-O and the 4'-C positions. LNA enhances backbone preorganization and base stacking to increase hybridization and thermal stability.

The structures of LNAs can be found, for example, in Wengel, et al., Chemical Communications (1998) 455; Tetrahedron (1998) 54:3607, and Accounts of Chem. Research (1999) 32:301); Obika, et al., Tetrahedron Letters (1997) 38:8735; (1998) 39:5401, and Bioorganic Medicinal Chemistry (2008) 16:9230, which are hereby incorporated by reference in their entirety. A non-limiting example of an LNA is depicted below:

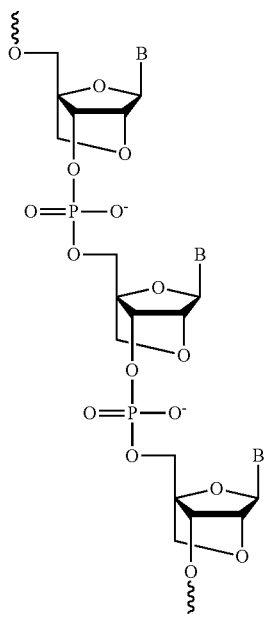

LNA

Compounds of the disclosure may incorporate one or more LNAs; in some cases, the compounds may be entirely composed of LNAs. Methods for the synthesis of individual LNA nucleoside subunits and their incorporation into oligomers are described, for example, in U.S. Pat. Nos. 7,572,582, 7,569,575, 7,084,125, 7,060,809, 7,053,207, 7,034,133, 6,794,499, and 6,670,461, each of which is incorporated by reference in its entirety. Typical intersubunit linkers include phosphodiester and phosphorothioate moieties; alternatively, non-phosphorous containing linkers may be employed. Further embodiments include an LNA containing compound where each LNA subunit is separated by a DNA subunit. Certain compounds are composed of alternating LNA and DNA subunits where the intersubunit linker is phosphorothioate.

2'O,4'C-ethylene-bridged nucleic acids (ENAs) are another member of the class of BNAs. A non-limiting example is depicted below:

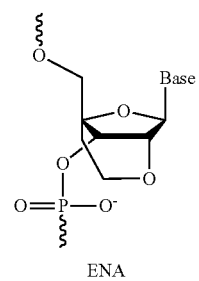

ENA

ENA oligomers and their preparation are described in Obika et al., Tetrahedron Lett 38 (50): 8735, which is hereby incorporated by reference in its entirety. Compounds of the disclosure may incorporate one or more ENA subunits.

3. Phosphorothioates

"Phosphorothioates" (or S-oligos) are a variant of normal DNA in which one of the nonbridging oxygens is replaced by a sulfur. A non-limiting example of a phosphorothioate is depicted below:

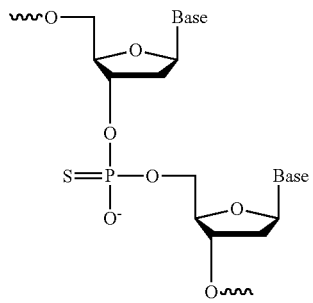

The sulfurization of the internucleotide bond reduces the action of endo- and exonucleases including 5' to 3' and 3' to 5' DNA POL 1 exonuclease, nucleases S1 and P1, RNases, serum nucleases and snake venom phosphodiesterase. Phosphorothioates are made by two principal routes: by the action of a solution of elemental sulfur in carbon disulfide on a hydrogen phosphonate, or by the method of sulfurizing phosphite triesters with either tetraethylthiuram disulfide (TETD) or 3H-1, 2-bensodithiol-3-one 1, 1-dioxide (BDTD) (see, e.g., Iyer et al., J. Org. Chem. 55, 4693-4699, 1990, which are hereby incorporated by reference in their entirety). The latter methods avoid the problem of elemental sulfur's insolubility in most organic solvents and the toxicity of carbon disulfide. The TETD and BDTD methods also yield higher purity phosphorothioates.

4. Tricyclo-DNAs and Tricyclo-Phosphorothioate Nucleotides

Tricyclo-DNAs (tc-DNA) are a class of constrained DNA analogs in which each nucleotide is modified by the introduction of a cyclopropane ring to restrict conformational flexibility of the backbone and to optimize the backbone geometry of the torsion angle γ. Homobasic adenine- and thymine-containing tc-DNAs form extraordinarily stable A-T base pairs with complementary RNAs. Tricyclo-DNAs and their synthesis are described in PCT Patent Application Publication No. WO 2010/115993, which is hereby incorporated by reference in its entirety. Compounds of the disclosure may incorporate one or more tricycle-DNA nucleotides; in some cases, the compounds may be entirely composed of tricycle-DNA nucleotides.

Tricyclo-phosphorothioate nucleotides are tricyclo-DNA nucleotides with phosphorothioate intersubunit linkages. Tricyclo-phosphorothioate nucleotides and their synthesis are described in PCT Patent Application Publication No. WO 2013/053928, which is hereby incorporated by reference in its entirety. Compounds of the disclosure may incorporate one or more tricycle-DNA nucleotides; in some cases, the compounds may be entirely composed of tricycle-DNA nucleotides. A non-limiting example of a tricyclo-DNA/tricyclo-phosphorothioate nucleotide is depicted below:

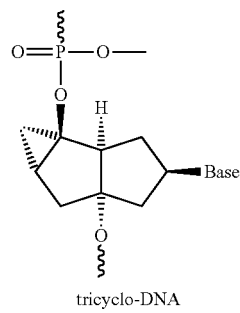

tricyclo-DNA

5. 2' O-Methyl, 2' O-MOE, and 2'-F Oligomers

"2'O-Me oligomer" molecules carry a methyl group at the 2'-OH residue of the ribose molecule. 2'-O-Me-RNAs show the same (or similar) behavior as DNA, but are protected against nuclease degradation. 2'-O-Me-RNAs can also be combined with phosphothioate oligomers (PTOs) for further stabilization. 2'O-Me oligomers (phosphodiester or phosphothioate) can be synthesized according to routine techniques in the art (see, e.g., Yoo et al., Nucleic Acids Res. 32:2008-16, 2004, which is hereby incorporated by reference in its entirety). A non-limiting example of a 2' O-Me oligomer is depicted below:

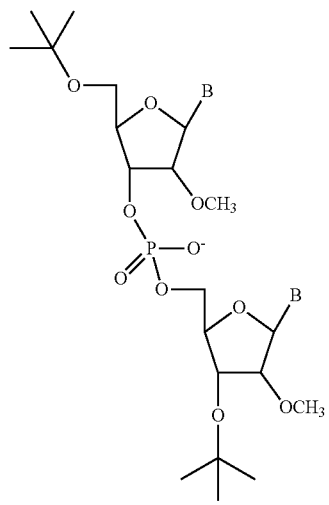

2' O-Me oligomers may also comprise a phosphorothioate linkage (2' O-Me phosphorothioate oligomers). 2' O-Methoxyethyl Oligomers (2'-O MOE), like 2' O-Me oligomers, carry a methoxyethyl group at the 2'-OH residue of the ribose molecule and are discussed in Martin et al. Helv. Chim. Acta, 78, 486-504, 1995, which is hereby incorporated by reference in its entirety. A non-limiting example of a 2' O-MOE nucleotide is depicted below:

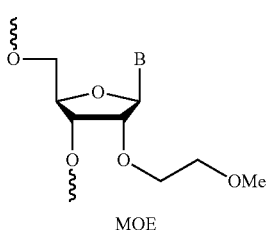

MOE

In contrast to the preceding alkylated 2'OH ribose derivatives, 2'-fluoro oligomers have a fluoro radical in at the 2' position in place of the 2'OH. A non-limiting example of a 2'-F oligomer is depicted below:

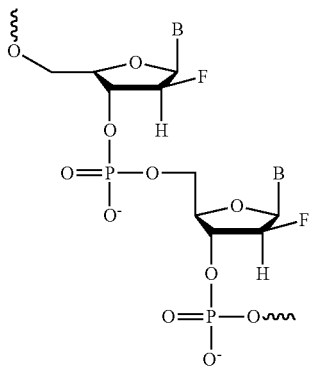

2'-fluoro oligomers are further described in PCT Application Publication No. WO 2004/043977, which is hereby incorporated by reference in its entirety. Compounds of the disclosure may incorporate one or more 2'O-Methyl, 2' O-MOE, and 2'-F subunits and may utilize any of the intersubunit linkages described here. In some instances, a compound of the disclosure could be composed of entirely 2'O-Methyl, 2' O-MOE, or 2'-F subunits. One embodiment of a compound of the disclosure is composed entirely of 2'O-methyl subunits.

6. 2'-O-[2-(N-methylcarbamoyl)ethyl] Oligonucleotides (MCEs)

MCEs are another example of 2'O modified ribonucleosides useful in the compounds of the disclosure. Here, the 2'OH is derivatized to a 2-(N-methylcarbamoyl)ethyl moiety to increase nuclease resistance. A non-limiting example of an MCE oligomer is depicted below:

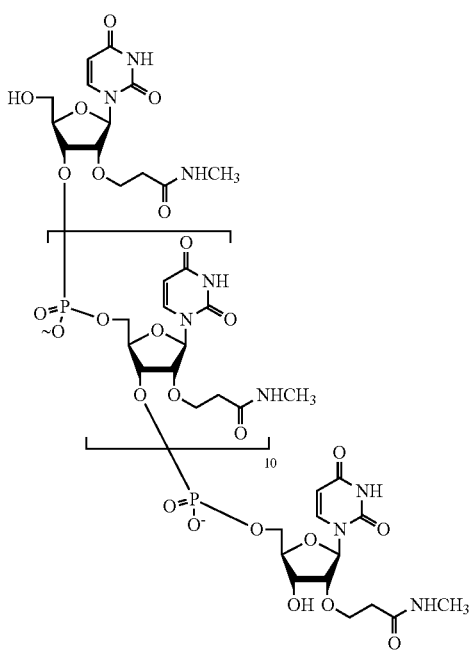

MCEs and their synthesis are described in Yamada et al., *J. Org. Chem.*, 76(9):3042-53, which is hereby incorporated by reference in its entirety. Compounds of the disclosure may incorporate one or more MCE subunits.

7. Stereo Specific Oligomers

Stereo specific oligomers are those which the stereo chemistry of each phosphorous-containing linkage is fix by the method of synthesis such that a substantially pure single oligomer is produced. A non-limiting example of a stereo specific oligomer is depicted below:

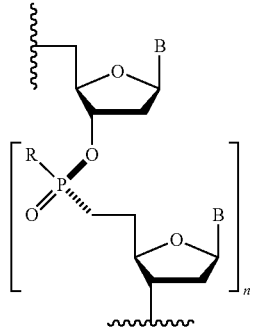

In the above example, each phosphorous of the oligomer has the same stereo chemistry. Additional examples include the oligomers described above. For example, LNAs, ENAs, Tricyclo-DNAs, MCEs, 2' O-Methyl, 2' O-MOE, 2'-F, and morpholino-based oligomers can be prepared with stereospecific phosphorous-containing internucleoside linkages such as, for example, phosphorothioate, phosphodiester, phosphoramidate, phosphorodiamidate, or other phosphorous-containing internucleoside linkages. Stereo specific oligomers, methods of preparation, chirol controlled synthesis, chiral design, and chiral auxiliaries for use in preparation of such oligomers are detailed, for example, in PCT Application Publication Nos. WO2015/107425, WO2015/108048, WO2015/108046, WO2015/108047, WO2012/039448, WO2010/064146, WO2011/034072, WO2014/010250, WO2014/012081, WO2013/0127858, and WO2011/005761, each of which is hereby incorporated by reference in its entirety.

8. Morpholino-Based Oligomers

Morpholino-based oligomers refer to an oligomer comprising morpholino subunits supporting a nucleobase and, instead of a ribose, contains a morpholine ring. Exemplary internucleoside linkages include, for example, phosphoramidate or phosphorodiamidate internucleoside linkages joining the morpholine ring nitrogen of one morpholino subunit to the 4' exocyclic carbon of an adjacent morpholino subunit. Each morpholino subunit comprises a purine or pyrimidine nucleobase effective to bind, by base-specific hydrogen bonding, to a base in an oligonucleotide.

Morpholino-based oligomers (including antisense oligomers) and their synthesis are detailed, for example, in U.S. Pat. Nos. 5,698,685; 5,217,866; 5,142,047; 5,034,506; 5,166,315; 5,185,444; 5,521,063; 5,506,337 and U.S. patent application Ser. Nos. 12/271,036; 12/271,040; and PCT Publication No. WO2009/064471 and WO2012/043730 and Summerton et al. 1997, Antisense and Nucleic Acid Drug Development, 7:187-195, which are hereby incorporated by reference in their entirety. Within the oligomer structure, the phosphate groups are commonly referred to as forming the "internucleoside linkages" of the oligomer. The naturally occurring internucleoside linkage of RNA and DNA is a 3' to 5' phosphodiester linkage. A "phosphoramidate" group comprises phosphorus having three attached oxygen atoms and one attached nitrogen atom, while a "phosphorodiamidate" group comprises phosphorus having two attached oxygen atoms and two attached nitrogen atoms. In the uncharged or the cationic intersubunit linkages of morpholino-based oligomers described herein, one nitrogen is always pendant to the backbone chain. The second nitrogen, in a phosphorodiamidate linkage, is typically the ring nitrogen in a morpholine ring structure.

"PMO-X" refers to phosphorodiamidate morpholino-based oligomers having a phosphorus atom with (i) a covalent bond to the nitrogen atom of a morpholine ring and (ii) a second covalent bond to the ring nitrogen of a 4-aminopiperdin-1-yl (i.e., APN) or a derivative of 4-aminopiperdin-1-yl. Exemplary PMO-X oligomers are disclosed in PCT Application No. PCT/US2011/38459 and PCT Publication No. WO 2013/074834, which are hereby incorporated by reference in their entirety. PMO-X includes "PMO-apn" or "APN," which refers to a PMO-X oligomer which comprises at least one internucleoside linkage where a phosphorus atom is linked to a morpholino group and to the ring nitrogen of a 4-aminopiperdin-1-yl (i.e., APN). In specific embodiments, an antisense oligomer comprising a targeting sequence as set forth in Table 2 comprises at least one APN-containing linkage or APN derivative-containing linkage. Various embodiments include morpholino-based oligomers that have about 10%, 15%, 20%, 25%, 30%, 35%, 40%, 45%, 50%, 55%, 60%, 65%, 70%, 75%, 80%, 85%, 90%, 95%, or 100% APN/APN derivative-containing linkages, where the remaining linkages (if less than 100%) are uncharged linkages, e.g., about or at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 of the total internucleoside linkages are APN/APN derivative-containing linkages.

In certain embodiments, the antisense oligomer is a compound of formula (I):

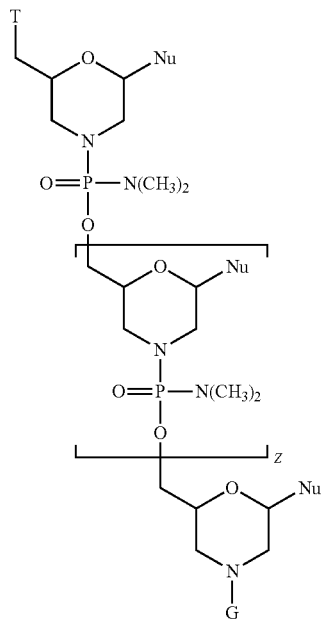

(I)

or a pharmaceutically acceptable salt thereof,
where each Nu is a nucleobase which taken together forms a targeting sequence;

Z is an integer from 8 to 38;
T is selected from:

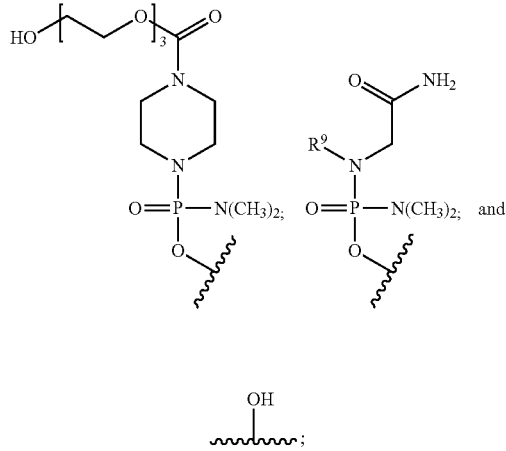

and
G is a cell penetrating peptide ("CPP") and linker moiety.

In some embodiments, G is selected from —C(O)(CH$_2$)$_5$NH—CPP—R$^a$, —C(O)(CH$_2$)$_2$NH—CPP—R$^a$, —C(O)(CH$_2$)$_2$NHC(O)(CH$_2$)$_5$NH—CPP—R$^a$, —C(O)CH$_2$NH—CPP—R$^a$, and:

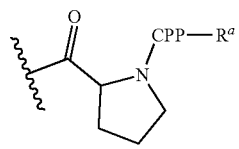

wherein the CPP is attached to the linker moiety by an amide bond at the CPP carboxy terminus, and R$^a$ is a moiety attached to the CPP amino terminus R$^a$ by an amide bond, wherein R$^a$ is selected from H, acetyl, benzoyl, and stearoyl. In some embodiments, R$^a$ is acetyl. In some embodiments, CPP is selected from SEQ ID NOS: 5-21. In certain embodiments, G is selected from SEQ ID NOS: 22-25. In some embodiments, CPP is SEQ ID NO: 11. In certain embodiments, G is SEQ ID NO: 25.

In certain embodiments, G is selected from: —C(O)CH$_2$NH—CPP—R$^a$, and

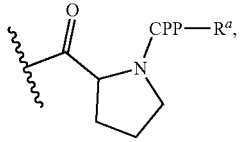

wherein the CPP is attached to the linker moiety by an amide bond at the CPP carboxy terminus, R$^a$ is attached to the CPP amino terminus by an amide bond, wherein R$^a$ is selected from H, acetyl, benzoyl, and stearoyl, and the CPP is selected from SEQ ID NOS: 5-21. In some embodiments, CPP is SEQ ID NO: 11. In some embodiments, R$^a$ is acetyl.

In some embodiments, T is

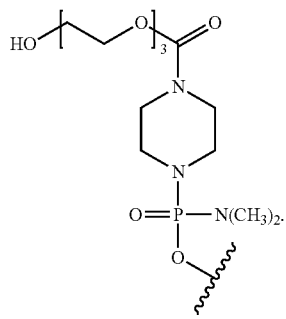

In various aspects, an antisense oligonucleotide of the disclosure includes a compound of formula (II):

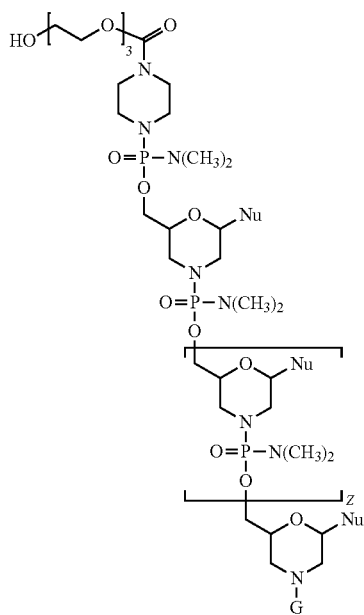

(II)

or a pharmaceutically acceptable salt thereof, wherein:
where each Nu is a nucleobase which taken together forms a targeting sequence;
Z is an integer from 8 to 38; and
G is a cell penetrating peptide ("CPP") and linker moiety.
In some embodiments, G is selected from —C(O)(CH$_2$)$_5$NH—CPP—R$^a$,    —C(O)(CH$_2$)$_2$NH—CPP—R$^a$, —C(O)(CH$_2$)$_2$NHC(O)(CH$_2$)$_5$NH—CPP—R$^a$,    —C(O)CH$_2$NH—CPP—R$^a$, and:

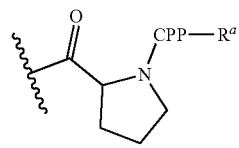

wherein the CPP is attached to the linker moiety by an amide bond at the CPP carboxy terminus, and R$^a$ is a moiety attached to the CPP amino terminus R$^a$ by an amide bond, wherein R$^a$ is selected from H, acetyl, benzoyl, and stearoyl.

In some embodiments, R$^a$ is acetyl. In some embodiments, CPP is selected from SEQ ID NOS: 5-21. In certain embodiments, G is selected from SEQ ID NOS: 22-25. In some embodiments, CPP is SEQ ID NO: 11. In certain embodiments, G is SEQ ID NO: 25.

In certain embodiments, G is selected from: —C(O)CH$_2$NH—CPP—R$^a$, and

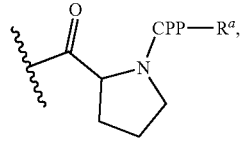

wherein the CPP is attached to the linker moiety by an amide bond at the CPP carboxy terminus, R$^a$ is attached to the CPP amino terminus by an amide bond, wherein R$^a$ is selected from H, acetyl, benzoyl, and stearoyl, and the CPP is selected from SEQ ID NOS: 5-21. In some embodiments, CPP is SEQ ID NO: 11. In certain embodiments, G is selected from SEQ ID NOS: 24 or 25. In some embodiments, G is SEQ ID NO: 25.

In some embodiments, the targeting sequence of an antisense oligomers of the disclosure, including, for example, some embodiments of the antisense oligomers of formula (I) and (II), is selected from:

a)
SEQ ID NO: 3
(CTGAGCCGCTGGCAGATGCCTTGTC)
wherein Z is 23;
and b)
SEQ ID NO: 4
(GAGGAGATGGGTCCACCCACCTGGG)
wherein Z is 23.

Peptide Transporters
CPPs and Arginine-Rich Peptide Conjugates of PMOs (PPMOs)

In certain embodiments, the antisense oligonucleotide is conjugated to a cell-penetrating peptide (referred to herein as "CPP"). In some embodiments, the CPP is an arginine-rich peptide. The term "arginine-rich" refers to a CPP having at least 2, and preferably 2, 3, 4, 5, 6, 7, or 8 arginine residues, each optionally separated by one or more uncharged, hydrophobic residues, and optionally containing about 6-14 amino acid residues. As explained below, a CPP is preferably linked at its carboxy terminus to the 3' and/or 5' end of an antisense oligonucleotide through a linker, which may also be one or more amino acids, and is preferably also capped at its amino terminus by a substituent R$^a$ with R$^a$ selected from H, acetyl, benzoyl, or stearoyl. In some embodiments, R$^a$ is acetyl.

TABLE 3

Exemplary CPPs (SEQ ID NOS: 5-21) and CPP and linker moiety combinations (SEQ ID NOS: 22-25)

| NAME (DESIGNATION) | SEQUENCE | SEQ ID NO. |
|---|---|---|
| rTAT | RRRQRRKKR | 5 |
| Tat | RKKRRQRRR | 6 |

TABLE 3 -continued

Exemplary CPPs (SEQ ID NOS: 5-21) and CPP and linker moiety combinations (SEQ ID NOS: 22-25)

| NAME (DESIGNATION) | SEQUENCE | SEQ ID NO. |
|---|---|---|
| $R_9F_2$ | RRRRRRRRFF | 7 |
| $R_5F_2R_4$ | RRRRRFFRRRR | 8 |
| $R_4$ | RRRR | 9 |
| $R_5$ | RRRRR | 10 |
| $R_6$ | RRRRRR | 11 |
| $R_7$ | RRRRRRR | 12 |
| $R_8$ | RRRRRRRR | 13 |
| $R_9$ | RRRRRRRRR | 14 |
| $(RX)_8$ | RXRXRXRXRXRXRXRX | 15 |
| $(RXR)_4$ | RXRXRRXRRXXR | 16 |
| $(RXR)_5$ | RXRRXRXRXRXRRXR | 17 |
| $(RXRRBR)_2$ | RXRBRRXRRBR | 18 |
| $(RAR)_4F_2$ | RARRARRARRARFF | 19 |
| $(RGR)_4F_2$ | RGRRGRRGRRGRFF | 20 |
| $(RFF)_3R$ | RFFRFFRFFR | 21 |
| $(RXR)_4XB$ | RXRRXRRXRRXRXB | 22 |
| $(RFF)_3RXB$ | RFFRFFRFFRXB | 23 |
| $(RFF)_3RG$ | RFFRFFRFFRG | 24 |
| $R_6G$ | RRRRRRG | 25 |

X is 6-aminohexanoic acid; B is β-alanine; F is phenylalanine; G is glycine; R is arginine; Q is glutamine; K is lysine.
Each of SEQ ID NOS: 5-25 may further comprise a group $R^a$ attached to the amino terminus wherein $R^a$ is selected from H, acetyl, benzoyl, and stearoyl.
In some embodiments, $R^a$ is acetyl.

CPPs, their synthesis, and methods of conjugating to an oligomer are further described in U.S. Application Publication No. 2012/0289457 and PCT Patent Application Publication Nos. WO 2004/097017, WO 2009/005793, and WO 2012/150960, the disclosures of which are incorporated herein by reference in their entirety.

In various embodiments, G (as recited in formulas (I) and (II)) G is a cell penetrating peptide ("CPP") and linker moiety selected from —C(O)(CH$_2$)$_5$NH—CPP—$R^a$, —C(O)(CH$_2$)$_2$NH—CPP—$R^a$, —C(O)(CH$_2$)$_2$NHC(O)(CH$_2$)$_5$NH—CPP—$R^a$, —C(O)CH$_2$NH—CPP—$R^a$, and:

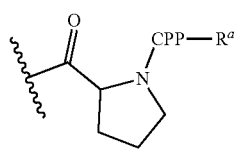

wherein the CPP is attached to the linker moiety by an amide bond at the CPP carboxy terminus, and $R^a$ is a moiety attached to the CPP amino terminus $R^a$ by an amide bond, wherein $R^a$ is selected from H, acetyl, benzoyl, and stearoyl. In some embodiments, $R^a$ is acetyl. In some embodiments, the CPP comprises or is selected from SEQ ID NOS: 5-21. In some embodiments, G comprises or is selected from SEQ ID NOS: 22-25. In certain embodiments, CPP is SEQ ID NO: 11. In some embodiments, G is SEQ ID NO: 25.

In some embodiments, G (as recited in formulas (I) and (II)) is of the formula:

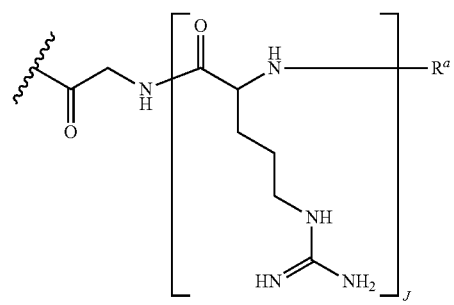

wherein $R^a$ is selected from H, acetyl, benzoyl, and stearoyl, and J is an integer from 4 to 9. In certain embodiments J is 6.

In various embodiments, the CPP—$R^a$ (as recited in formulas (I) and (II)) is of the formula:

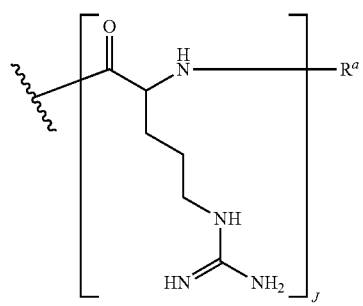

wherein $R^a$ is selected from H, acetyl, benzoyl, and stearoyl, and J is an integer from 4 to 9. In certain embodiments, the CPP is SEQ ID NO: 11. In various embodiments, J is 6. In some embodiments $R^a$ is selected from H and acetyl. For example, in some embodiments, $R^a$ is H. In certain embodiments, $R^a$ is acetyl.

In some embodiments, G comprises or is selected from SEQ ID NOS: 22-25. In certain embodiments, G is SEQ ID NO: 25.

In certain embodiments, including, for example, antisense oligomers of formula (I) and (II), G is —C(O)CH$_2$NH—R$_6$—$R^a$ covalently bonded to an antisense oligomer of the disclosure at the 3' end of the oligomer, wherein $R^a$ is H, acetyl, benzoyl, or stearoyl to cap the amino terminus of the R$_6$. In some embodiments, $R^a$ is acetyl. In these non-limiting examples, the CPP is —R$_6$—$R^a$ and the linker is —C(O)

CH$_2$NH—, (i.e., glycine). This particular example of G=—C(O)CH$_2$NH—R$_6$—R$^a$ is also exemplified by the following structure:

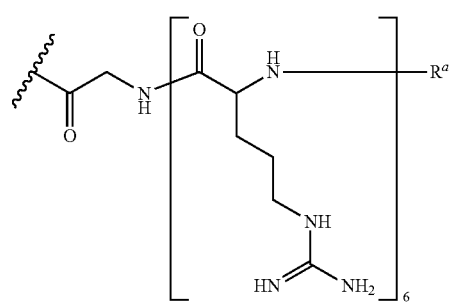

wherein R$^a$ is selected from H, acetyl, benzoyl, and stearoyl. In some embodiments, R$^a$ is acetyl.

In various embodiments, the CPP—R$^a$ is —R$_6$—R$^a$ wherein CPP is SEQ ID NO: 11, also exemplified as the following formula:

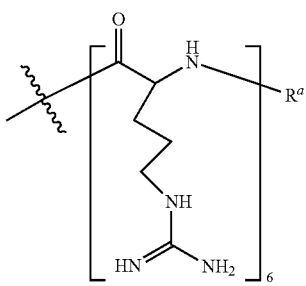

wherein R$^a$ is selected from H, acetyl, benzoyl, and stearoyl. In certain embodiments, the CPP is SEQ ID NO: 11. In some embodiments, R$^a$ is acetyl.

In some embodiments, the CPP—R$^a$ is of the formula —(RXR)$_4$—R$^a$ wherein CPP is SEQ ID NO: 16, also exemplified as the following formula:

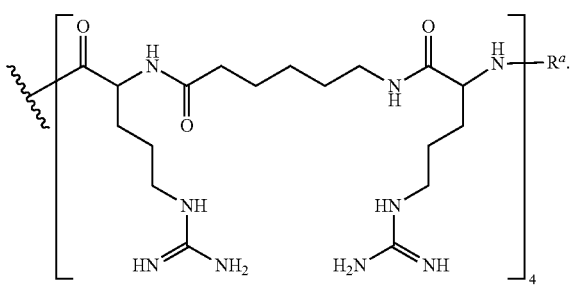

In various embodiments, the CPP—R$^a$ is —R—(FFR)$_3$—R$^a$ wherein CPP is SEQ ID NO: 21, also exemplified as the following formula:

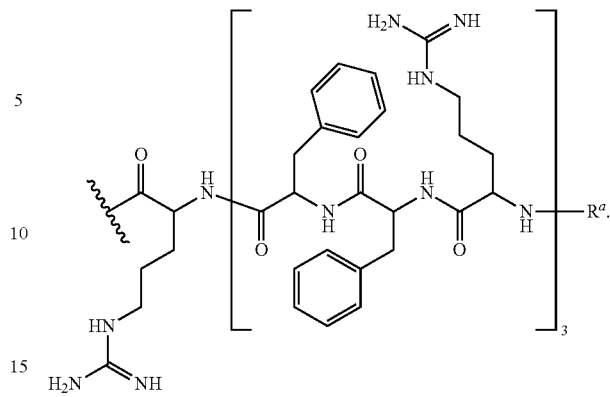

In various embodiments, G is a cell penetrating peptide ("CPP") and linker moiety selected from —C(O)(CH$_2$)$_5$NH—CPP—R$^a$, —C(O)(CH$_2$)$_2$NH—CPP—R$^a$, —C(O)(CH$_2$)$_2$NHC(O)(CH$_2$)$_5$NH—CPP—R$^a$, —C(O)CH$_2$NH—CPP—R$^a$, and:

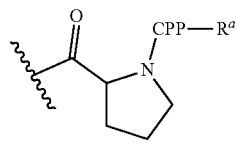

wherein the CPP is attached to the linker moiety by an amide bond at the CPP carboxy terminus, and R$^a$ is attached to the CPP amino terminus by an amide bond, wherein R$^a$ is selected from H, acetyl, benzoyl, and stearoyl, and wherein the CPP—R$^a$ is selected from:

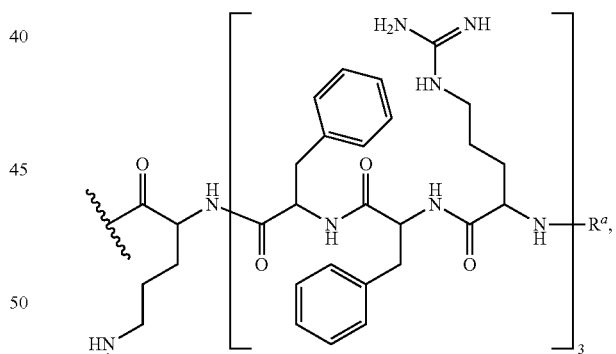

(—R—(FFR)$_3$—R$^a$),

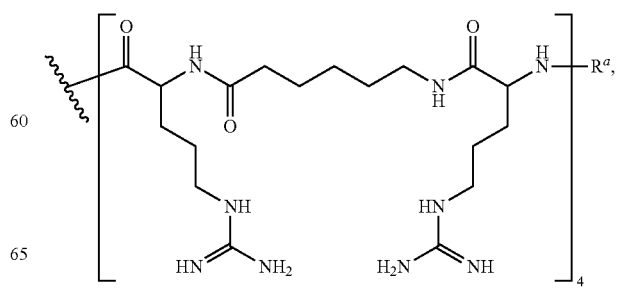

-continued (—(RXR)₄—R$^a$), or (—R₆—R$^a$).

In some embodiments, R$^a$ is acetyl.

Further, in some embodiments, an antisense oligomer of the disclosure is a compound of formula (III):

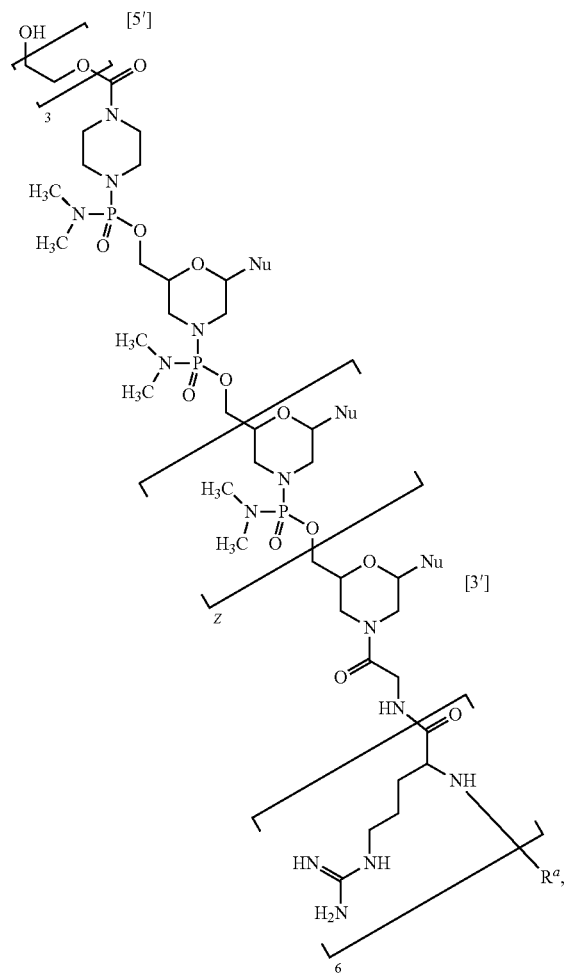

(III)

or a pharmaceutically acceptable salt thereof, wherein:
each Nu is a nucleobase which taken together form a targeting sequence (5' to 3') selected from:
a) SEQ ID NO: 3 (CTGAGCCGCTGGCAGATGCCTTGTC) wherein Z is 23; and
b) SEQ ID NO: 4 (GAGGAGATGGGTCCACCCACCTGGG) wherein Z is 23;
and R$^a$ is selected from H, acetyl, benzoyl, and stearoyl.

In some embodiments, the targeting sequence is SEQ ID NO: 3 (CTGAGCCGCTGGCAGATGCCTTGTC) and Z is 23. In certain embodiments, the targeting sequence is SEQ ID NO: 4 (GAGGAGATGGGTCCACCCACCTGGG) and Z is 23. In some embodiments, R$^a$ is acetyl.

In some embodiments of the antisense oligomers of the disclosure including, for example, some embodiments of antisense oligomers of formula (III), the antisense oligomer can be of formula (IV):

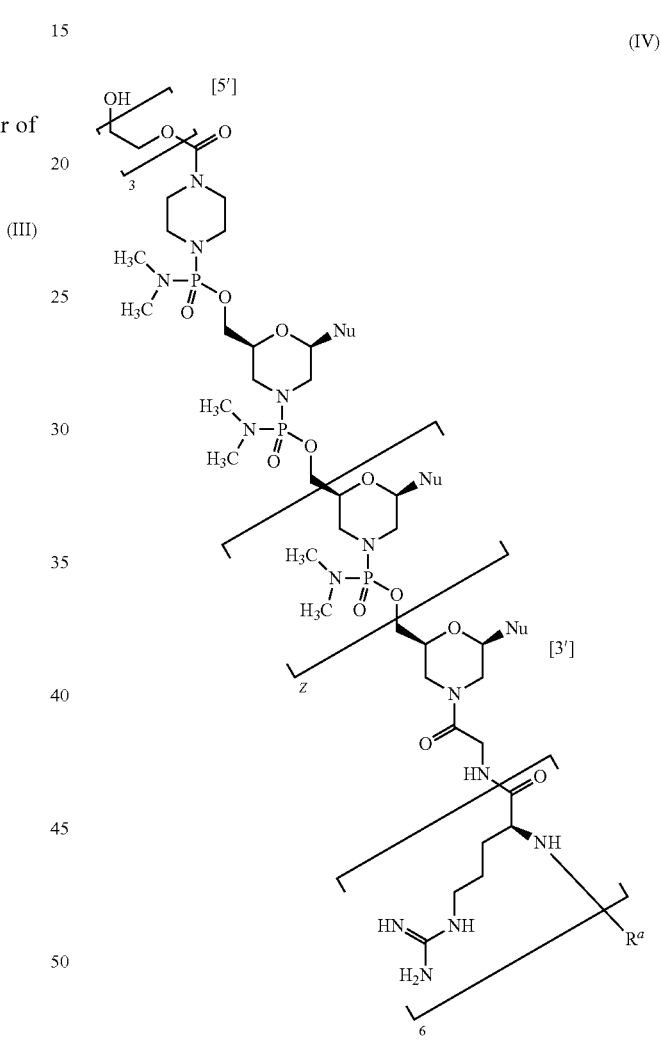

(IV)

or a pharmaceutically acceptable salt thereof, wherein:
each Nu is a nucleobase which taken together form a targeting sequence (5' to 3') selected from:
a) SEQ ID NO: 3 (CTGAGCCGCTGGCAGATGCCTTGTC) wherein Z is 23; and
b) SEQ ID NO: 4 (GAGGAGATGGGTCCACCCACCTGGG) wherein Z is 23;
and R$^a$ is selected from H, acetyl, benzoyl, and stearoyl.

In some embodiments, the targeting sequence is SEQ ID NO: 3 (CTGAGCCGCTGGCAGATGCCTTGTC) and Z is 23. In certain embodiments, the targeting sequence is SEQ ID NO: 4 (GAGGAGATGGGTCCACCCACCTGGG) and Z is 23. In some embodiments, R$^a$ is acetyl.

In some embodiments, the antisense oligomer compound of formula (III) is of formula (IV) wherein the targeting sequence is SEQ ID NO: 3 (CTGAGCCGCTGGCAGAT-GCCTTGTC) and Z is 23. In some embodiments, the antisense oligomer compound of formula (III) is of formula (IV) wherein the targeting sequence is SEQ ID NO: 4 (GAGGAGATGGGTCCACCCACCTGGG) and Z is 23.

In some embodiments, the antisense oligomer is a compound of formula (V), or a pharmaceutically acceptable salt thereof, selected from:

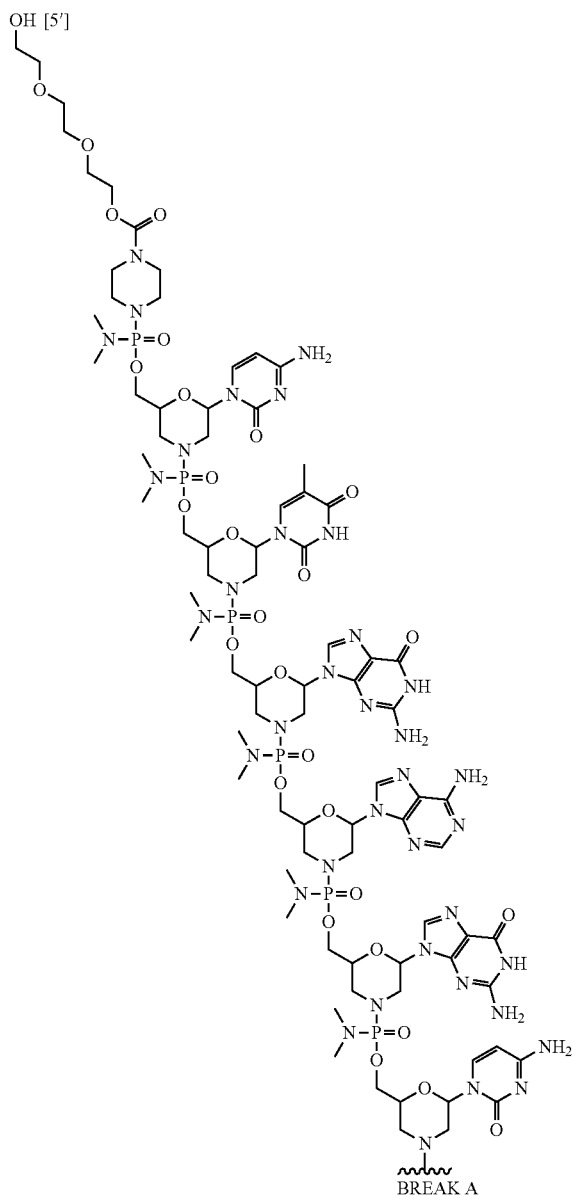

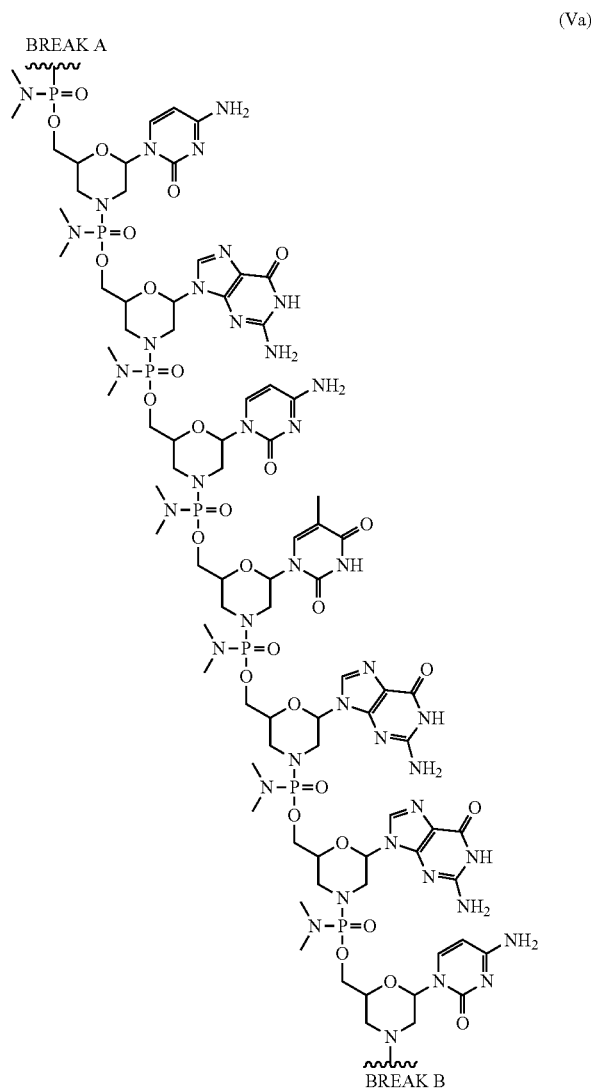

(Va)

-continued
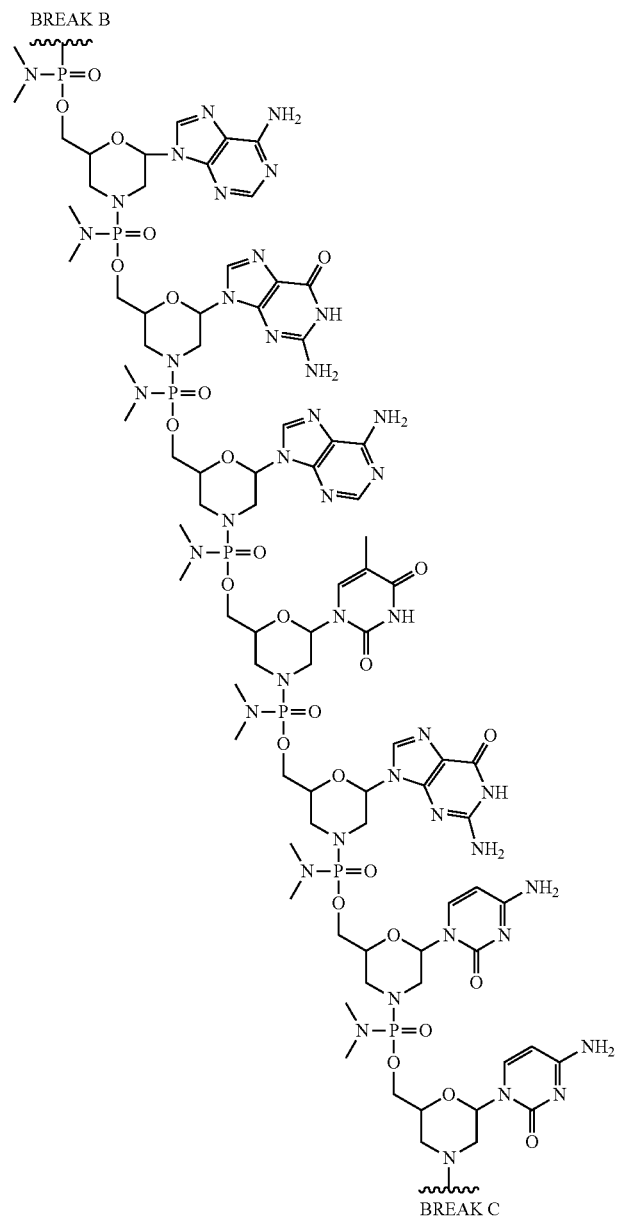
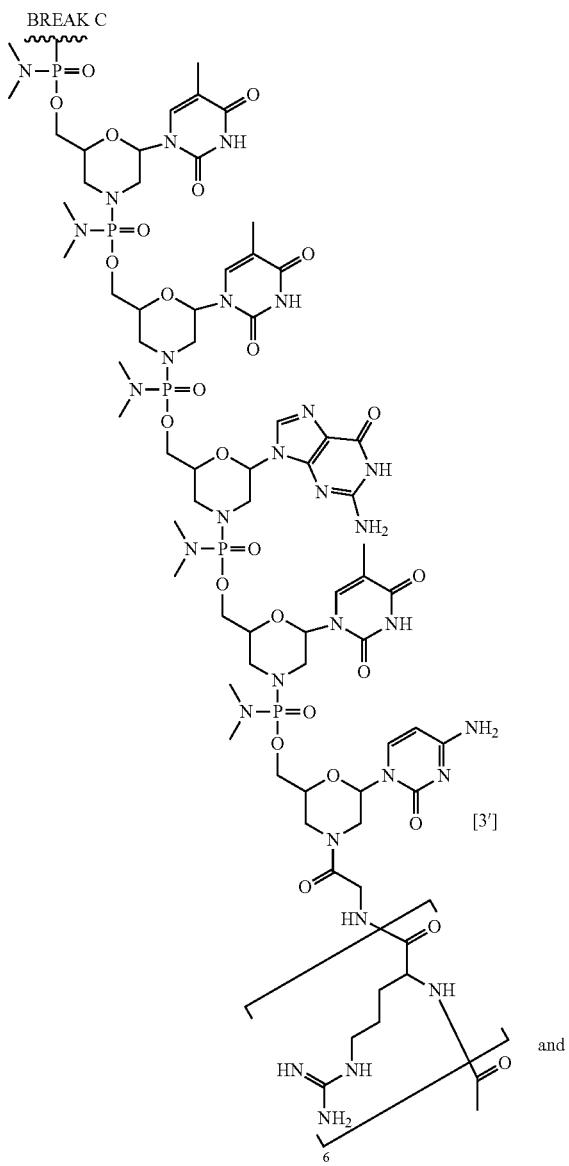

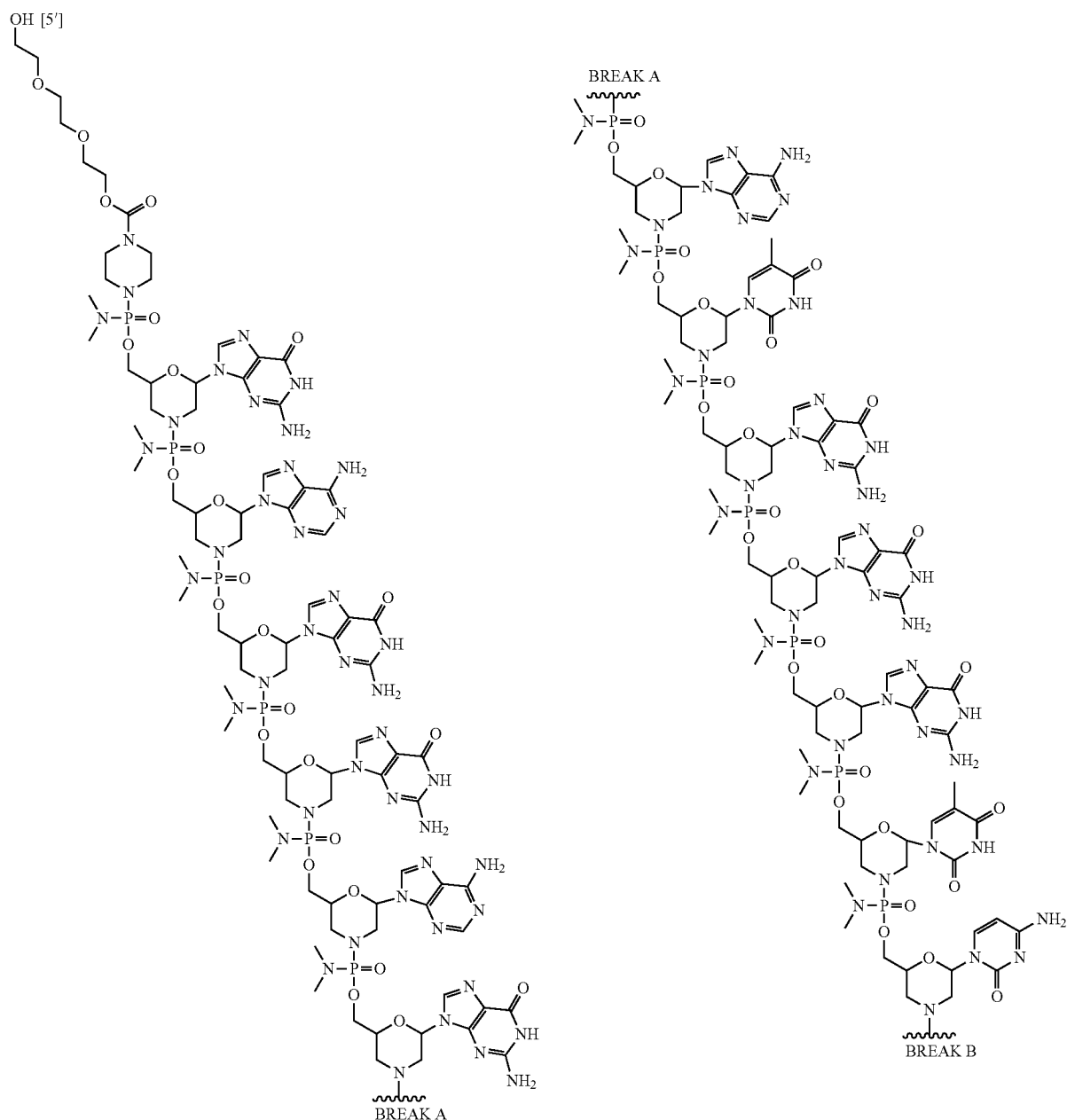

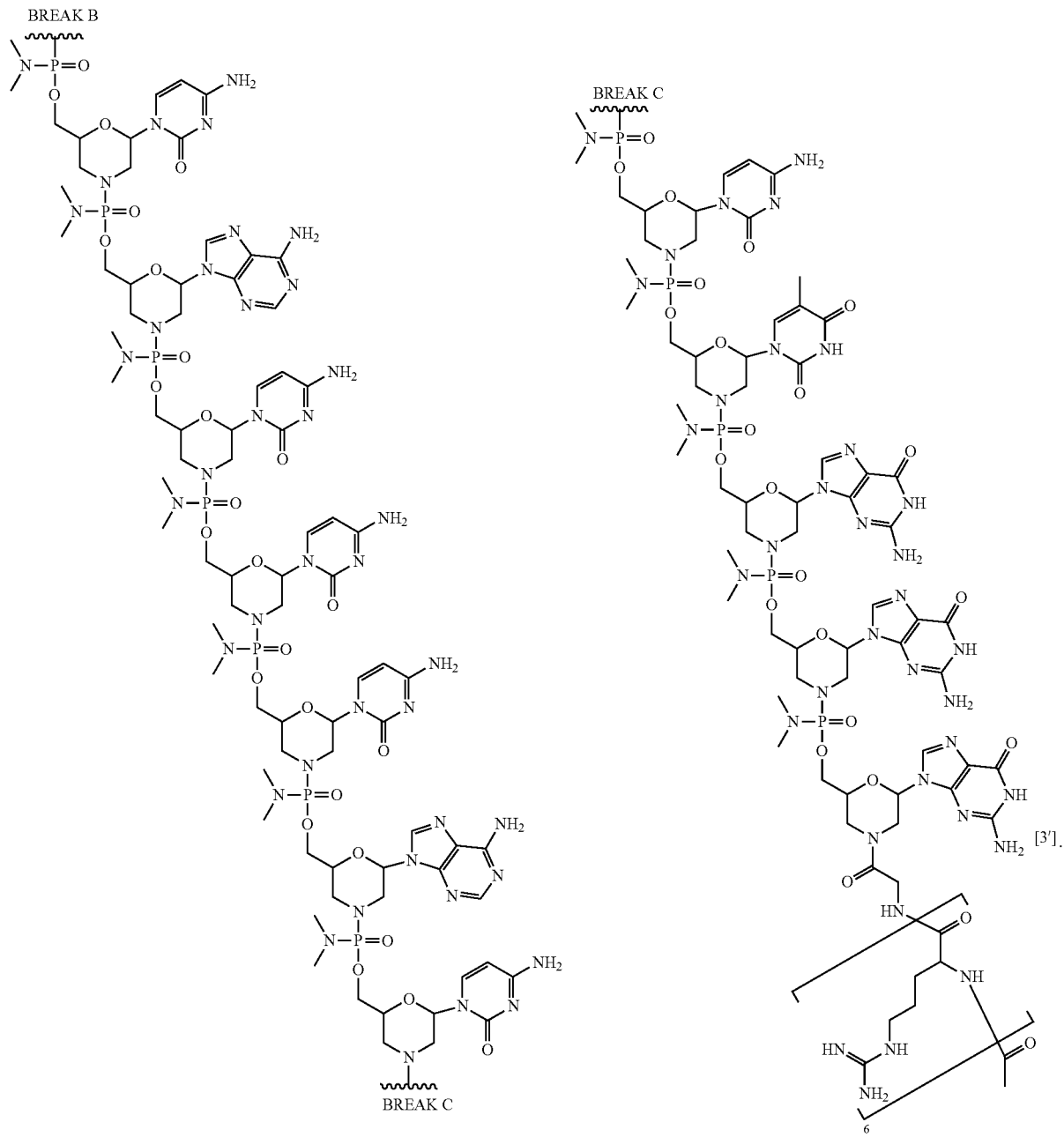

In some embodiments, the antisense oligomer of formula (V) is of formula (V a). In certain embodiments, the antisense oligomer of formula (V) is of formula (V b).

In some embodiments, an antisense oligomer of the disclosure including, for example, a compound of formula (III), formula (IV), formula (V), formula (Va), and formula (Vb), is a pharmaceutically acceptable salt. In certain embodiments, the pharmaceutically acceptable salt is an HCl (hydrochloric acid) salt. For example, in some embodiments, a compound of formula (III) is an HCl salt. In certain embodiments, a compound of formula (III) is a 0.6 HCl salt. In some embodiments, a compound of formula (IV) is an HCl salt. In certain embodiments, a compound of formula (IV) is a 0.6 HCl salt. In some embodiments, a compound of formula (V) is an HCl salt. In certain embodiments, a compound of formula (V) is a 0.6 HCl salt. In some embodiments, a compound of formula (Va) is an HCl salt. In certain embodiments, a compound of formula (Va) is a 0.6 HCl salt. In some embodiments, a compound of formula (Vb) is an HCl salt. In certain embodiments, a compound of formula (Vb) is a 0.6 HCl salt.

In some embodiments of the antisense oligomers of the disclosure including, for example, some embodiments of antisense oligomers of formula (V), the antisense oligomers may be a compound of formula (VI), or a pharmaceutically acceptable salt thereof, selected from:

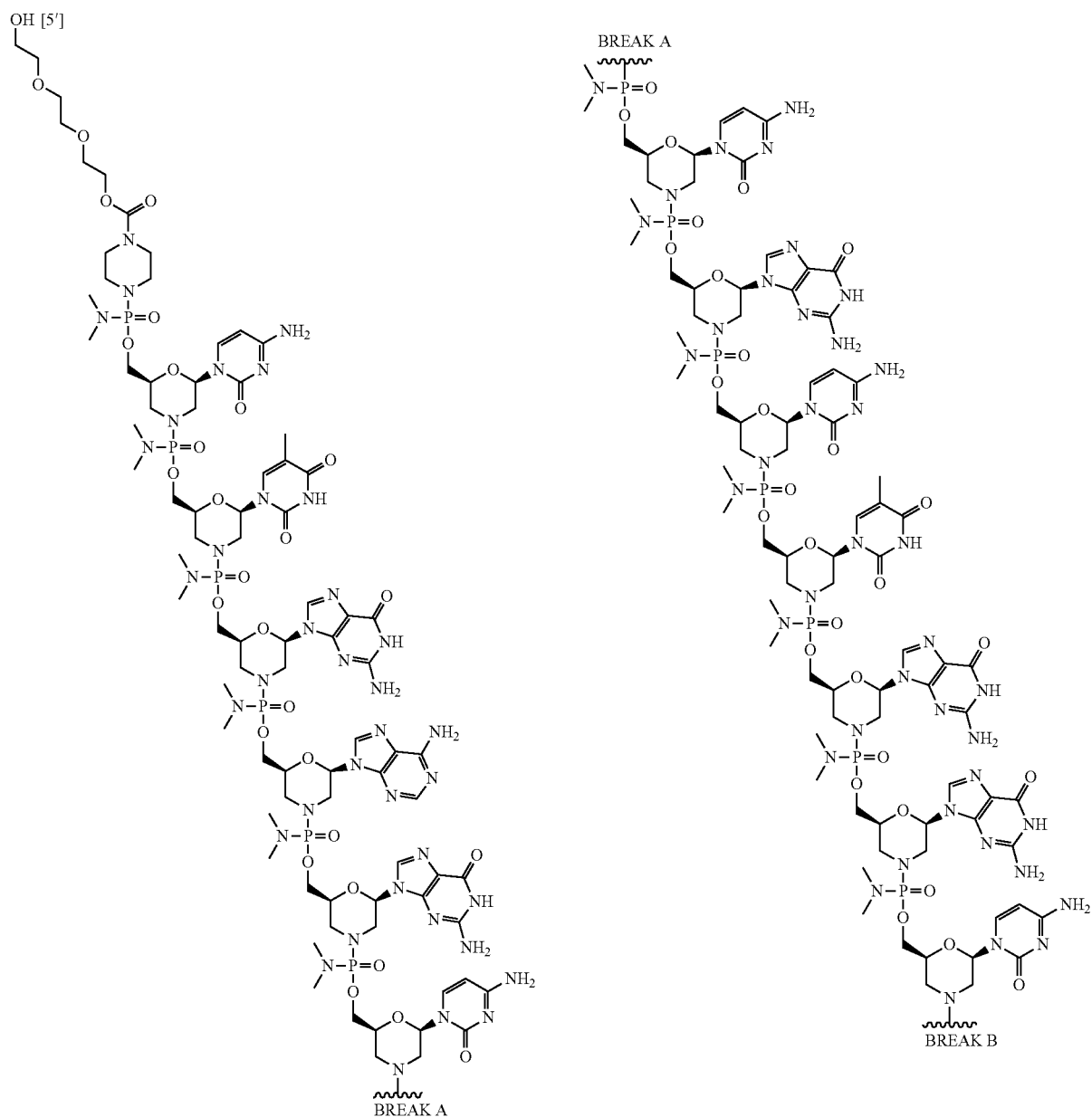
(VIa)

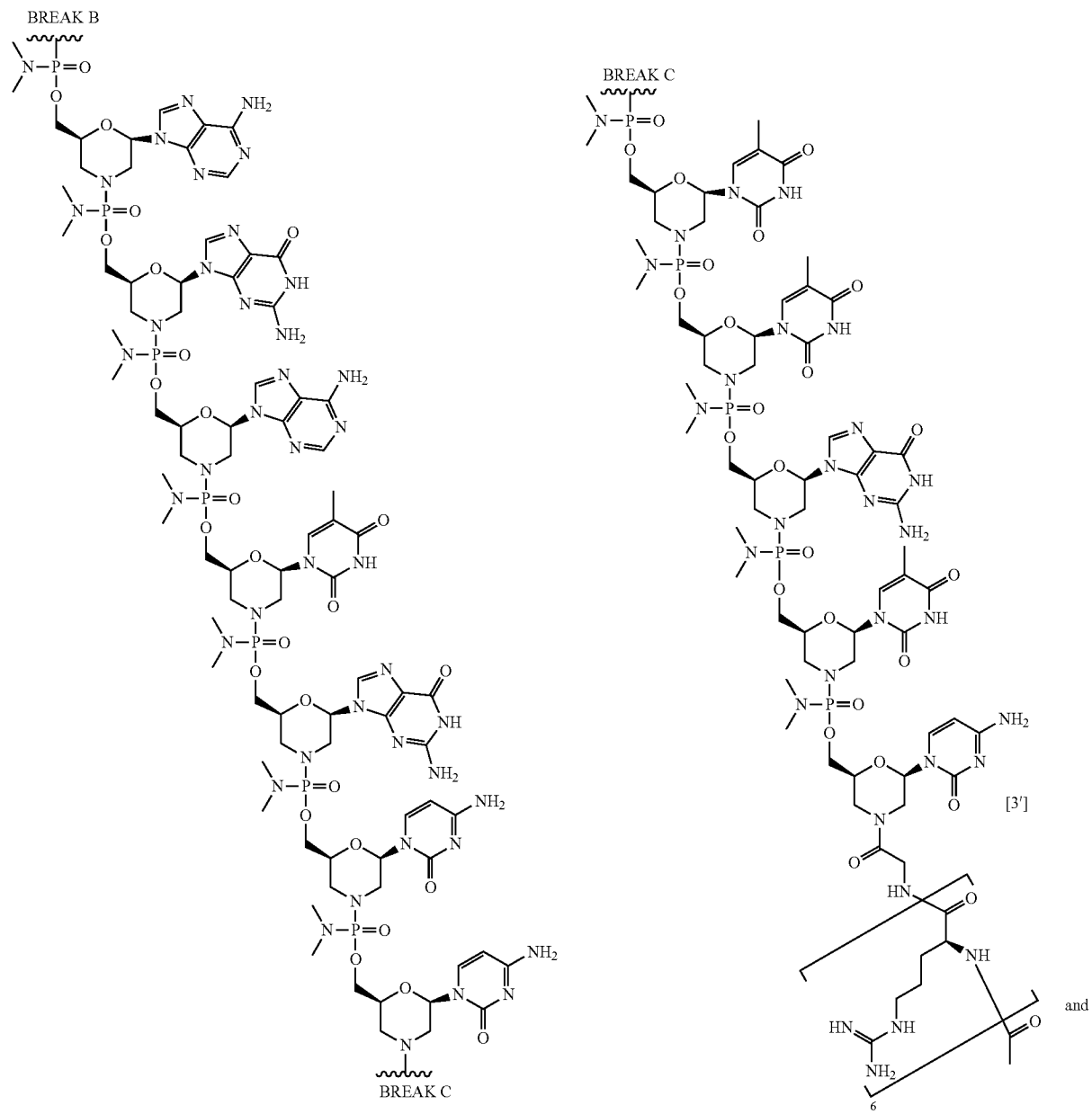

-continued
(VIb)
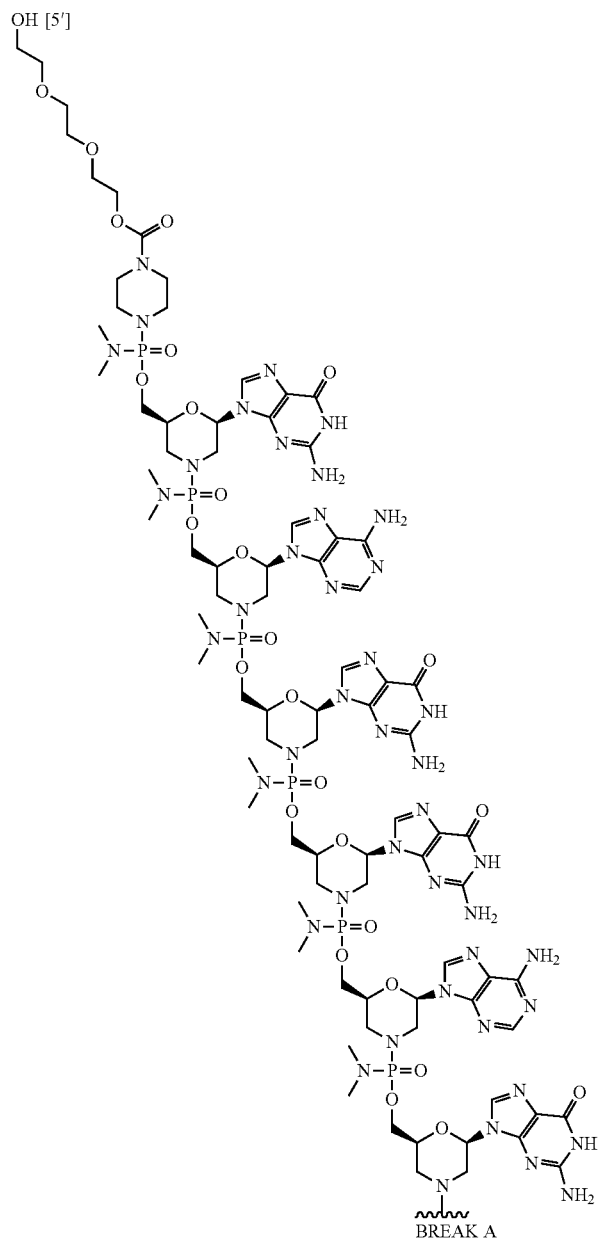
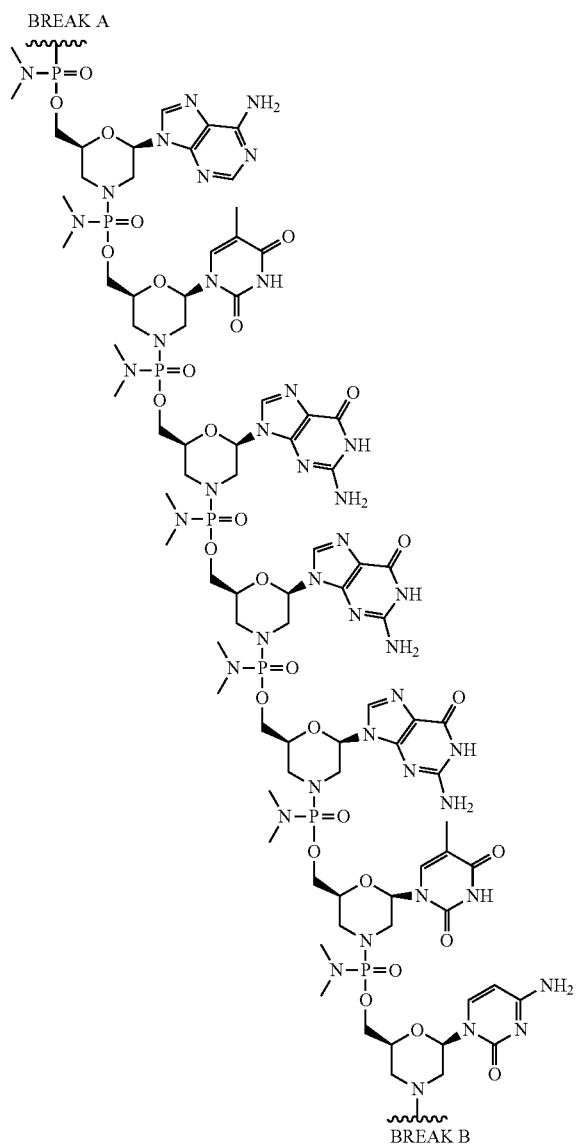

-continued

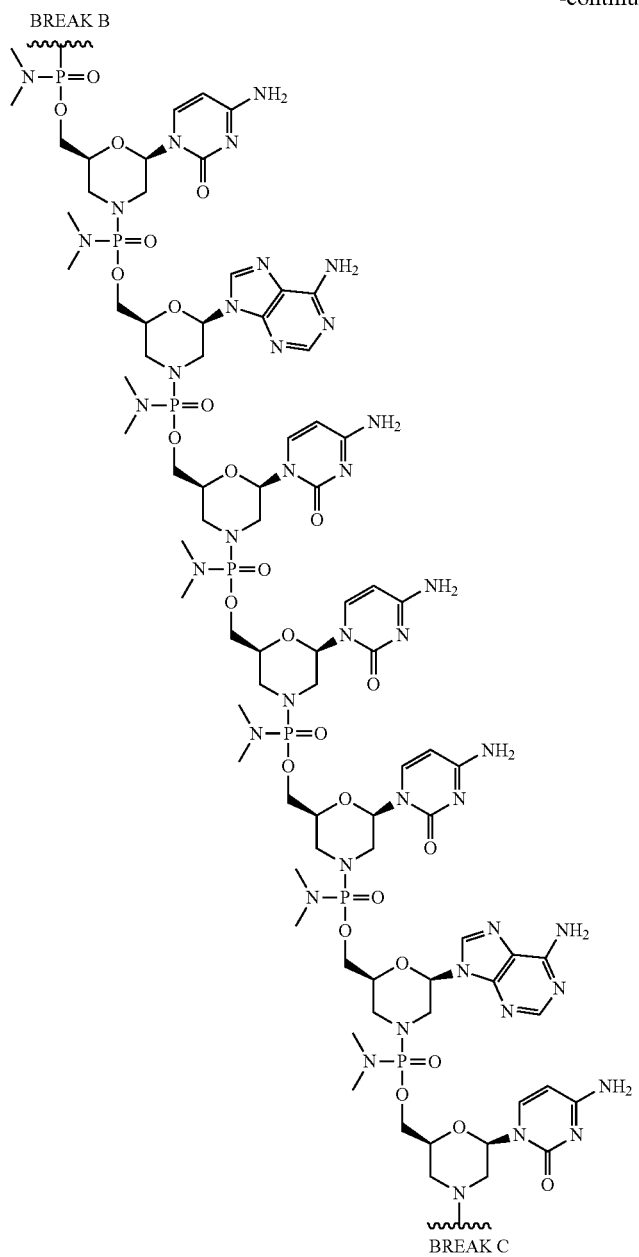

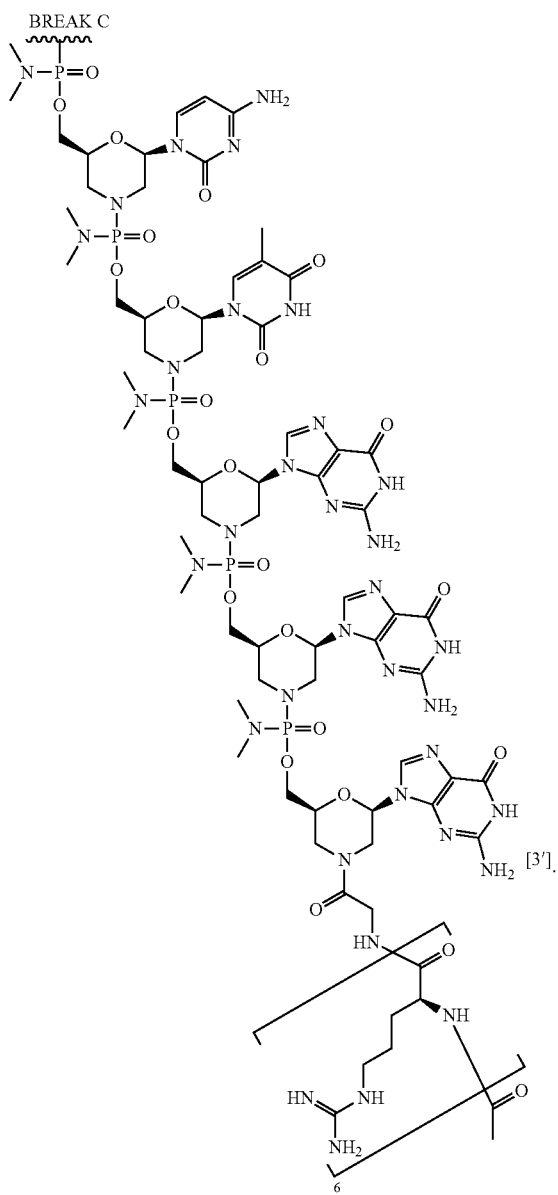

In some embodiments, the antisense oligomer of formula (VI) is of formula (VI a). In certain embodiments, the antisense oligomer of formula (VI) is of formula (VI b). In certain embodiments, the antisense oligomer compound of formula (V) is of formula (VI a). In some embodiments, the antisense oligomer compound of formula (V) is of formula (VI b).

In some embodiments, an antisense oligomer of the disclosure including, for example, a compound of formula (VI), formula (VI a), and formula (VI b), is a pharmaceutically acceptable salt. In certain embodiments, the pharmaceutically acceptable salt is an HCl (hydrochloric acid) salt. For example, in some embodiments, a compound of formula (VI) is an HCl salt. In certain embodiments, a compound of formula (VI) is a 0.6 HCl salt. In some embodiments, a compound of formula (VI a) is an HCl salt. In certain embodiments, a compound of formula (VI a) is a 0.6 HCl salt. In some embodiments, a compound of formula (VI b) is an HCl salt. In certain embodiments, a compound of formula (VI b) is a 0.6HCl salt.

For clarity, the structural formula of the antisense oligomers of formulas (V) and (VI) is a continuous structural formula from 5' to 3', and, for ease of illustrating the entire structural formula in a compact form, are presented herein with various illustration breaks labeled "BREAK A," "BREAK B," and "BREAK C." The skilled artisan understands that, for example, each indication of "BREAK A" shows a continuation of the illustration of the structural formula at these points. The same is true for each instance of "BREAK B" and "BREAK C" in the structural formula of the antisense oligomers of formulas (V) and (VI). None of the illustration breaks described above or used herein are intended to indicate, nor would the skilled artisan understand them to mean, an actual discontinuation of the structural formula of the antisense oligomers of formulas (V) and (VI).

Methods of Use and Pharmaceutical Formulations

The present invention relates to methods for treating progeroid diseases, such as laminopathies and related diseases or conditions in a subject in need thereof by administering to the subject an antisense oligonucleotide as described herein, or a pharmaceutical composition containing the same, wherein the oligonucleotide inhibits expression of mutant LMNA protein mRNA by modulating splicing of LMNA pre-mRNA. In certain aspects, for example, these and related methods can be applied to treating progeroid laminopathies in clinical settings where progerin expression is associated with a disease such as HGPS. These and related embodiments can also be combined with methods of treating or reducing progeroid laminopathies, by concurrently or sequentially carrying out the methods of the invention with the other treatment.

The results described herein can be generalized to the aging process and related conditions and diseases, beyond progeroid laminopathies. This is because HGPS is in many respects closely connected to normal aging processes. HGPS continues to be recognized as a useful model of aging (Fossel, J. Pediatr Endocrinol Metab 13 Suppl 6:1477-1481, 2000). For instance, the connection to atherosclerosis is very strong, especially of the coronary arteries. In addition, alopecia in HGPS is similar to that seen in subjects with advanced age. Further, the prime cellular feature of HGPS, as described many years ago by Hayflick and others (Hayflick, N Engl J Med 295:1302-1308, 1976) is early cellular senescence. The limited number of cell divisions in HGPS fibroblasts is similar to what is seen in fibroblasts derived from elderly individuals. That was further explored by research showing similarities in the gene expression patterns of HGPS fibroblasts and those derived from elderly persons, distinguishing them from fibroblasts derived from younger persons (Ly et al., Science 287: 2486-2492, 2000).

Accordingly, it will be understood that a method for treating a progeroid disease or related condition as described herein can include the treatment of a progeroid laminopathy, such as HGPS, or another progeroid disease or condition, an age-related condition, a cardiovascular disease or condition (such as atherosclerosis), and the like.

It will be understood that an effective in vivo treatment regimen using the methods of the invention may vary according to the duration, dose, frequency and route of administration of an oligonucleotide, as well as the condition of the subject under treatment (i.e., prophylactic administration versus administration in response to an existing condition). Accordingly, such in vivo therapy will often require monitoring by tests appropriate to the particular type of disease under treatment, and corresponding adjustments in the dose or treatment regimen, in order to achieve an optimal therapeutic outcome.

In certain embodiments, the methods of the invention employ formulations or compositions suitable for the therapeutic delivery of antisense oligomers, as described herein. Hence, in certain embodiments, the methods of the present invention employ pharmaceutically acceptable compositions that comprise a therapeutically-effective amount of one or more of the oligomers or agents described herein, formulated together with one or more pharmaceutically acceptable carriers (additives) and/or diluents. While it is possible for an oligomer of the present invention to be administered alone, it is preferable to administer the compound as a pharmaceutical formulation (composition).

Methods for the delivery of nucleic acid molecules are described, for example, in Akhtar et al., 1992, *Trends Cell Bio.*, 2:139; and *Delivery Strategies for Antisense Oligonucleotide Therapeutics*, ed. Akhtar; Sullivan et al., PCT Application Publication No. WO 94/02595. These and other protocols can be utilized for the delivery of virtually any nucleic acid molecule, including the isolated oligomers of the present invention.

As detailed below, the pharmaceutical compositions used in the methods of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

Some examples of materials that can serve as pharmaceutically-acceptable carriers include, without limitation: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Additional non-limiting examples of agents suitable for formulation with the antisense oligomers of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues; biodegradable polymers, such as poly (DL-lactide-coglycolide) microspheres for sustained release delivery after implantation (Emerich, D F et al., 1999, *Cell Transplant*, 8, 47-58) Alkermes, Inc. Cambridge, Mass.; and loaded nanoparticles, such as those made of polybutylcyanoacrylate, which can deliver drugs across the blood brain barrier and can alter neuronal uptake mechanisms (*Prog Neuropsychopharmacol Biol Psychiatry*, 23, 941-949, 1999).

The methods of the invention also feature the use of a composition comprising surface-modified liposomes containing poly (ethylene glycol) lipids (PEG-modified, branched and unbranched or combinations thereof, or long-circulating liposomes or stealth liposomes). Oligomers of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). Such liposomes have been shown to accumulate selectively in tumors, presumably by extravasation and capture in the neovascularized target tissues (Lasic et al., Science 1995, 267, 1275-1276; Oku et al., 1995, Biochim. Biophys. Acta, 1238, 86-90). The long-circulating liposomes enhance the pharmacokinetics and pharmacodynamics of DNA and RNA, particularly compared to conventional cationic liposomes which are known to accumulate in tissues of the MPS (Liu et al., J. Biol. Chem. 1995, 42, 24864-24870; Choi et al., PCT Publication No. WO 96/10391; Ansell et al., PCT Publication No. WO 96/10390; Holland et al., PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

In a further embodiment, the methods of the present invention includes oligomer compositions prepared for delivery as described in U.S. Pat. Nos. 6,692,911, 7,163,695 and 7,070,807. In this regard, in one embodiment, the present invention provides an oligomer of the present invention in a composition comprising copolymers of lysine and histidine (HK) as described in U.S. Pat. Nos. 7,163,695, 7,070,807, and 6,692,911 either alone or in combination with PEG (e.g., branched or unbranched PEG or a mixture of both), in combination with PEG and a targeting moiety or any of the foregoing in combination with a crosslinking agent. In certain embodiments, the present invention provides antisense oligomers in compositions comprising gluconic-acid-modified polyhistidine or gluconylated-polyhistidine/transferrin-polylysine. One skilled in the art will also recognize that amino acids with properties similar to His and Lys may be substituted within the composition.

In certain methods, the oligomers described herein may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject oligomers include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain methods, the oligomers of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations used in the present methods of the invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient that can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation used in the methods of the invention comprises an excipient selected from cyclodextrins, celluloses, liposomes, micelle forming agents, e.g., bile acids, and polymeric carriers, e.g., polyesters and polyanhydrides; and an oligomer of the present invention. In certain embodiments, an aforementioned formulation renders orally bioavailable an oligomer of the present invention.

Methods of preparing these formulations or compositions include the step of bringing into association an oligomer of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations used in the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. An oligomer of the present invention may also be administered as a bolus, electuary or paste.

In solid dosage forms used in the invention for oral administration (capsules, tablets, pills, dragees, powders, granules, trouches and the like), the active ingredient may be mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (e.g., gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions used according to the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations or dosage forms for the topical or transdermal administration of an oligomer as provided herein include powders, sprays, ointments, pastes, creams, lotions, gels, solutions, patches and inhalants. The active oligomers may be mixed under sterile conditions with a pharmaceutically-acceptable carrier, and with any preservatives, buffers, or propellants which may be required. The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an oligomer of the present invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of an oligomer of the present invention to the body. Such dosage forms can be made by dissolving or dispersing the oligomer in the proper medium. Absorption enhancers can also be used to increase the flux of the agent across the skin. The rate of such flux can be controlled by either providing a rate controlling membrane or dispersing the agent in a polymer matrix or gel, among other methods known in the art.

Pharmaceutical compositions suitable for parenteral administration may comprise one or more oligomers of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject oligomers may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility, among other methods known in the art. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms may be made by forming microencapsule matrices of the subject oligomers in biodegradable polymers such as polylactide-polyglycolide. Depending on the ratio of oligomer to polymer, and the nature of the particular polymer employed, the rate of oligomer release can be controlled. Examples of other biodegradable polymers include poly(orthoesters) and poly(anhydrides). Depot injectable formulations may also prepared by entrapping the drug in liposomes or microemulsions that are compatible with body tissues.

When the oligomers of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

As noted above, the formulations or preparations used in the present invention may be given orally, parenterally, topically, or rectally. They are typically given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

Regardless of the route of administration selected, the oligomers used in the present invention, which may be used in a suitable hydrated form, and/or the pharmaceutical compositions of the present invention, may be formulated into pharmaceutically-acceptable dosage forms by conventional methods known to those of skill in the art. Actual dosage levels of the active ingredients in the pharmaceutical compositions of this invention may be varied so as to obtain an amount of the active ingredient which is effective to achieve the desired therapeutic response for a particular patient, composition, and mode of administration, without being unacceptably toxic to the patient.

The selected dosage level will depend upon a variety of factors including the activity of the particular oligomer of the present invention employed, or the ester, salt or amide thereof, the route of administration, the time of administration, the rate of excretion or metabolism of the particular oligomer being employed, the rate and extent of absorption, the duration of the treatment, other drugs, compounds and/or materials used in combination with the particular oligomer employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. In certain situations, dosing is one administration per day. In certain embodiments, dosing is one or more administration per every 2, 3, 4, 5, 6, 7, 8, 9, 10, 11, 12, 13, 14 days, or every 1, 2, 3, 4, 5, 6, 7, 8, 9, 10, 11, 12 weeks, or every 1, 2, 3, 4, 5, 6, 7, 8, 9, 10, 11, 12 months, as needed, to treat the desired condition.

Antisense molecules can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres, as described herein and known in the art. In certain embodiments, microemulsification technology may be utilized to improve bioavailability of lipophilic (water insoluble) pharmaceutical agents. Examples include Trimetrine (Dordunoo, S. K., et al., *Drug Development and Industrial Pharmacy*, 17(12), 1685-1713, 1991 and REV 5901 (Sheen, P. C., et al., *J Pharm Sci* 80(7), 712-714, 1991). Among other benefits, microemulsification provides enhanced bioavailability by preferentially directing absorption to the lymphatic system instead of the circulatory system, which thereby bypasses the liver, and prevents destruction of the compounds in the hepatobiliary circulation.

In one aspect of invention, the formulations contain micelles formed from an oligomer as provided herein and at least one amphiphilic carrier, in which the micelles have an average diameter of less than about 100 nm. More preferred embodiments provide micelles having an average diameter less than about 50 nm, and even more preferred embodiments provide micelles having an average diameter less than about 30 nm, or even less than about 20 nm.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastro-intestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Examples of amphiphilic carriers include saturated and monounsaturated polyethyleneglycolyzed fatty acid glycerides, such as those obtained from fully or partially hydrogenated various vegetable oils. Such oils may advantageously consist of tri-, di-, and mono-fatty acid glycerides and di- and mono-polyethyleneglycol esters of the corresponding fatty acids, with a particularly preferred fatty acid composition including capric acid 4-10%, capric acid 3-9%, lauric acid 40-50%, myristic acid 14-24%, palmitic acid 4-14% and stearic acid 5-15%. Another useful class of amphiphilic carriers includes partially esterified sorbitan and/or sorbitol, with saturated or monounsaturated fatty acids (SPAN-series) or corresponding ethoxylated analogs (TWEEN-series).

Commercially available amphiphilic carriers may be particularly useful, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc. (produced and distributed by a number of companies in USA and worldwide).

In certain embodiments, the delivery may occur by use of liposomes, nanocapsules, microparticles, microspheres, lipid particles, vesicles, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. In certain embodiments, polymers have a molecular weight of from about 100 or 120 daltons up to about 5,000 or 10,000 daltons, or from about 300 daltons to about 5,000 daltons. In other embodiments, the polymer is polyethyleneglycol having a molecular weight of from about 100 to about 5,000 daltons, or having a molecular weight of from about 300 to about 5,000 daltons. In certain embodiments, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation used in the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter α, β, or γ, respectively. The glucose units are linked by α-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17α-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble cross-linked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 μm in diameter; large unilamellar vesicles (LUVS) are typically larger than 0.05 μm. Oligolamellar large vesicles and multilamellar vesicles have multiple, usually concentric, membrane layers and are typically larger than 0.1 μm. Liposomes with several non-concentric membranes, i.e., several smaller vesicles contained within a larger vesicle, are termed multivesicular vesicles.

One aspect of the present methods uses formulations comprising liposomes containing an oligomer of the present invention, where the liposome membrane is formulated to provide a liposome with increased carrying capacity. Alternatively or in addition, the compound of the present invention may be contained within, or adsorbed onto, the liposome bilayer of the liposome. An oligomer of the present invention may be aggregated with a lipid surfactant and carried within the liposome's internal space; in these cases, the liposome membrane is formulated to resist the disruptive effects of the active agent-surfactant aggregate.

According to one embodiment of the present methods, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present methods are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about C14 to about C20). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention.

Liposomes used according to the present methods may be prepared by any of a variety of techniques that are known in the art. See, e.g., U.S. Pat. No. 4,235,871; Published PCT Application No. WO 96/14057; New RRC, Liposomes: A practical approach, IRL Press, Oxford (1990), pages 33-104; Lasic D D, Liposomes from physics to applications, Elsevier Science Publishers BV, Amsterdam, 1993. For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In another exemplary formulation procedure, the active agent is first dispersed by sonication in a lysophosphatidylcholine or other low CMC surfactant (including polymer grafted lipids) that readily solubilizes hydrophobic molecules. The resulting micellar suspension of active agent is then used to rehydrate a dried lipid sample that contains a suitable mole percent of polymer-grafted lipid, or cholesterol. The lipid and active agent suspension is then formed into liposomes using extrusion techniques as are known in the art, and the resulting liposomes separated from the unencapsulated solution by standard column separation.

In one aspect of the present methods, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988). In certain embodiments, reagents such as DharmaFECT® and Lipofectamine® may be utilized to introduce polynucleotides or proteins into cells.

The release characteristics of a formulation used in the present methods depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In most cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range is typically between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

An oligomer may be formulated to be contained within, or, adapted to release by a surgical or medical device or implant. In certain aspects, an implant may be coated or otherwise treated with an oligomer. For example, hydrogels, or other polymers, such as biocompatible and/or biodegradable polymers, may be used to coat an implant with the compositions of the present invention (i.e., the composition may be adapted for use with a medical device by using a hydrogel or other polymer). Polymers and copolymers for coating medical devices with an agent are well-known in the art. Examples of implants include, but are not limited to, stents, drug-eluting stents, sutures, prosthesis, vascular catheters, dialysis catheters, vascular grafts, prosthetic heart valves, cardiac pacemakers, implantable cardioverter defibrillators, IV needles, devices for bone setting and formation, such as pins, screws, plates, and other devices, and artificial tissue matrices for wound healing.

In addition to the methods provided herein, the oligomers for use according to the invention may be formulated for administration in any convenient way for use in human or veterinary medicine, by analogy with other pharmaceuticals. The antisense oligomers and their corresponding formulations may be administered alone or in combination with other therapeutic strategies in the treatment of inflammation.

In accordance with the methods of the invention, routes of antisense oligomer delivery include, but are not limited to, various systemic routes, including oral and parenteral routes, e.g., intravenous, subcutaneous, intraperitoneal, and intramuscular, as well as inhalation, transdermal, pulmonary and topical delivery. The appropriate route may be determined by one of skill in the art, as appropriate to the condition of the subject under treatment. For example, an appropriate route for delivery of an antisense oligomer in the treatment of a condition of the skin may include topical delivery, while delivery of an antisense oligomer for the treatment of a respiratory condition (e.g., COPD) may include inhalation, intranasal or pulmonary delivery. The oligomer may also be delivered directly to the site of inflammation infection, or to the bloodstream.

The antisense oligomer may be administered in any convenient vehicle which is physiologically acceptable. Such a composition may include any of a variety of standard pharmaceutically acceptable carriers employed by those of ordinary skill in the art. Examples include, but are not limited to, saline, phosphate buffered saline (PBS), water, aqueous ethanol, emulsions, such as oil/water emulsions or triglyceride emulsions, tablets and capsules. The choice of suitable physiologically acceptable carrier will vary dependent upon the chosen mode of administration.

In some instances, as noted above, liposomes may be employed to facilitate uptake of the antisense oligonucleotide into cells. (See, e.g., Williams, S. A., Leukemia 10(12): 1980-1989, 1996; Lappalainen et al., Antiviral Res. 23:119, 1994; Uhlmann et al., antisense oligonucleotides: a new therapeutic principle, Chemical Reviews, Volume 90, No. 4, pages 544-584, 1990; Gregoriadis, G., Chapter 14, Liposomes, Drug Carriers in Biology and Medicine, pp. 287-341, Academic Press, 1979). Hydrogels may also be used as vehicles for antisense oligomer administration, for example, as described in PCT Application Publication No. WO 93/01286 or PCT Application No US1992/005305. Alternatively, the oligonucleotides may be administered in microspheres or microparticles. (See, e.g., Wu, G. Y. and Wu, C. H., J. Biol. Chem. 262:4429-4432, 1987). Alternatively, the use of gas-filled microbubbles complexed with the antisense oligomers can enhance delivery to target tissues, as described in U.S. Pat. No. 6,245,747.

Sustained release compositions may also be used. These may include semipermeable polymeric matrices in the form of shaped articles such as films or microcapsules.

In certain embodiments, the antisense compounds may be administered in an amount and manner effective to result in a peak blood concentration of at least 200-400 nM antisense oligomer. Typically, one or more doses of antisense oligomer are administered, generally at regular intervals, for a period of about one to two weeks. Preferred doses for oral administration are from about 1-100 mg oligomer per 70 kg. In some cases, doses of greater than 100 mg oligomer/patient may be necessary. For i.v. administration, preferred doses are from about 1 mg to 500 mg oligomer per 70 kg. The antisense oligomer may be administered at regular intervals for a short time period, e.g., daily for two weeks or less. However, in some cases the oligomer is administered intermittently over a longer period of time. Administration may be followed by, or concurrent with, administration of an antibiotic or other therapeutic treatment. The treatment regimen may be adjusted (dose, frequency, route, etc.) as indicated, based on the results of immunoassays, other biochemical tests and physiological examination of the subject under treatment.

All publications and patent applications cited in this specification are herein incorporated by reference as if each individual publication or patent application were specifically and individually indicated to be incorporated by reference.

The various embodiments described above can be combined to provide further embodiments. U.S. Provisional Application 62/330,027, filed Apr. 29, 2016 is incorporated herein by reference, in its entirety. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

Although the foregoing disclosure has been described in some detail by way of illustration and example for purposes of clarity of understanding, it will be readily apparent to one of ordinary skill in the art in light of the teachings of this disclosure that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

SEQUENCE LISTING TABLE

| NAME | SEQUENCE | SEQ ID NO: |
|---|---|---|
| LMNA exon 11 | GGCTCCCACTGCAGCAGCTCGGGGGACCCCGCTGAGTA CAACCTGCGCTCGCGCACCGTGCTGTGCGGGACCTGCG GGCAGCCTGCCGACAAGGCATCTGCCAGCGGCTCAGGA GCCCAGGTGGGCGGACCCATCTCCTCTGGCTCTTCTGC CTCCAGTGTCACGGTCACTCGCAGCTACCGCAGTGTGG GGGGCAGTGGGGGTGGCAGCTTCGGGGACAATCTGGTC ACCCGCTCCTACCTCCTGGGCAACTCCAGCCCCCGAAC CCAG | 1 |
| HGPS exon 11 | GGCTCCCACTGCAGCAGCTCGGGGGACCCCGCTGAGTA CAACCTGCGCTCGCGCACCGTGCTGTGCGGGACCTGCG GGCAGCCTGCCGACAAGGCATCTGCCAGCGGCTCAGGA GCCCAGGTGGGCGGACCCATCTCCTCTGGCTCTTCTGC CTCCAGTGTCACGGTCACTCGCAGCTACCGCAGTGTGG GGGGCAGTGGGGGTGGCAGCTTCGGGGACAATCTGGTC ACCCGCTCCTACCTCCTGGGCAACTCCAGCCCCCGAAC CCAG | 2 |
| Ex11-1 | CTGAGCCGCTGGCAGATGCCTTGTC | 3 |
| Ex11-2 | GAGGAGATGGGTCCACCCACCTGGG | 4 |
| rTAT | RRRQRRKKR | 5 |
| Tat | RKKRRQRRR | 6 |
| $R_9F_2$ | RRRRRRRRRFF | 7 |
| $R_5F_2R_4$ | RRRRRFFRRRR | 8 |
| $R_4$ | RRRR | 9 |
| $R_5$ | RRRRR | 10 |
| $R_6$ | RRRRRR | 11 |
| $R_7$ | RRRRRRR | 12 |
| $R_8$ | RRRRRRRR | 13 |
| $R_9$ | RRRRRRRRR | 14 |
| $(RX)_8$ | RXRXRXRXRXRXRXRX | 15 |
| $(RXR)_4$ | RXRRXRRXRRXR | 16 |
| $(RXR)_5$ | RXRRXRRXRRXRRXR | 17 |
| $(RXRRBR)_2$ | RXRRBRRXRRBR | 18 |
| $(RAR)_4F_2$ | RARRARRARRARFF | 19 |
| $(RGR)_4F_2$ | RGRRGRRGRRGRFF | 20 |
| $(RFF)_3R$ | RFFRFFRFFR | 21 |
| $(RXR)_4XB$ | RXRRXRRXRRXRXB | 22 |
| $(RFF)_3RXB$ | RFFRFFRFFRXB | 23 |
| $(RFF)_3RG$ | RFFRFFRFFRG | 24 |
| $R_6G$ | RRRRRRG | 25 |

X is 6-aminohexanoic acid; B is β-alanine; F is phenylalanine; G is glycine; R is arginine; Q is glutamine; K is lysine. Each of SEQ ID NOS: 5-25 may further comprise a group $R^a$ attached to the amino terminus wherein $R^a$ is selected from H, acetyl, benzoyl, and stearoyl.
In some embodiments, IV is acetyl.

EXAMPLES

Materials

1. HGPS Mouse Model

The human BAC clone, RP11-702H12 (RPCI-11 Human BAC Library, BACPAC Resource Center at Children's Hospital Oakland Research Institute, Oakland, Calif.) contains an insert of 164.4 kb of genomic DNA from chromosome 1q including the LMNA gene (25.4 kb) and three other known genes, UBQLN4, MAPBPIP, and RAB25. Recombinogenic targeting of BAC clone RP11-702H12 was performed with a shuttle fragment containing the G608G mutation generated by PCR from genomic DNA of an HGPS fibroblast cell line AG11498 (Coriell Cell Repositories, NIA collection). The Human BACG608G transgenic mouse model for HGPS expresses the mutant human LMNA protein, termed progerin, in all tissues. The mice present with much of the same pathology as HGPS patients. In the heterozygous state, the mice demonstrate loss of vascular smooth muscle cells (VSMC) in the major arteries with stiffening non-responsive vascular elasticity. In the homozygous state the mice show more progressive VSMC loss with adventitial thickening, overall lipodystrophy, taut desiccated skin, thinning hair, kyphosis, joint contracture, and restricted gait. These mice with two copies of the transgene die prematurely at 6-8 months of age.

2. PPMOs

| Compound | Targeting Sequence (TS) | TS SEQ ID NO | 5' CPP 3' | CPP SEQ ID NO |
|---|---|---|---|---|
| PPMO1 | CTGAGCCGCTGGCAGATG CCTTGTC | 3 | EG3-Gly-$R_6$-Ac | 11 |
| PPMO2 | GAGGAGATGGGTCCACCC ACCTGGG | 4 | EG3-Gly-$R_6$-Ac | 11 |

"Gly" indicates a glycine linker attached to the 3' terminal morpholino subunit ring nitrogen by an amide bond at the glycine carboxyl, and also attached at the CPP carboxy terminus of the peptide by an amide bond to the glycine $NH_2$.
"R" is arginine and "Ac" is acetyl.

Example 1 ddPCR Analysis of HGPS Mice Following Treatment with PPMOs Targeting LMNA

Digital Droplet PCR (ddPCR) experiments were performed to measure the expression levels of progerin and wildtype LMNA in HGPS transgenic mice following treatment with PPMO1 (SEQ ID NO: 3) and PPMO2 (SEQ ID NO: 4). A total of 37 mice were divided among the following test groups:

| Group (No. Mice) | Test Compound | Dose per Injection (mg/kg) | Regimen | Route of Admin. |
|---|---|---|---|---|
| 1 (7) | Saline | 0 | 2x weekly | I.V. tail vein |
| 2 (4) | PPMO1 | 60 | 2x weekly | I.V. tail vein |
| 3 (7) | PPMO1 | 20 | 2x weekly | I.V. tail vein |
| 4 (4) | PPMO1 | 7 | 2x weekly | I.V. tail vein |
| 5 (4) | PPMO2 | 60 | 2x weekly | I.V. tail vein |
| 6 (7) | PPMO2 | 20 | 2x weekly | I.V. tail vein |
| 7 (4) | PPMO2 | 7 | 2x weekly | I.V. tail vein |

Figure 2:
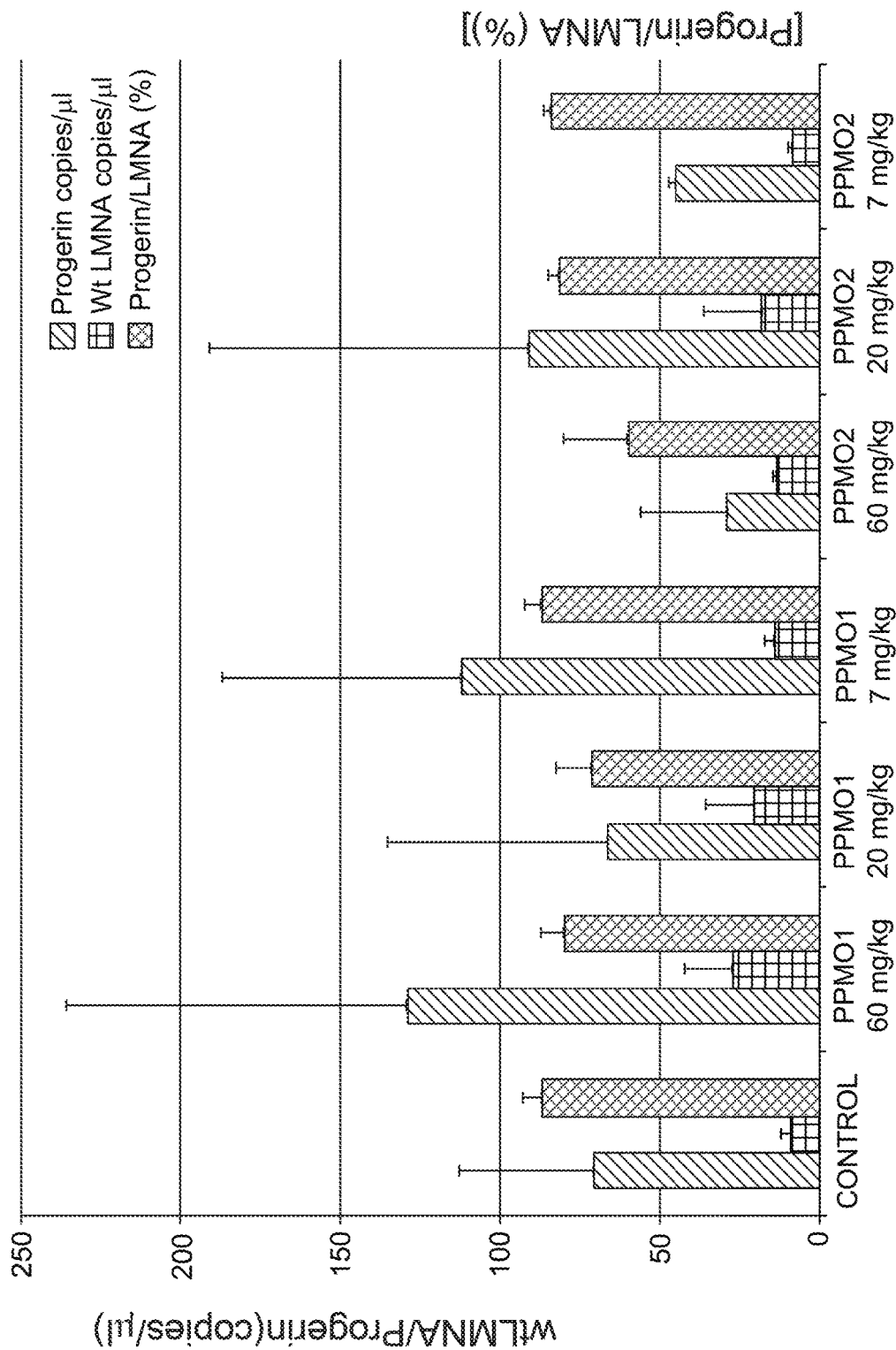
FIG. 2 shows results for ddPCR analysis of lamin A and progerin from the descending aortas of mice treated with PPMO1 (7 mg/kg, 20 mg/kg, or 60 mg/kg), PPMO2 (7 mg/kg, 20 mg/kg, or 60 mg/kg), or saline control for 12 weeks.
Figure 3:
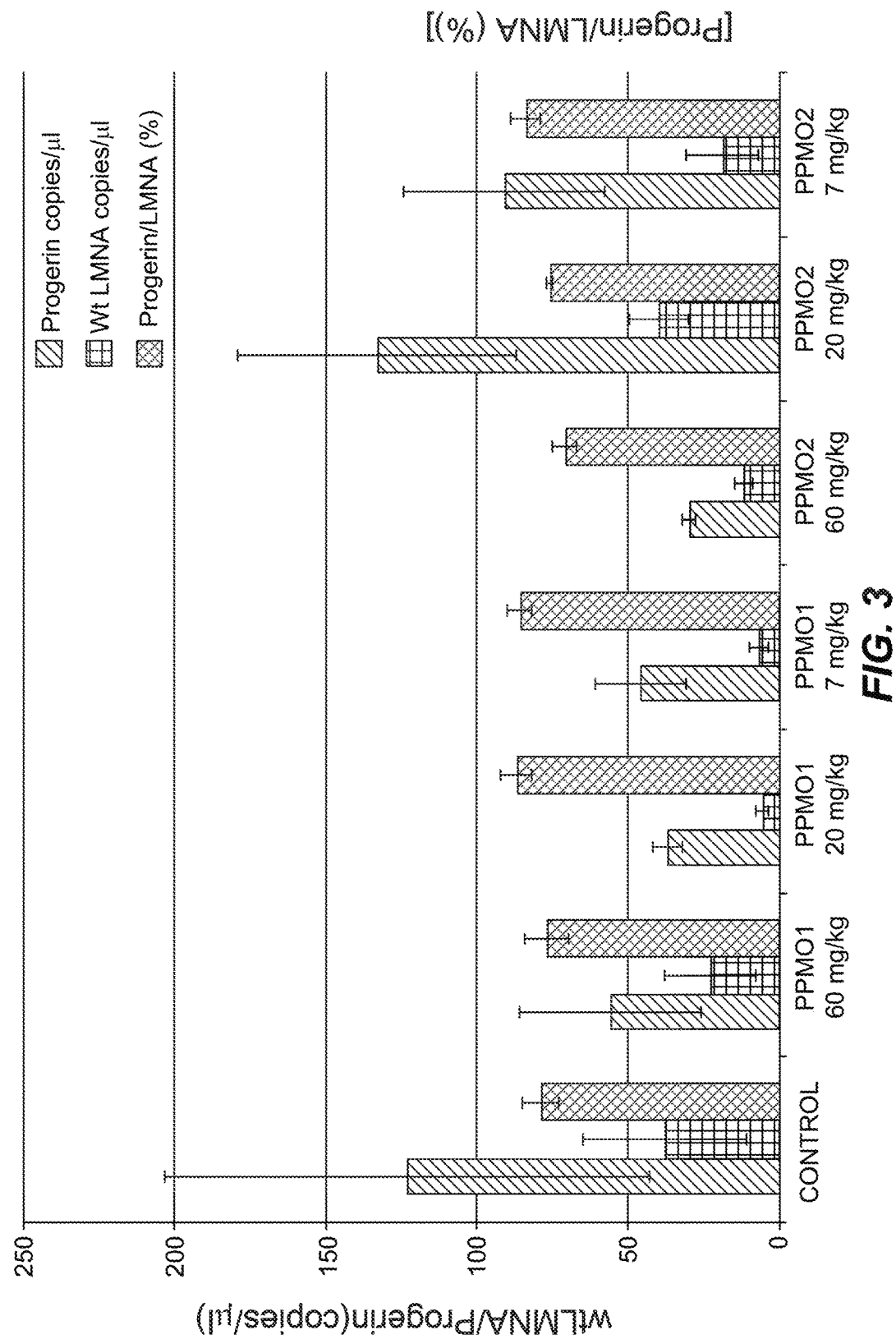
FIG. 3 shows results for ddPCR analysis of lamin A and progerin from the quadriceps of mice treated with PPMO1 (7 mg/kg, 20 mg/kg, or 60 mg/kg), PPMO2 (7 mg/kg, 20 mg/kg, or 60 mg/kg), or saline control for 12 weeks.
Figure 4:
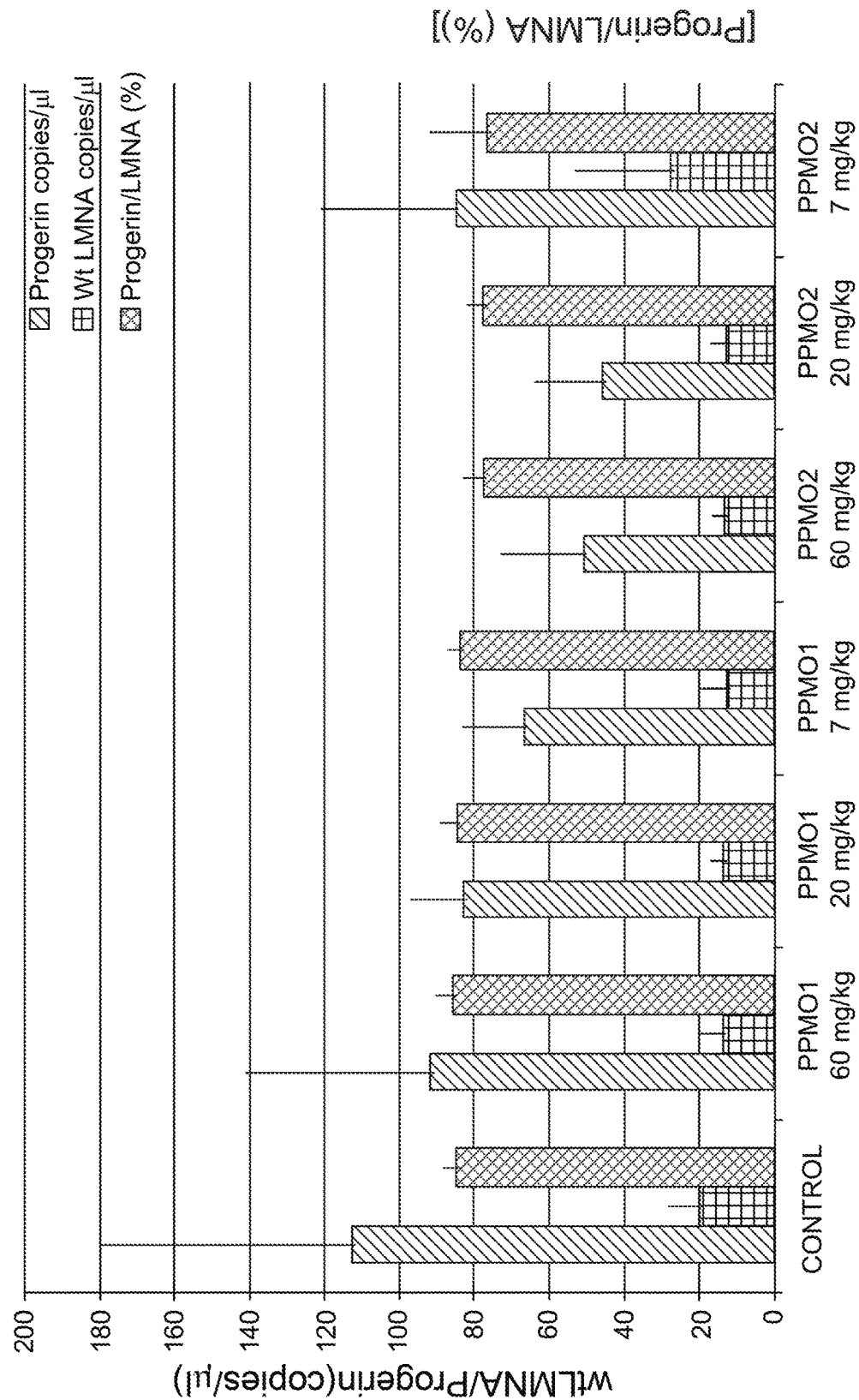
FIG. 4 shows results for ddPCR analysis of lamin A and progerin from the livers of mice treated with PPMO1 (7 mg/kg, 20 mg/kg, or 60 mg/kg), PPMO2 (7 mg/kg, 20 mg/kg, or 60 mg/kg), or saline control for 12 weeks.

Mice were dosed per the above table starting at four weeks of age and sacrificed after 12 weeks. RNA was extracted from heart, liver, quadriceps, and aorta using standard Trizol procedure (Ambion). cDNA were prepared from 0.5 μg total RNA using standard iScript™ cDNA synthesis procedure (Bio-Rad) and analyzed for splice inhibition by ddPCR. The results of the experiments are set forth in FIGS. 1-4.

REFERENCES

Cao, K., C. D. Blair, et al. (2011). "Progerin and telomere dysfunction collaborate to trigger cellular senescence in normal human fibroblasts." *J Clin Invest*.

Egholm, M., O. Buchardt, et al. (1993). "PNA hybridizes to complementary oligonucleotides obeying the Watson-Crick hydrogen-bonding rules." *Nature* 365(6446): 566-8.

Kinali, M., V. Arechavala-Gomeza, et al. (2009). "Local restoration of dystrophin expression with the morpholino oligomer AVI-4658 in Duchenne muscular dystrophy: a single-blind, placebo-controlled, dose-escalation, proof-of-concept study." *Lancet Neurol* 8(10): 918-28.

Osorio, F. G., C. L. Navarro, et al. (2011). "Splicing-directed therapy in a new mouse model of human accelerated aging." *Sci Transl Med* 3(106): 106ra107.

Scaffidi, P. and T. Misteli (2005). "Reversal of the cellular phenotype in the premature aging disease Hutchinson-Gilford progeria syndrome." *Nat Med* 11(4): 440-5.

Svasti, S., T. Suwanmanee, et al. (2009). "RNA repair restores hemoglobin expression in IVS2-654 thalassemic mice." *Proc Natl Acad Sci USA* 106(4): 1205-10.

The invention claimed is:

1. An antisense oligomer compound, or a pharmaceutically acceptable salt thereof, selected from:

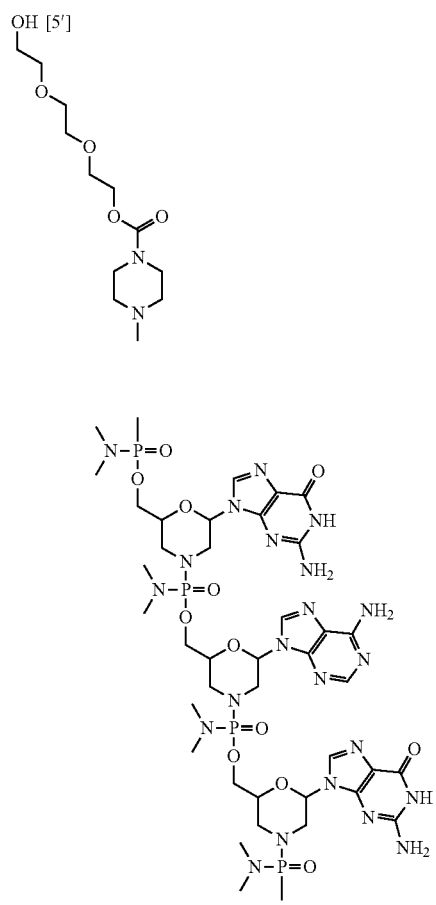

(Va)

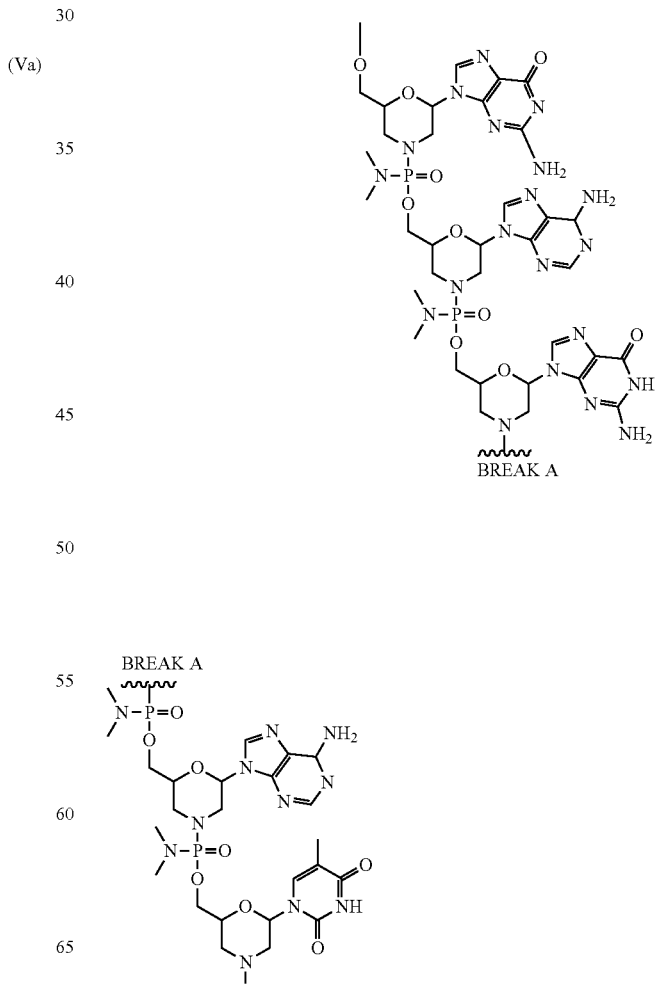

-continued
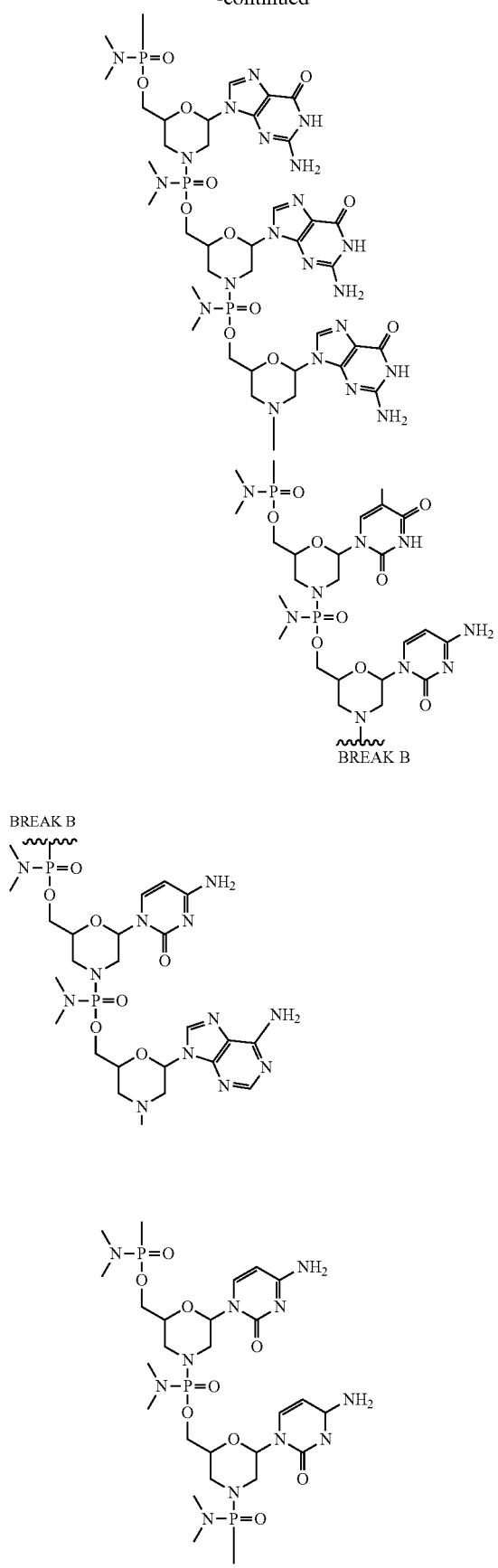
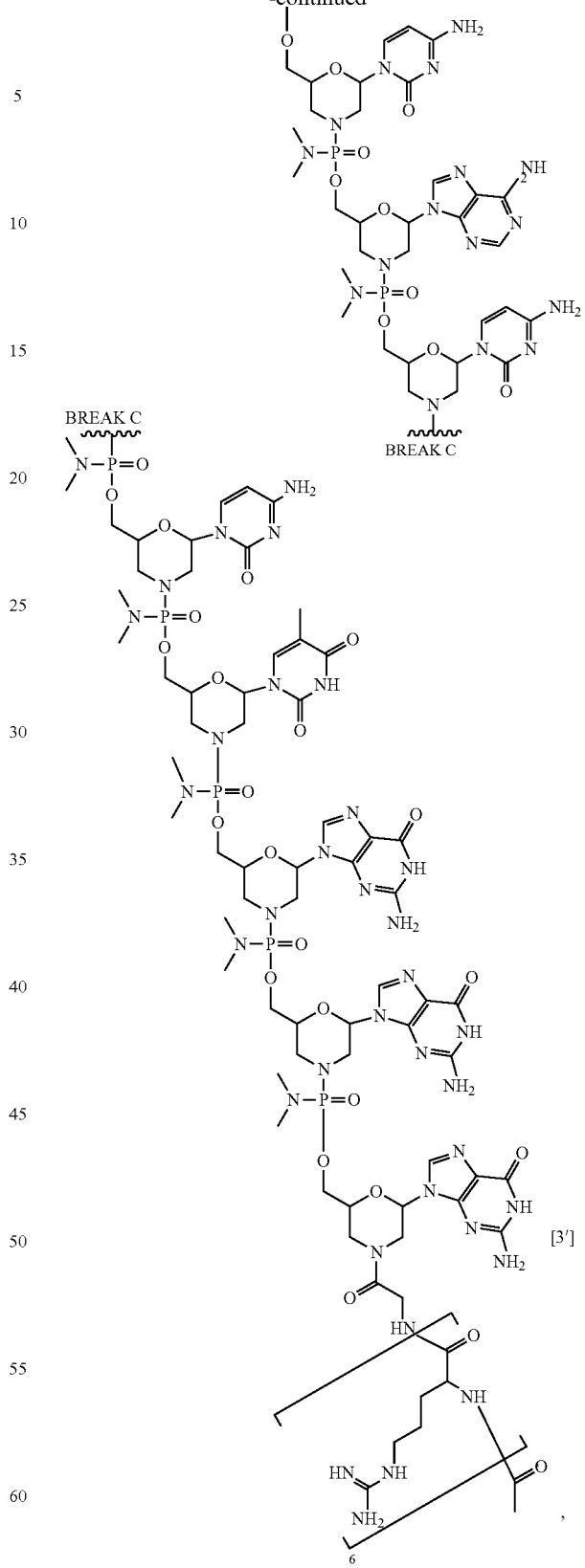
wherein the compound comprises an oligonucleotide and a cell-penetrating peptide, and
wherein the cell-penetrating comprises a peptide of Seq. ID No. 11.

2. The antisense oligomer compound of claim 1, or a pharmaceutically acceptable salt thereof, wherein the oligomer of formula (Vb) is:
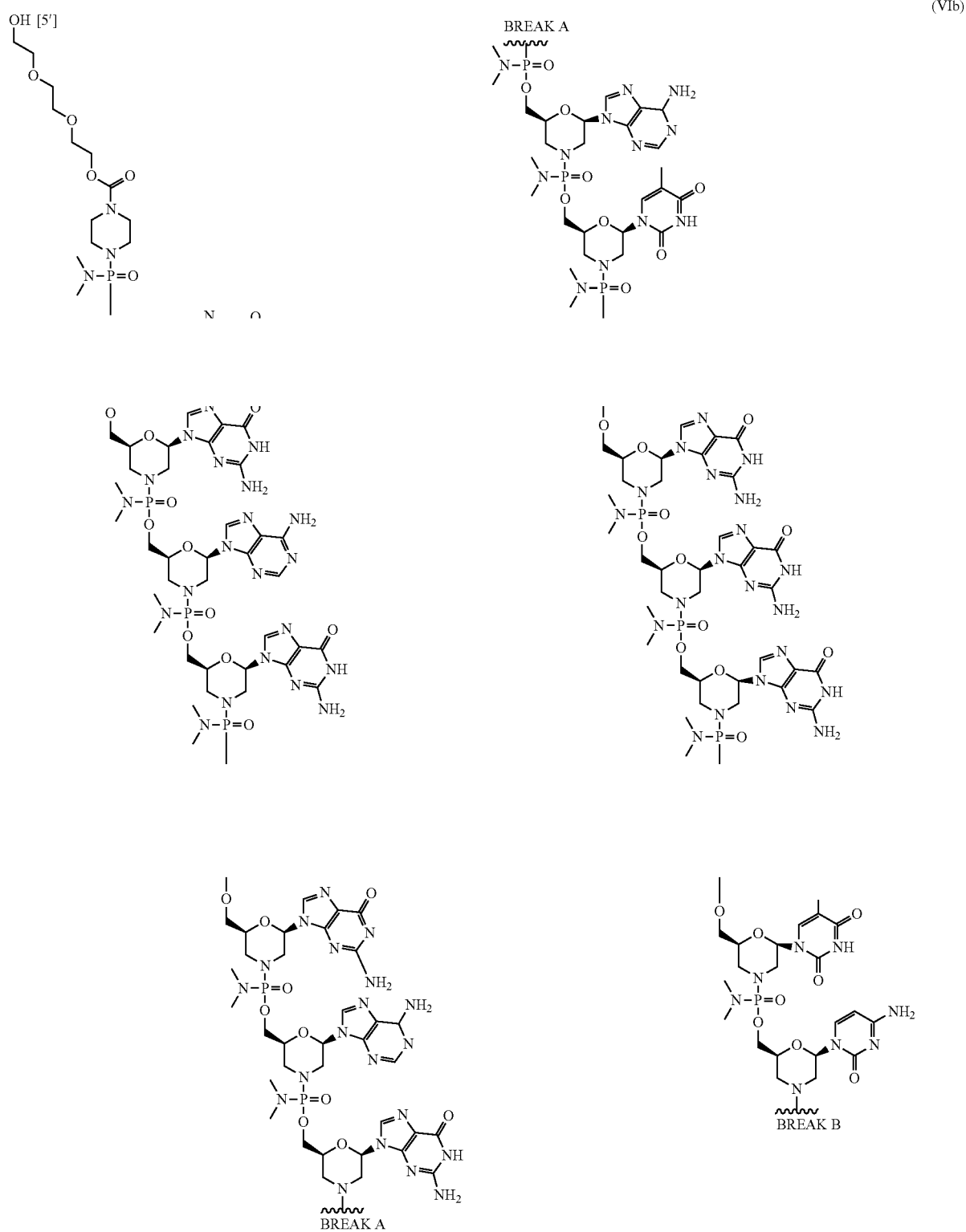
(VIb)

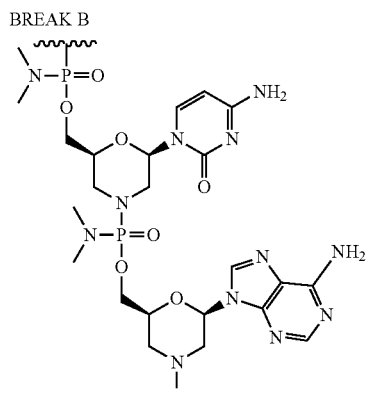
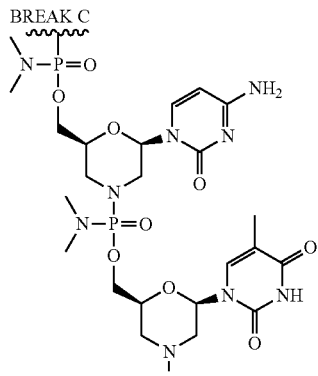
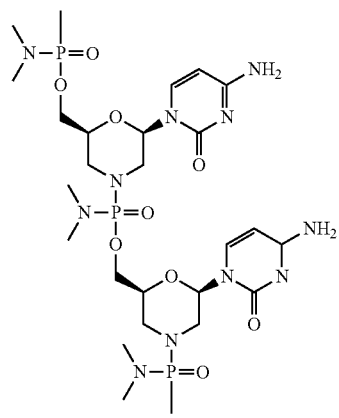
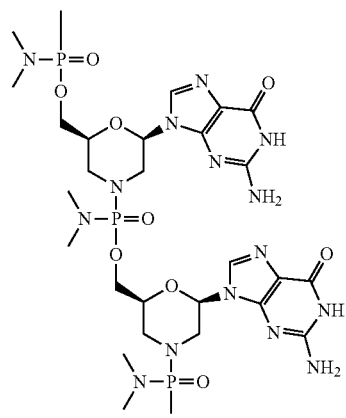
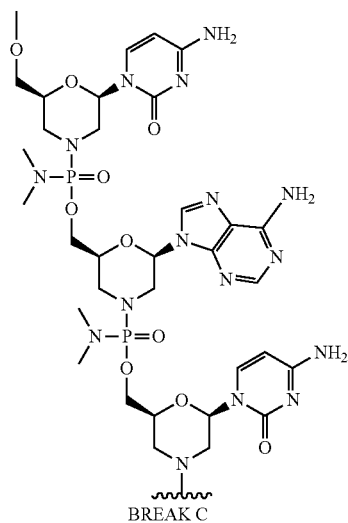
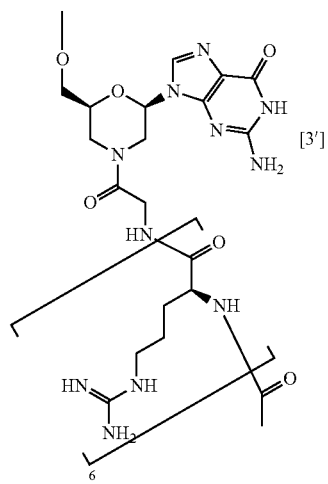
wherein the compound comprises an oligonucleotide and a cell-penetrating peptide, and
wherein the cell-penetrating comprises a peptide of Seq. ID No. 11.

3. A pharmaceutical composition, comprising an antisense oligomer compound of formula (Vb):
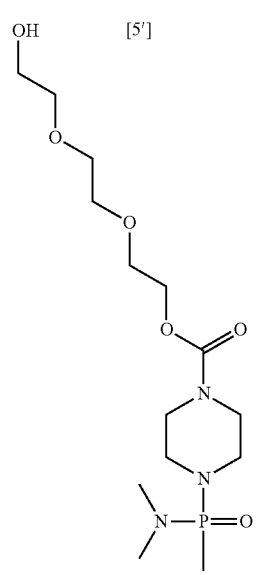
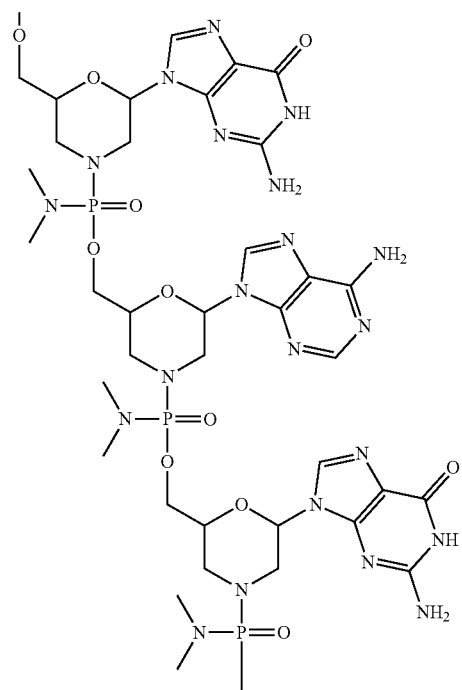
(Vb)

-continued
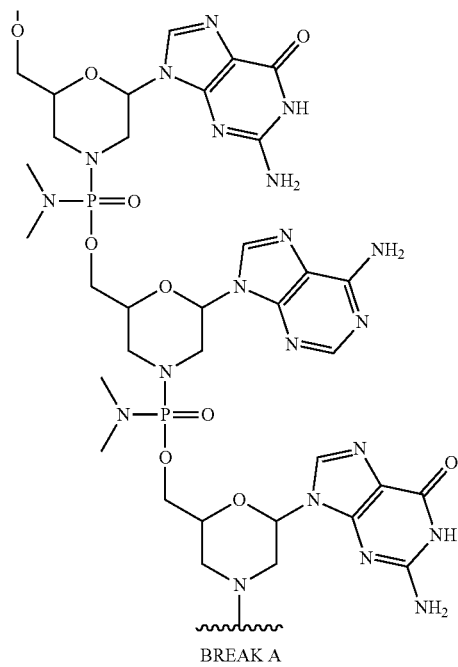
BREAK A
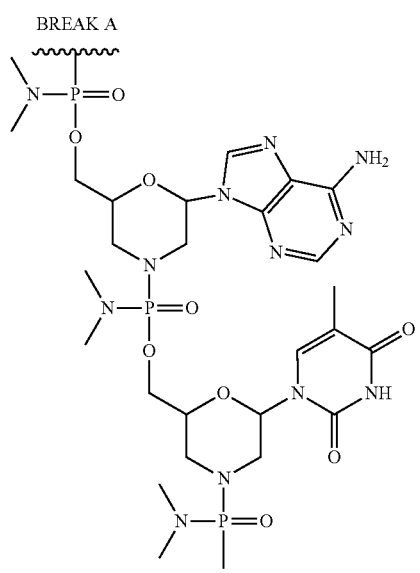
BREAK A

-continued
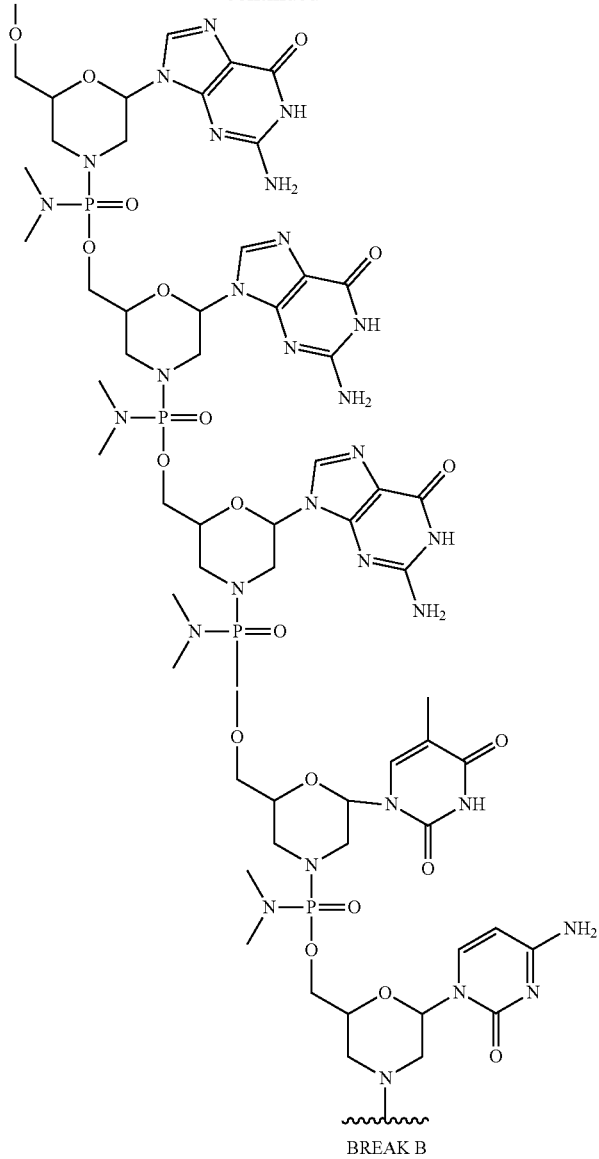
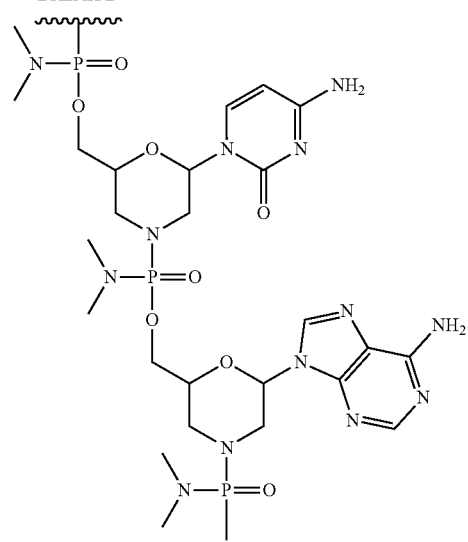
BREAK B

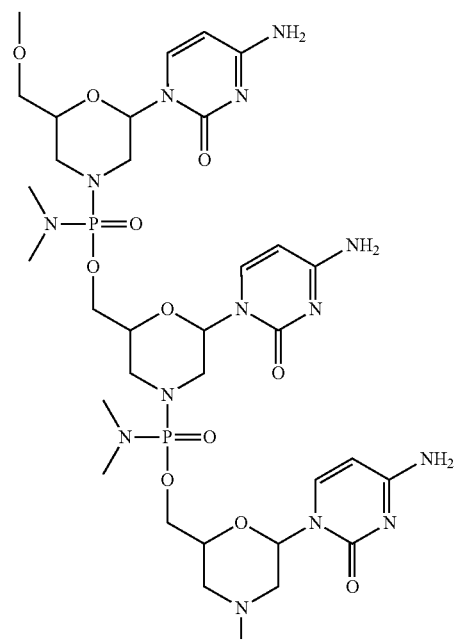
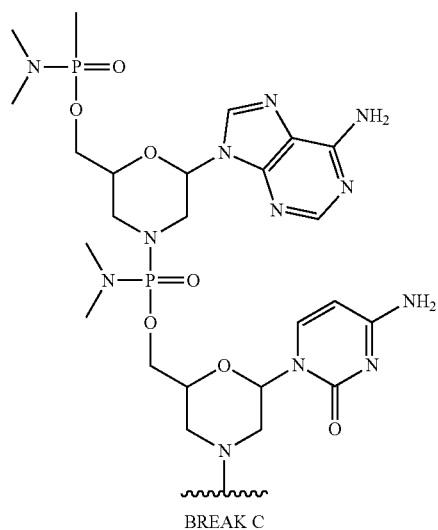
BREAK C

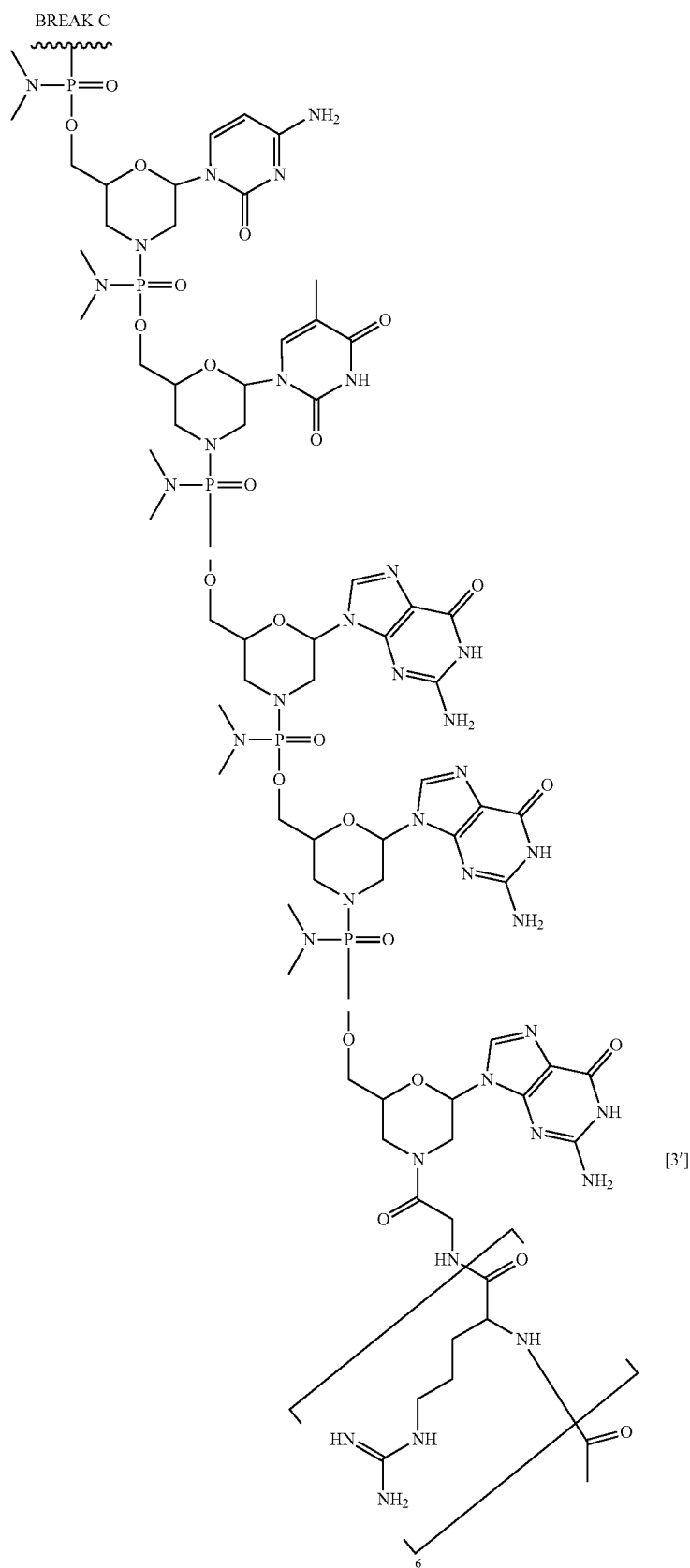

or a pharmaceutically acceptable salt thereof, and a pharmaceutically acceptable carrier,
wherein the compound comprises an oligonucleotide and a cell-penetrating peptide, and
wherein the cell-penetrating comprises a peptide of Seq. ID No. 11.
4. The pharmaceutical composition of claim 3, wherein the antisense oligomer compound is a compound of formula (VIb):
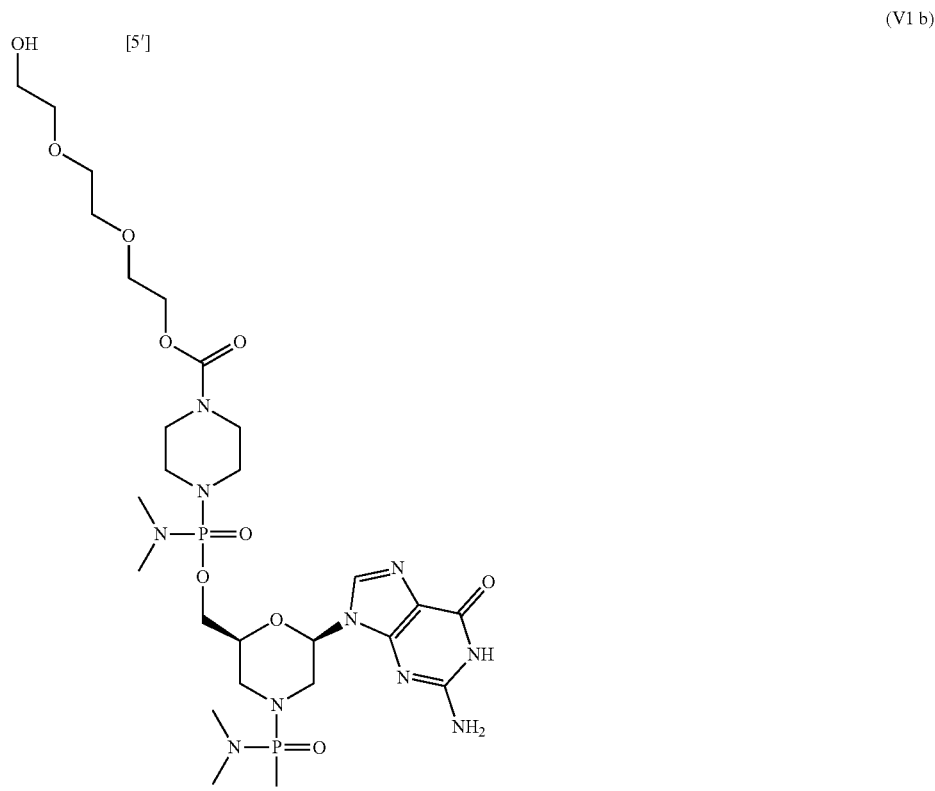
(VIb)
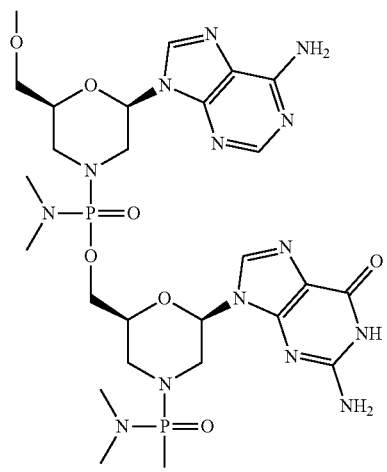

-continued
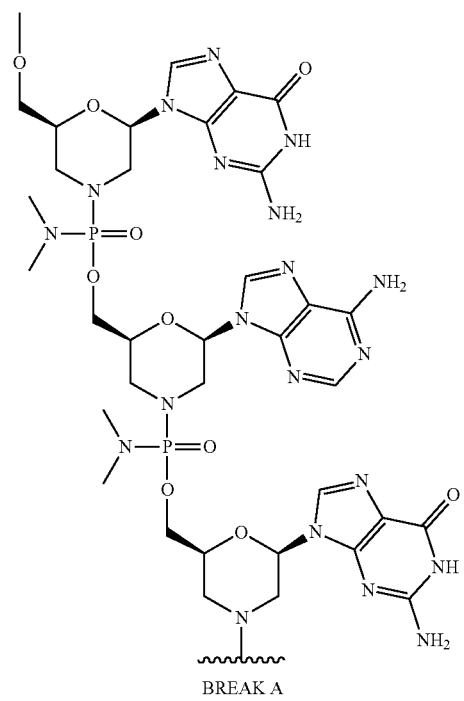
BREAK A
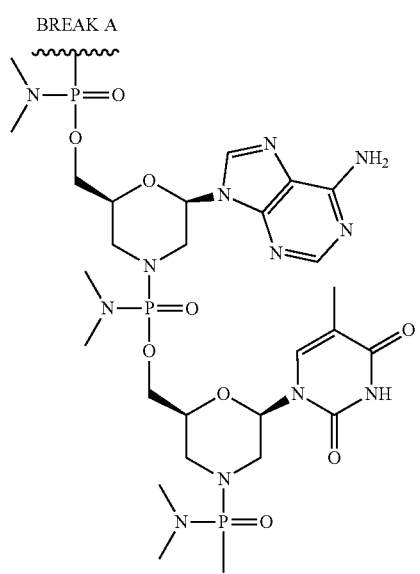

-continued
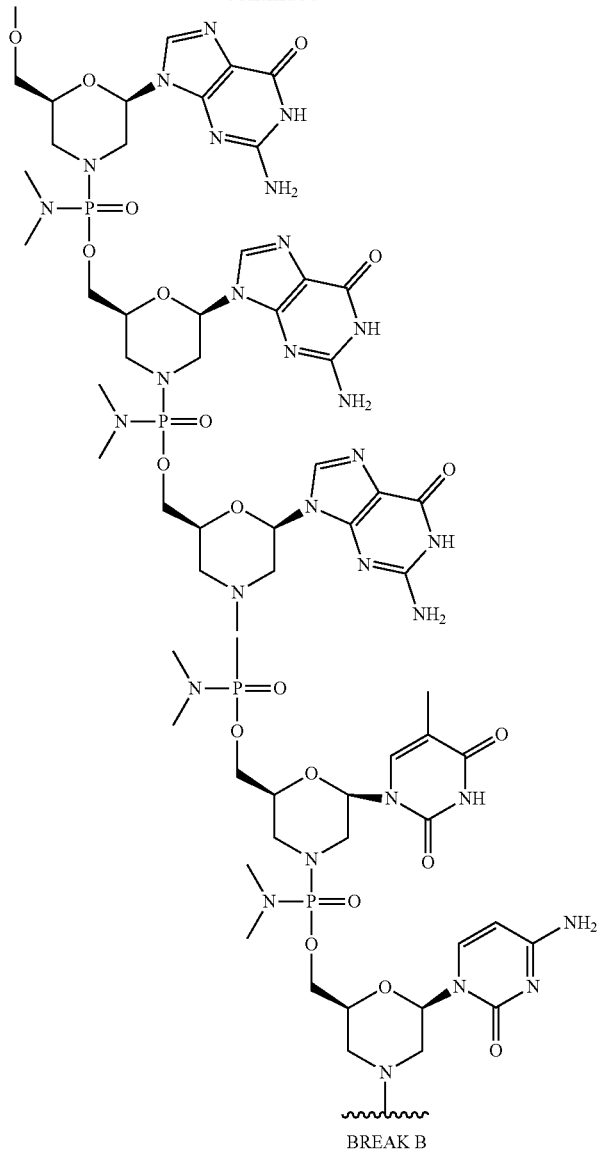
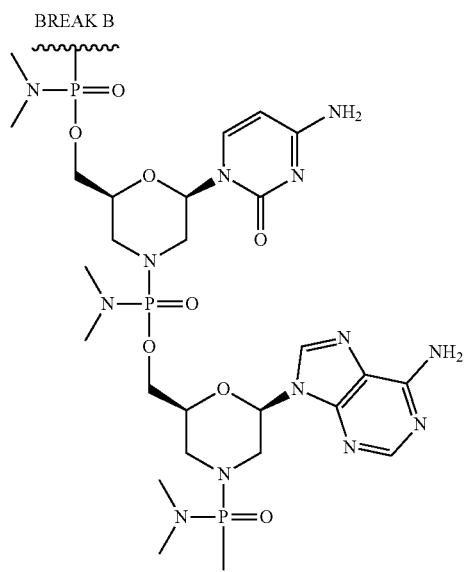
BREAK B

-continued
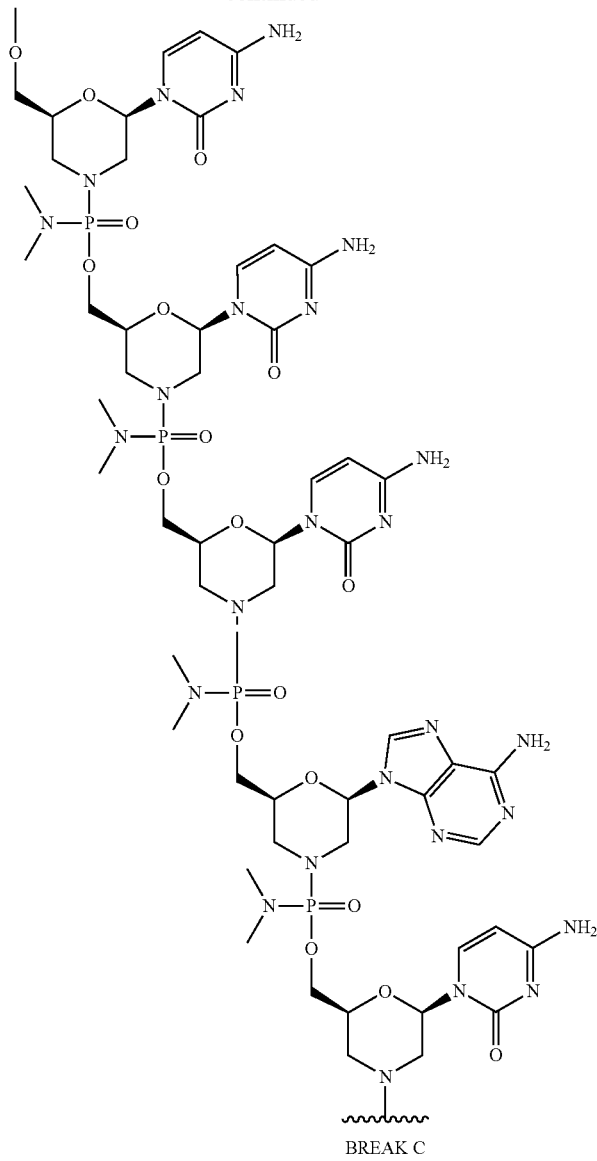
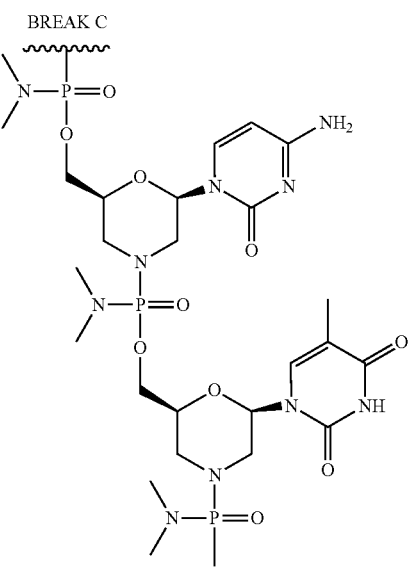

-continued
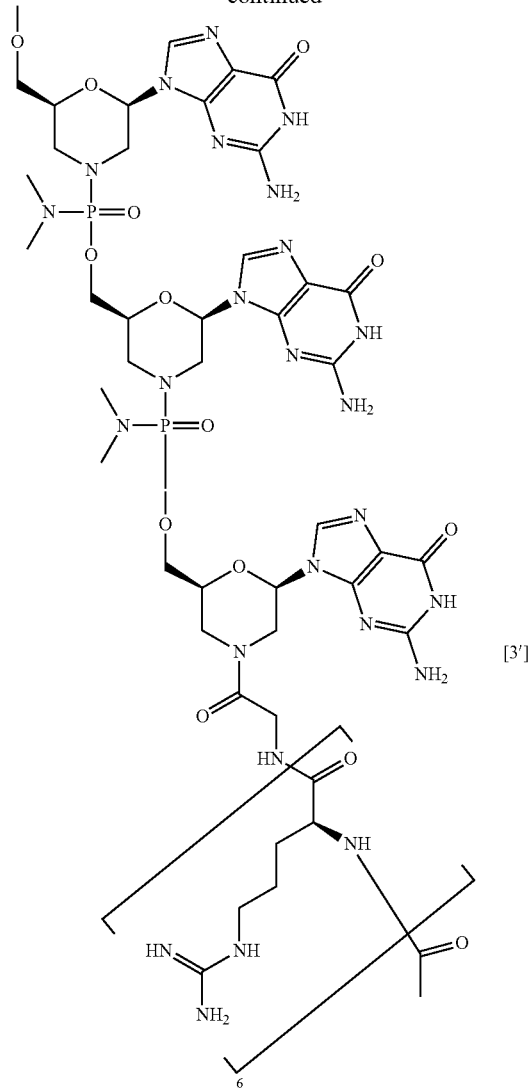
[3']
or a pharmaceutically acceptable salt thereof, and a pharmaceutically acceptable carrier,
wherein the compound comprises an oligonucleotide and a cell-penetrating peptide, and
wherein the cell-penetrating comprises a peptide of Seq. ID No. 11.
* * * * *